United States Patent
Matsumoto et al.

(10) Patent No.: US 12,428,624 B2
(45) Date of Patent: *Sep. 30, 2025

(54) METHOD FOR PRODUCING PANCREATIC ENDOCRINE CELLS

(71) Applicant: Juntendo Educational Foundation, Tokyo (JP)

(72) Inventors: Masahito Matsumoto, Tokyo (JP); Yasushi Okazaki, Tokyo (JP); Izumi Sugahara, Tokyo (JP)

(73) Assignee: Juntendo Educational Foundation, Tokyo (JP)

( * ) Notice: Subject to any disclaimer, the term of this patent is extended or adjusted under 35 U.S.C. 154(b) by 1087 days.

This patent is subject to a terminal disclaimer.

(21) Appl. No.: 17/235,817

(22) Filed: Apr. 20, 2021

(65) Prior Publication Data

US 2021/0238555 A1    Aug. 5, 2021

Related U.S. Application Data

(63) Continuation-in-part of application No. 15/770,910, filed as application No. PCT/JP2016/082095 on Oct. 28, 2016, now Pat. No. 11,499,140.

(30) Foreign Application Priority Data

Oct. 29, 2015  (JP) ................................. 2015-212563

(51) Int. Cl.
| | |
|---|---|
| *C12N 5/071* | (2010.01) |
| *C07K 14/435* | (2006.01) |
| *C07K 14/47* | (2006.01) |
| *C12N 5/074* | (2010.01) |
| *C12N 15/10* | (2006.01) |

(52) U.S. Cl.
CPC .......... *C12N 5/0696* (2013.01); *C07K 14/435* (2013.01); *C07K 14/4702* (2013.01); *C12N 5/0676* (2013.01); *C12N 15/1068* (2013.01); *C12N 2501/13* (2013.01); *C12N 2501/60* (2013.01); *C12N 2501/998* (2013.01); *C12N 2506/1307* (2013.01); *C12N 2506/45* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 8,927,277 B2 | 1/2015 | Yamanaka et al. | |
| 10,214,728 B2 | 2/2019 | Matsumoto et al. | |
| 10,793,832 B2 | 10/2020 | Matsumoto et al. | |
| 2003/0077259 A1 | 4/2003 | Levine et al. | |
| 2009/0280096 A1 | 11/2009 | Kubo et al. | |
| 2011/0112015 A1 | 5/2011 | Julier et al. | |
| 2012/0122214 A1 | 5/2012 | Senju | |
| 2013/0029423 A1 | 1/2013 | Yamanaka et al. | |
| 2017/0211046 A1 | 7/2017 | Matsumoto et al. | |
| 2022/0411762 A1 | 12/2022 | Matsumoto et al. | |

FOREIGN PATENT DOCUMENTS

| | | | |
|---|---|---|---|
| JP | 2003-245067 | 9/2003 | |
| JP | 2005-506072 | 3/2005 | |
| JP | 2009-533047 | 9/2009 | |
| JP | 2013-519371 | 5/2013 | |
| WO | 03/078636 | 9/2003 | |
| WO | 2011/102531 | 8/2011 | |
| WO | WO-2011102531 A1 * | 8/2011 | ........... C12N 5/0696 |
| WO | 2016/002937 | 1/2016 | |

OTHER PUBLICATIONS

Zhou et al Nature, 627-632 (Year: 2008).*
Li et al eLife ; 3: e01846, 1-20 (Year: 2014).*
Karniell Stem cells, 25, 2837-2844 (Year: 2007).*
Limbert et al Cytotherapy, 13: 802-813 (Year: 2011).*
Kang et al Molecular & Cellular Biology, 6366-6379 (Year: 2009).*
Yang et al Diabetologia.; 54(10): 2595-2605 (Year: 2011).*
Leda, Cell. Mol. Life Sci. 74, 2203-2215 (Year: 2017).*
Lalit et al., Cell Stem Cell 18, 354-367 (Year: 2016).*
Cyranoski, Nature, 516: 162-164 (Year: 2014).*
Wang et al Molecular Med. Report, 8, 769-774 (Year: 2013).*
Marta Fontcuberta-PiSunyer et al.Communication Biology, 6: 256, 1-15 (Year: 2023).*
Heremans et al., "Recapitulation of embryonic neuroendocrine differentiation in adult human pancreatic duct cells expressing neurogenin 3", The Journal of Cell Biology, vol. 159, No. 2, 2002, pp. 303-311.
Lee et al., "Expansion and conversion of human pancreatic ductal cells into insulin-secreting endocrine cells", eLIFE Research Article, 2013, pp. 1-22.

(Continued)

*Primary Examiner* — Anoop K Singh

(74) *Attorney, Agent, or Firm* — Grüneberg and Myers PLLC

(57) ABSTRACT

A method for producing pancreatic endocrine cells, including introducing (B) or (D) below into cultured somatic cells to transdifferentiate into a population of pancreatic endocrine cells that include insulin-producing beta-cells: (B) a GLIS1 gene or one or more gene products thereof, a Neurogenin3 gene or one or more gene products thereof, and a Pdx1 gene or one or more gene products thereof; and (D) a GLIS1 gene or one or more gene products thereof, a Neurogenin3 gene or one or more gene products thereof, and a MafA gene or one or more gene products thereof. The GLIS1 gene includes the nucleotide sequence as set forth in SEQ ID NO: 1 or SEQ ID NO: 2. The population of pancreatic endocrine cells are produced without undergoing an iPS cell stage.

2 Claims, 21 Drawing Sheets

Specification includes a Sequence Listing.

(56) References Cited

OTHER PUBLICATIONS

U.S. Office Action dated Jan. 27, 2022 in U.S. Appl. No. 15/770,910, 18 pages.
U.S. Office Action dated Aug. 7, 2023, in U.S. Appl. No. 16/883,572, 9 pages.
U.S. Office Action dated Mar. 12, 2024, in U.S. Appl. No. 16/883,572, 14 pages.
Akinci et al., "Reprogramming of pancreatic exocrine cells towards a beta (β) cell character using Pdx1, Ngn3 and MafA", Biochemical Journal, vol. 442, 2012, pp. 539-550.
Extended European Search Report issued in European Application No. 15815940.0 dated Dec. 13, 2017, 9 pages.
International Search Report issued in International Application No. PCT/JP2015/069296 dated Sep. 8, 2015 with English translation, 5 pages.
International Preliminary Report on Patentability issued in International Application No. PCT/JP2015/069296 dated Dec. 9, 2015 with English translation, 13 pages.
Japanese Office Action of JP 2016-531476 dated Jul. 14, 2020 with English translation, 4 pages.
Japanese Office Action of JP 2016-531476 dated Nov. 26, 2019 with English translation, 4 pages.
Japanese Office Action of JP 2020-171341 dated Oct. 19, 2021 with English translation, 6 pages.
Kang et al., "Transcription Factor Glis3, a Novel Critical Player in the Regulation of Pancreatic β-Cell Development and Insulin Gene Expression", Molecular & Cellular Biology, vol. 29, No. 24, 2009, pp. 6366-6379.
Kim et al., "Glis3 Regulates Neurogenin 3 Expression in Pancreatic β-Cells and Interacts with Its Activator, Hnf6", Molecules and Cells, vol. 34, 2012, pp. 193-200.
Mfopou et al., "Recent advances and prospects in the differentiation of pancreatic cells from human embryonic stem cell", Diabetes, vol. 59, No. 9, Sep. 2010, pp. 2094-2101.
U.S. Office Action received in U.S. Appl. No. 15/323,576, dated Apr. 20, 2018, 14 pages.
U.S. Office Action received in U.S. Appl. No. 16/243,865, dated Oct. 3, 2019, 10 pages.
U.S. Office Action received in U.S. Appl. No. 15/770,910, dated Oct. 31, 2019, 14 pages.
U.S. Office Action received in U.S. Appl. No. 15/770,910, dated Aug. 6, 2020, 17 pages.
U.S. Office Action received in U.S. Appl. No. 16/883,572, dated Sep. 7, 2022, 25 pages.
Scoville et al., "GLIS1-3: emerging roles in reprogramming, stem and progenitor cell differentiation and maintenance", Stem Cell Investigation, vol. 4, Sep. 2017, 11 pages.
Written Opinion issued in International Application No. PCT/JP2015/069296 dated Sep. 8, 2015, 5 pages.
U.S. Office Action received in U.S. Appl. No. 16/883,572, dated Jan. 12, 2023, 6 pages.
Office Action issued Jun. 10, 2021, in U.S. Appl. No. 15/770,910, 19 pages.
Communication issued Jun. 18, 2021, in European Patent Application No. 16859968.6, 7 pages.
Kim, et al., "Identification of Glis1, a Novel Gli-related, Krüppel-like Zinc Finger Protein Containing Transactivation and Repressor Functions", Journal of Biological Chemistry, Aug. 15, 2002; 277(34): 30901-30913; XP055062995; ISSN: 0021 9258; DOI: 10.1074/jbc.M203563200.
Rychlik et al., Optimization of the annealing temperature for DNA amplification in vitro, Nucleic Acids Research; Aug. 22, 1990, 18(21): 6409-6412.
D. Cyranoski, "*The Black Box of Reprogramming*," Nature, vol. 516, Dec. 11, 2014, pp. 162-164.
Kang, et al., "Gli-similar (Glis) *Krüppel-like zinc finger proteins: insights into their physiological functions and critical roles in neonatal diabetes and cystic renal disease*," Histol Histopathol. Nov. 2010; 25(11): 1481-1496, pp. 1-25.
Kojima, et al., "*Discovery and progress of direct cardiac reprogramming*," Cell. Mol. Life Sci. (2017) 74:2203-2215.
Lalit, et al., "*Lineage Reprogramming of Fibroblasts into Proliferative Induced Cardiac Progenitor Cells by Defined Factors*," Cell Stem Cell 18, 354-367, Mar. 3, 2016.
Maekawa, et al., "*Direct reprogramming of somatic cells is promoted by maternal transcription factor Glis1*," Nature, vol. 474, No. 7350, Jun. 9, 2011, pp. 225-229.
Ngo, et al., "*Computational Complexity, Protein Structure Prediction, and the Levinthal Paradox*," The Protein Folding Problem and Tertiary Structure Prediction, pp. 492-495, 12 pages (Year: 1994).
Patel, et al., "*Advances in Reprogramming Somatic Cells to Induced Pluripotent Stem Cells*," Stem Cell Rev and Rep (2010) 6:367-380.
Skolnick, et al., "*From genes to protein structure and function: novel applications of computational approaches in the genomic era*," Trends in Biotech, 18, pp. 34-39 (Year: 2000).
Yang, et al., "*The Krüppel-like zinc finger protein GLIS3 transactivates neurogenin 3 for proper fetal pancreatic islet differentiation in mice*," Diabetologia (2011) 54:2595-2605.
Yasuoka, et al., "*Evolutionary History of GLIS Genes Illuminates Their Roles in Cell Reprogramming and Ciliogenesis*," Mol. Biol. Evol., 37(1):100-109, Advance Access publication Sep. 5, 2019.
Zhou, et al., "*In vivo reprogramming of adult pancreatic exocrine cells β-cells*," Nature, 2008, vol. 455, pp. 627-632.
Extended European Search Report issued Mar. 29, 2019 in European Application No. 16859968.6, 6 pages.
Kim et al., "Epigenetic Regulation of Cardiomyocyte Differentiation from Embryonic and Induced Pluripotent Stem Cells." International Journal of Molecular Sciences, Aug. 10, 2021; 22, 8599; DOI: 10.3390/ijms22168599, pp. 1-19.
Albrecht, "An Epigenetic Switch Between Differentiation and Proliferation in Hepatoblastoma." Cellular and Molecular Gastroenterology and Hepatology, vol. 12, No. 5; 2021, 2352-345X; DOI: 10.1016/j.jcmgh.2021.08.020, pp. 1875-1876.
U.S. Office Action dated Jun. 6, 2024, in U.S. Appl. No. 17/929,495, 22 pages.
U.S. Appl. No. 17/929,495, filed Sep. 2, 2022, 2022/0411762, Matsumoto et al.

\* cited by examiner

FIG. 21A

```
Identity:   1095 / 1295 (84%)
Similarity: 1095 / 1295 (84%)
Gaps:          6 / 1295 (0%)
Strand: Plus / Plus Query     2  TGGTTGCCGGTCGGCAGGCATGCCGCTGGGTGGACTGCTGCGCAGCCTACGAGCAGCAGG   61
             **   **** * ***************** ********* 
Sbjct     5  TGGTGGCCGGGCGGCAGGCGTGCCGCTGGGTGGACTGCTGTGCAGCCTATGAGCAGCAGG   64

Query    62  AGGAGCTGGTGCGGCACATCGAGAAGAGCCACATCGACCAGCGCAAGGGCGAAGACTTCA  121
             ****************************************************** *******
Sbjct    65  AGGAGCTGGTGCGGCACATCGAGAAGAGCCACATCGACCAGCGCAAGGGCGAGGACTTCA  124

Query   122  CCTGCTTCTGGGCCGGGTGTGTGCGGCGCTACAAGCCCTTCAATGCCCGCTACAAGCTGC  181
             ************  ** ***** ******************* ****************
Sbjct   125  CCTGCTTCTGGGCTGGCTGCGTGCGCCGCTACAAGCCCTTCAACGCCCGCTACAAGCTGC  184

Query   182  TCATCCACATGAGGGTACACTCAGGCGAGAAGCCCAACAAGTGCATGTTCGAAGGCTGCA  241
             ***********  * ** ***** ******************************** **********
Sbjct   185  TCATCCACATGCGAGTGCACTCGGGCGAGAAGCCCAACAAGTGCATGTTTGAAGGCTGCA  244

Query   242  GTAAAGCCTTTTCCCGTCTGGAGAACCTGAAGATCCATCTGCGGAGCCACACAGGCGAGA  301
              ** ***** ** ** *********** ********* *** *********** *******
Sbjct   245  GCAAGGCCTTCTCACGGCTGGAGAACCTCAAGATCCACCTGAGGAGCCACACGGGCGAGA  304

Query   302  AACCATACCTGTGCCAGCACCCAGGCTGCCAGAAGGCCTTCAGCAACTCCAGCGACCGTG  361
              ** **************** ** ************************************* *
Sbjct   305  AGCCGTACCTGTGCCAGCACCCGGGTTGCCAGAAGGCCTTCAGCAACTCCAGCGACCGCG  364

Query   362  CCAAGCACCAACGCACCCACCTCGACACGAAGCCATATGCTTGTCAGATCCCTGGCTGCT  421
             ********** ************ *********** ** ** *****************
Sbjct   365  CCAAGCACCAGCGCACCCACCTAGACACGAAGCCGTACGCCTGTCAGATCCCTGGCTGCT  424

Query   422  CCAAGCGCTACACGGACCCCAGCTCCCTCCGCAAGCACGTGAAGGCCCACTCAGCCAAAG  481
             ************ ******************************* *********** *********
Sbjct   425  CCAAGCGCTACACAGACCCCAGCTCCCTCCGCAAGCACGTCAAGGCCCATTCAGCCAAAG  484

Query   482  AGCAGCAGGTGCGTAAGAAGCTGCACACAGGTGCCGACCCAGAGGCTGATGTTCTGTCCG  541
             ************************ * **  * *** * *****  ** ** *** ***
Sbjct   485  AGCAGCAGGTGCGTAAGAAGCTGCATGCGGGCCCTGACACCGAGGCCGACGTCCTGACCG  544

Query   542  AGTGTCTGTCCCTGCAGCAGCTCCAAGCATCCACACTGTTGCCGGCCAGCAGAGGGAAGG  601
             ********  ************** * ******** * ** * ******  ** ****
Sbjct   545  AGTGTCTGGTCCTGCAGCAGCTCCACACGTCCACACAGCTGGCTGCCAGCGACGGCAAGG  604
```

FIG. 21B

```
Query    602   GCAGCCAAACCCTGAGCCAGGAGCTCCTCCCAGGTGTGTATCCTGGCTCCGTCACCCCAC   661
               *  **  **** ********** ************************ *******  *
Sbjct    605   GTGGCTGTGGCCTGGGCCAGGAGCTGCTCCCAGGTGTGTATCCTGGCTCCATCACCCCCC   664

Query    662   AAAACGGGCTTGCTTCAGGCATCCTGTCCCCCTCCCACGATGTCCCTTCCAGGCACCACC   721
               *  ***** *****  ** *** ***** ****   * ***** ** ************
Sbjct    665   ATAACGGACTTGCATCGGGCCTCCTGCCCCCAGCGCACGACGTACCTTCCAGGCACCACC   724

Query    722   CACTGGAGGTCCCCACTGGTTCCCACCACCACCTGTCCCCTCTGCCCACAGCTGAGAGCA   781
               *  ***** * *  **** **************** **************  *******
Sbjct    725   CGCTGGATGCCACCACCAGTTCCCACCACCATCTGTCCCCTCTGCCCATGGCTGAGAGCA   784

Query    782   CCAGGGATGGCCTGGGGCCCAGTCTCCTTTCACCCATGGTCAGCCCACTGAAGGGGCTTG   841
               ** *******  ********* * ***** ***** ** ******** *********  *
Sbjct    785   CCCGGGATGGGTTGGGGCCCGGCCTCCTCTCACCAATAGTCAGCCCCCTGAAGGGGCTGG   844

Query    842   GTCCCCCACCGCTACCACCAGCCTCCCAGAGTCAGTCTCCAGGGGACAGTCATTCTCTA   901
               *  ** ** ***** ** *** ***** ** ***** *****  * *** * *  *
Sbjct    845   GGCCACCGCCGCTGCCCCCATCCTCTCAGAGCCATTCTCCGGGGGGCCAGCCCTTCCCCA   904

Query    902   CAGTCCCCAGCAAGCCTACCTACCCATCCTTCCAAAGCCC------ACCACCTCTGCCCA   955
               ** *************  ********  *******  *****         ** **********
Sbjct    905   CACTCCCCAGCAAGCCGTCCTACCCACCCTTCCAGAGCCCTCCACCCCCGCCTCTGCCCA   964

Query    956   GCCCCAAGGCTACCAAGGCAGTTTCCATTCCATCCAGAACTGCTTCCCCTACGCTGACT   1015
               ****  ***** *****  ************ **********  ***********  *   ****
Sbjct    965   GCCCACAAGGTTACCAGGGCAGTTTCCACTCCATCCAGAGTTGCTTCCCCTATGGCGACT   1024

Query    1016  GCTACCGGGCCACTGAGCCAGCAGCCTCCAGGGATGGACTGGTGGGTGATGCCCACGGTT   1075
               ********    ****  *********    ****  ******** ** ** *********
Sbjct    1025  GCTACCGGATGGCTGAACCAGCAGCCGGTGGGGACGGACTGGTCGGGAGACCCACGGTT   1084

Query    1076  TCAACCCCTTGCGACCCAGCACATACTCCAGCCTCAGCACACCTTTATCCGCACCAGGCT   1135
               ********  ****  ****    ***  ************* ** **  *  **  ******
Sbjct    1085  TCAACCCCCTGCGGCCCAATGGCTACCACAGCCTCAGCACGCCCTTGCCTGCCACAGGCT   1144

Query    1136  ACGAGACCCTGGCAGAAACGCCGTGTCCCCCAGCGCTGCAGCCACAGCCAGCTGAAGACC   1195
               *  *** *******  **   * **  ** **********  *  ****** *******
Sbjct    1145  ATGAGGCCCTGGCTGAGGCCTCATGCCCCACAGCGCTGCCACAGCAGCCATCTGAAGATG   1204

Query    1196  TGGTACCTAGTGGTCCTGAGGACTGTGGCTTCTTCCCCAATGGGGCCTTTGACCACTGTC   1255
               ****  *  ** ** ** **************************** ************  *
Sbjct    1205  TGGTGTCCAGCGGCCCCGAGGACTGTGGCTTCTTCCCCAATGGAGCCTTTGACCACTGCC   1264

Query    1256  TGAGTCACATCCCGTCCATCTACACTGACACCTGA   1290
               **  * *********  ************  **********
Sbjct    1265  TGGGCCACATCCCCTCCATCTACACAGACACCTGA   1299
```

METHOD FOR PRODUCING PANCREATIC ENDOCRINE CELLS

CROSS-REFERENCE TO RELATED APPLICATIONS

This application is a continuation-in-part of co-pending U.S. patent application Ser. No. 15/770,910 filed on Apr. 25, 2018, which is the National Stage entry under § 371 of International Patent Application No. PCT/JP2016/082095 filed on Oct. 28, 2016, which claims the benefit of priority to Japanese Patent Application No. 2015-212563 filed on Oct. 29, 2015. The contents of the priority applications are incorporated by reference in their entirety.

REFERENCE TO A SEQUENCE LISTING

The present application is accompanied by an ASCII text file as a computer readable form containing the sequence listing entitled, "003277USCIP01_SL_ST25.txt", created on Apr. 14, 2021, with a file size of 24,933 bytes, the content of which is hereby incorporated by reference in its entirety.

BACKGROUND OF THE INVENTION

Field of the Invention

The present invention relates to a method for producing pancreatic endocrine cells from somatic cells.

Description of Related Art

Pancreatic endocrine cells have been expected to be used as, for example, a material for regenerative therapies for diabetes or a material used for screening of diabetes drugs. In terms of the regenerative therapies, for example, it has been expected that P cells, which are one of the pancreatic endocrine cells and produce insulin, are administered to type I diabetes patients who are insulin-deficient.

Therefore, keen demand has arisen for developing a method for preparing pancreatic endocrine cells in vitro in large quantities.

There has been proposed a method for producing β cells using embryonic stem cells (hereinafter may be referred to as "ES cells") or induced pluripotent stem cells (hereinafter may be referred to as "iPS cells"). However, the method has the following problems. Firstly, the method is complicated because culturing environments are needed to be properly adjusted by, for example, adding various inhibitors involved in development or differentiation to a cell culture medium. Secondly, the method may be unreproducible. Thirdly, the method is problematic in terms of efficiency because other cells than the β cells are also produced. Finally, the method takes at least 21 days to 30 days to produce the β cells, that is, the β cells are not capable of being produced in a short period of time.

Therefore, at present, keen demand has arisen for promptly providing a method for producing pancreatic endocrine cells, the method being simple, easily reproduced, excellent in production efficiency, and capable of producing the pancreatic endocrine cells in a short period of time.

Note that, GLIS1 (GLIS family zinc finger 1) has been known to improve an establishment improving efficiency of iPS cells (see, e.g., PTL 1).

However, it has not been that the GLIS1 is involved in direct transformation of somatic cells into pancreatic endocrine cells without undergoing the stem cell stage.

CITATION LIST

Patent Literature

PTL 1: Japanese Patent Application Laid-Open (JP-A) No. 2013-519371

SUMMARY OF THE INVENTION

Technical Problem

The present invention aims to solve the above existing problems and achieve the following object. That is, the present invention has an object to provide a method for producing pancreatic endocrine cells, the method being simple, easily reproduced, excellent in production efficiency, and capable of producing the pancreatic endocrine cells in a short period of time, and a transdifferentiation agent that transdifferentiates somatic cells to pancreatic endocrine cells.

Solution to Problem

Means for solving the above problems are as follows.
<1> A method for producing pancreatic endocrine cells, the method including
   introducing (B) or (D) below into cultured somatic cells to transdifferentiate into a population of pancreatic endocrine cells comprising insulin-producing beta-cells:
(B) a GLIS1 gene or one or more gene products thereof,
a Neurogenin3 gene or one or more gene products thereof, and
a Pdx1 gene or one or more gene products thereof, and
(D) a GLIS1 gene or one or more gene products thereof.
a Neurogenin3 gene or one or more gene products thereof, and
a MafA gene or one or more gene products thereof,
   wherein the GLIS1 gene comprises the nucleotide sequence as set forth in SEQ ID NO: 1 or SEQ ID NO: 2, and
   wherein the population of pancreatic endocrine cells are produced without undergoing an iPS cell stage
<2> A transdifferential agent including
   (B) or (D) below:
(B) GLIS1 gene or one or more gene products thereof,
a Neurogenin3 gene or one or more gene products thereof, and
a Pdx1 gene or one or more gene products thereof, and
(D) a GLIS1 gene or one or more gene products thereof,
a Neurogenin3 gene or one or more gene products thereof, and
a MafA gene or one or more gene products thereof,
   wherein the GLIS1 gene comprises the nucleotide sequence as set forth in SEO ID NO: 1 or SEO ID NO: 2,
   wherein the transdifferentiation agent is configured to transdifferentiate cultured somatic cells into a population of pancreatic endocrine cells comprising insulin-producing beta-cells, and wherein the population of pancreatic endocrine cells are produced without undergoing an iPS cell stage Advantageous Effects of Invention Advantageous Effects of Invention According to the present invention, it is possible to solve the above existing problems and achieve the above object. That is, the present invention can provide a method for producing pancreatic endocrine cells, the method being simple, easily reproduced, excellent in production efficiency, and capable of producing the pancreatic endocrine cells in a short period of time and a transdifferentiation agent that transdifferentiates somatic cells to pancreatic endocrine cells.

BRIEF DESCRIPTION OF THE DRAWINGS

FIG. 21A is a view illustrating the results of sequence identity analysis in Test Example 18.

FIG. 21B is a view illustrating the results of sequence identity analysis in Test Example 18.

Figure 1A:
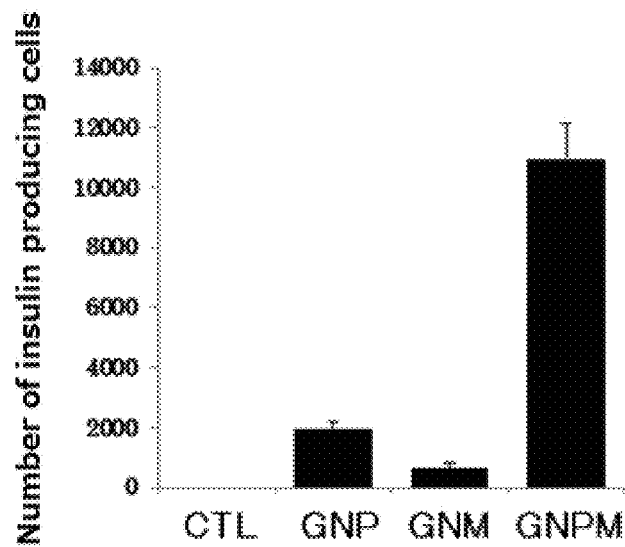
FIG. 1A is a graph illustrating the measurement results of the number of DsRed2-positive insulin producing cells in Test Example 1-1.

DETAILED DESCRIPTION OF THE INVENTION (Production Method of Pancreatic Endocrine Cells)

The method for producing pancreatic endocrine cells of the present invention includes at least an introduction step; and, if necessary, further includes other steps.

<Introduction Step>

The introduction step is a step of introducing (A), (B), (C), or (D) below into somatic cells:

(A) a mutated GLIS1 gene having a sequence identity of 85% or more to a base sequence as set forth in SEQ ID NO: 1 or 2 or one or more gene products thereof, a Neurogenin3 gene or one or more gene products thereof, a Pdx1 gene or one or more gene products thereof, and a MafA gene or one or more gene products thereof (hereinafter may be referred to as "gene or one or more gene products thereof (A)");

(B) a mutated GLIS1 gene having a sequence identity of 85% or more to a base sequence as set forth in SEQ ID NO: 1 or 2 or one or more gene products thereof, a Neurogenin3 gene or one or more gene products thereof, and a Pdx1 gene or one or more gene products thereof (hereinafter may be referred to as "gene or one or more gene products thereof (B)");

(C) a GLIS1 gene or one or more gene products thereof, a Neurogenin3 gene or one or more gene products thereof, a Pdx1 gene or one or more gene products thereof, and a MafA gene or one or more gene products thereof (hereinafter may be referred to as "gene or one or more gene products thereof (C)"); and (D) a mutated GLIS1 gene having a sequence identity of 85% or more to a base sequence as set forth in SEQ ID NO: 1 or 2 or one or more gene products thereof, a Neurogenin3 gene or one or more gene products thereof, and a MafA gene or one or more gene products thereof (hereinafter may be referred to as "gene or one or more gene products thereof (D)").

The gene or one or more gene products thereof (A), the gene or one or more gene products thereof (B), and the gene or one or more gene products thereof (D) are preferably the following genes or one or more gene products thereof.

(A) A mutated GLIS1 gene having a sequence identity of 85% or more to a base sequence as set forth in SEQ ID NO: 1 or one or more gene products thereof, a Neurogenin3 gene or one or more gene products thereof, a Pdx1 gene or one or more gene products thereof, and a MafA gene or one or more gene products thereof.

(B) A mutated GLIS1 gene having a sequence identity of 85% or more to a base sequence as set forth in SEQ ID NO: 1 or 2 or one or more gene products thereof, a Neurogenin3 gene or one or more gene products thereof, and a Pdx1 gene or one or more gene products thereof.

(D) A mutated GLIS1 gene having a sequence identity of 85% or more to a base sequence as set forth in SEQ ID NO: 1 or 2 or one or more gene products thereof, a Neurogenin3 gene or one or more gene products thereof, and a MafA gene or one or more gene products thereof.

The gene or one or more gene products thereof (A), the gene or one or more gene products thereof (B), and the gene or one or more gene products thereof (D) are preferably the following genes or one or more gene products thereof.

(A) A mutated GLIS1 gene having a sequence identity of 85% or more to a base sequence as set forth in SEQ ID NO: 2 or one or more gene products thereof, a Neurogenin3 gene or one or more gene products thereof, a Pdx1 gene or one or more gene products thereof, and a MafA gene or one or more gene products thereof.

(B) A mutated GLIS1 gene having a sequence identity of 85% or more to a base sequence as set forth in SEQ ID NO: 2 or one or more gene products thereof, a Neurogenin3 gene or one or more gene products thereof, and a Pdx1 gene or one or more gene products thereof.

(D) A mutated GLIS1 gene having a sequence identity of 85% or more to a base sequence as set forth in SEQ ID NO: 2 or one or more gene products thereof, a Neurogenin3 gene or one or more gene products thereof, and a MafA gene or one or more gene products thereof.

The gene products refer to mRNAs transcribed from genes or proteins translated from the mRNAs.

<<Genes or One or More Gene Products Thereof

—Aspect—

An aspect of the genes or one or more gene products thereof to be introduced into the somatic cells in the introduction step is not particularly limited and may be appropriately selected depending on the intended purpose, so long as the genes or one or more gene products thereof (A), the genes or one or more gene products thereof (B), the genes or one or more gene products thereof (C), or the genes or one or more gene products thereof (D) is included. However, from the viewpoint of excellent production efficiency of the pancreatic endocrine cells, the genes or one or more gene products thereof (A), the genes or one or more gene products thereof (B), or the genes or one or more gene products thereof (D) is preferably included, and the genes or one or more gene products thereof (A) or the genes or one or more gene products thereof (D) is more preferably included.

The genes or one or more gene products thereof to be introduced into the somatic cells in the introduction step may consist of the genes or one or more gene products thereof (A), the gene or one or more gene products thereof (B), the genes or one or more gene products thereof (C), or the genes or one or more gene products thereof (D), or may include other genes or one or more gene products thereof.

—GLIS1 Gene or One or More Gene Products Thereof—

The GLIS family gene is an important gene that is widely preserved during evolution across biological species from lower organisms to higher organisms (see Yasuoka Y, Matsumoto M, Yagi K, Okazaki Y., "Evolutionary history of GLIS genes illuminates their roles in cell reprogramming and ciliogenesis.", Mol. Biol. Evol., 37(1), 100-109, 2019. doi:10.1093/molbev/msz205).

A source of the GLIS1 gene is not particularly limited and may be appropriately selected depending on the intended purpose. Examples thereof include human and mouse.

Sequence information of the GLIS1 gene is available from known databases. For example, the sequence information is available from NCBI under Accession numbers of NM_147193 (human) or NM_147221 (mouse).

—Mutated GLIS1 Gene or One or More Gene Products Thereof—

The mutated GLIS1 gene refers to a gene having a sequence identity of 85% or more to a base sequence as set forth in SEQ ID NO: 1 or 2.

More specifically, the mutated GLIS1 gene refers to at least one of a mutated GLIS1 gene having a sequence identity of 85% or more to a base sequence as set forth in SEQ ID NO: 1 or one or more gene products thereofi and a mutated GLIS1 gene having a sequence identity of 85% or more to a base sequence as set forth in SEQ ID NO: 2 or one or more gene products thereof.

The mutated GLIS1 gene consisting of the base sequence as set forth in SEQ ID NO: 1 refers to a sequence of a gene coding for a protein in which 360 amino acid residues at N-terminus of a mouse GLIS1 protein are deleted.

The sequence identity of the mutated GLIS1 gene having a sequence identity of 85% or more to the base sequence as set forth in SEQ ID NO: 1 is not particularly limited and may be appropriately selected depending on the intended purpose. However, it is preferably 90% or more identical to the base sequence as set forth in SEQ ID NO: 1, more preferably 95% or more identical to the base sequence as set forth in SEQ ID NO: 1, further preferably 98% or more identical to the base sequence as set forth in SEQ ID NO: 1, particularly preferably 99% or more identical to the base sequence as set forth in SEQ ID NO: 1.

Specifically, the mutated GLIS1 gene having a sequence identity of 85% or more to the base sequence as set forth in SEQ ID NO: 1 may have deletion, substitution, insertion, or addition of 194 or less bases to the base sequence as set forth in SEQ ID NO: 1.

The mutated GLIS1 gene having a sequence identity of 90% or more to the base sequence as set forth in SEQ ID NO: 1 may have deletion, substitution, insertion, or addition of 129 or less bases to the base sequence as set forth in SEQ ID NO: 1.

The mutated GLIS1 gene having a sequence identity of 95% or more to the base sequence as set forth in SEQ ID NO: 1 may have deletion, substitution, insertion, or addition of 65 or less bases to the base sequence as set forth in SEQ ID NO: 1.

The mutated GLIS1 gene having a sequence identity of 98% or more to the base sequence as set forth in SEQ ID NO: 1 may have deletion, substitution, insertion, or addition of 26 or less bases to the base sequence as set forth in SEQ ID NO: 1.

The mutated GLIS1 gene having a sequence identity of 99% or more to the base sequence as set forth in SEQ ID NO: 1 may have deletion, substitution, insertion, or addition of 13 or less bases to the base sequence as set forth in SEQ ID NO: 1.

Among them, the mutated GLIS1 gene having a sequence identity of 85% or more to the base sequence as set forth in SEQ ID NO: 1 or one or more gene products thereof is particularly preferably a mutated GLIS1 gene comprising the nucleotide sequence as set forth in SEQ ID NO: 1 or having an additional mutation to the base sequence as set forth in SEQ ID NO: 1 or one or more gene products thereof, where the mutation is at least one of (i) and (ii) below:
  (i) addition of any base or bases to a 5'-terminus of the mutated GLIS1 gene having the base sequence as set forth in SEQ ID NO: 1; and
  (ii) addition of any base or bases to a 3'-terminus of the mutated GLIS1 gene having the base sequence as set forth in SEQ ID NO: 1.

The mutated GLIS1 gene having a sequence identity of 85% or more to the base sequence as set forth in SEQ ID NO: 1 in the (i) means that 194 or less any bases can be added to the 5'-terminus of the mutated GLIS1 gene having the base sequence as set forth in SEQ ID NO: 1.

Such addition to the mutated GLIS1 gene having a sequence identity of 85% or more to the base sequence as set forth in SEQ ID NO: 1 in the (i) may be or may not be such a mutation that adds an amino acid residue or amino acid residues to the N-terminus of a mutated GLIS1 protein coded for by the mutated GLIS1 gene consisting of the mutated GLIS1 gene having the base sequence as set forth in SEQ ID NO: 1.

The mutated GLIS1 gene having a sequence identity of 85% or more to the base sequence as set forth in SEQ ID NO: 1 in the (ii) means that 194 or less any bases can be added to the 3'-terminus of the mutated GLIS1 gene having the base sequence as set forth in SEQ ID NO: 1.

Such addition to the mutated GLIS1 gene having a sequence identity of 85% or more to the base sequence as set forth in SEQ ID NO: 1 in the (ii) may be or may not be such a mutation that adds an amino acid residue or amino acid residues to the C-terminus of a mutated GLIS1 protein coded for by the mutated GLIS1 gene consisting of the mutated GLIS1 gene having the base sequence as set forth in SEQ ID NO: 1.

The mutated GLIS1 gene consisting of the base sequence as set forth in SEQ ID NO: 2 refers to a sequence of a gene coding for a protein in which 190 amino acid residues at N-terminus of a human GLIS1 protein are deleted.

The sequence identity of the mutated GLIS1 gene having a sequence identity of 85% or more to the base sequence as set forth in SEQ ID NO: 2 is not particularly limited and may be appropriately selected depending on the intended purpose, so long as it is 85% or more to the base sequence as set forth in SEQ ID NO: 2. However, it is preferably 90% or more identical to the base sequence as set forth in SEQ ID NO: 2, more preferably 95% or more identical to the base sequence as set forth in SEQ ID NO: 2, further preferably 98% or more identical to the base sequence as set forth in SEQ ID NO: 2, particularly preferably 99% or more identical to the base sequence as set forth in SEQ ID NO: 2.

Specifically, the mutated GLIS1 gene having a sequence identity of 85% or more to the base sequence as set forth in SEQ ID NO: 2 may have deletion, substitution, insertion, or addition of 195 or less bases to the base sequence as set forth in SEQ ID NO: 2.

The mutated GLIS1 gene having a sequence identity of 90% or more to the base sequence as set forth in SEQ ID NO: 2 may have deletion, substitution, insertion, or addition of 130 or less bases to the base sequence as set forth in SEQ ID NO: 2.

The mutated GLIS1 gene having a sequence identity of 95% or more to the base sequence as set forth in SEQ ID NO: 2 may have deletion, substitution, insertion, or addition of 65 or less bases to the base sequence as set forth in SEQ ID NO: 2.

The mutated GLIS1 gene having a sequence identity of 98% or more to the base sequence as set forth in SEQ ID NO: 2 may have deletion, substitution, insertion, or addition of 26 or less bases to the base sequence as set forth in SEQ ID NO: 2.

The mutated GLIS1 gene having a sequence identity of 99% or more to the base sequence as set forth in SEQ ID NO: 2 may have deletion, substitution, insertion, or addition of 13 or less bases to the base sequence as set forth in SEQ ID NO: 2.

Among them, the mutated GLIS1 gene having a sequence identity of 85% or more to the base sequence as set forth in SEQ ID NO: 2 or one or more gene products thereof is particularly preferably a mutated GLIS1 gene comprising the nucleotide sequence as set forth in SEO ID NO: 2 or having an additional mutation to the base sequence as set forth in SEQ ID NO: 2 or one or more gene products thereof, where the mutation is at least one of (i) and (ii) below:
  (i) addition of any base or bases to a 5'-terminus of the mutated GLIS1 gene having the base sequence as set forth in SEQ ID NO: 2; and (ii) addition of any base or bases to a 3'-terminus of the mutated GLIS1 gene having the base sequence as set forth in SEQ ID NO: 2.

The mutated GLIS1 gene having a sequence identity of 85% or more to the base sequence as set forth in SEQ ID NO: 2 in the (i) means that 195 or less any bases can be added to the 5'-terminus of the base sequence as set forth in SEQ ID NO: 2.

Such addition to the mutated GLIS1 gene having the base sequence as set forth in SEQ ID NO: 2 in the (i) may be or may not be such a mutation that adds an amino acid residue or amino acid residues to the N-terminus of a mutated GLIS1 protein coded for by the mutated GLIS1 gene consisting of the base sequence as set forth in SEQ ID NO: 2.

The mutated GLIS1 gene having a sequence identity of 85% or more to the base sequence as set forth in SEQ ID NO: 2 in the (ii) means that 195 or less any bases can be added to the 3-terminus of the mutated GLIS1 gene having the base sequence as set forth in SEQ ID NO: 2.

Such addition to the mutated GLIS1 gene having the base sequence as set forth in SEQ ID NO: 2 in the (ii) may be or may not be such a mutation that adds an amino acid residue or amino acid residues to the C-terminus of a mutated GLIS1 protein coded for by the mutated GLIS1 gene consisting of the mutated GLIS1 gene having the base sequence as set forth in SEQ ID NO: 2.

A method for determining the sequence identity is not particularly limited and may be appropriately selected from methods known in the art. For example, the sequence identity can be determined using the algorithm BLAST by Karlin and Altscul (Karlin, S. & Altschul, S. F. (1990) Proc. Natl. Acad. Sci. USA 87: 2264-2268, Karlin, S. & Altschul. S. F., Proc. Natl. Acad. Sci. USA 90: 5873).

—Neurogenin3 Gene or One or More Gene Products Thereof—

A source of the Neurogenin3 gene is not particularly limited and may be appropriately selected depending on the intended purpose. Examples thereof include human and mouse.

Sequence information of the Neurogenin3 gene is available from known databases. For example, the sequence information is available from NCBI under Accession numbers of NM_009719 (mouse) and NM_020999 (human).

—Pdx1 Gene or One or More Gene Products Thereof—

A source of the Pdx1 gene is not particularly limited and may be appropriately selected depending on the intended purpose. Examples thereof include human and mouse.

Sequence information of the Pdx1 gene is available from known databases. For example, the sequence information is available from NCBI under Accession numbers of NM_000209 (human) and NM_008814 (mouse).

—MafA Gene or One or More Gene Products Thereof—

A source of the MafA gene is not particularly limited and may be appropriately selected depending on the intended purpose. Examples thereof include human and mouse.

Sequence information of the MafA gene is available from known databases. For example, the sequence information is available from NCBI under Accession numbers of NM_201589 (human) and NM_194350 (mouse).

—Other Genes or One or More Gene Products Thereof—

The other genes or one or more gene products thereof are not particularly limited and may be appropriately selected depending on the intended purpose, so long as they do not impair effects of the present invention.

Each of sequences of the GLIS1 gene, the mutated GLIS1 gene, the Neurogenin3 gene, the Pdx1 gene, the MafA gene, and the other genes may consist of a sequence of a protein-coding region in the sequence of each of the genes, or may include other regions than the protein-coding region.

The GLIS1 gene or one or more gene products thereof, the Neurogenin3 gene or one or more gene products thereof, the Pdx1 gene or one or more gene products thereof, the MafA gene or one or more gene products thereof, and the other genes or one or more gene products thereof may have a mutation, so long as they do not impair effects of the present invention.

Examples of the mutation include mutations that do not change an amino acid sequence of a protein from each of the genes and mutations in which one or several (2 to 5) amino acids are deleted, substituted, inserted, or added in an amino acid sequence of a protein from each of the genes.

In the case where the GLIS1 gene or one or more gene products thereof, the Neurogenin3 gene or one or more gene products thereof, the Pdx1 gene or one or more gene products thereof, the MafA gene or one or more gene products thereof, and the other genes or one or more gene products thereof has a mutation, a sequence identity to each of corresponding wild-type genes or one or more gene products thereof is not particularly limited and may be appropriately selected depending on the intended purpose, so long as they do not impair effects of the present invention. However, it is preferably 70% or more, more preferably 80% or more, particularly preferably 90% or more in a base sequence of a region to be translated into a protein.

<<Somatic Cells>>

The somatic cells are not particularly limited and may be appropriately selected depending on the intended purpose. The somatic cells may be undifferentiated precursor cells or terminally differentiated mature cells.

The somatic cells may be derived from ES cells or iPS cells.

Specific examples of the somatic cells include adipose tissue-derived interstitial (stem) cells, neural stem cells, hematopoietic stem cells, mesenchymal stem cells, fibroblasts, hepatic cells, epithelial cells, renal cells, macrophages, lymphocytes, muscle cells, nerve cells, and neuroglia cells. Among them, fibroblasts, mesenchymal stem cells, hepatic cells, epithelial cells, and renal cells are preferable, and fibroblasts and mesenchymal stem cells are more preferable.

A species of an individual from which the somatic cells are harvested is not particularly limited and may be appropriately selected depending on the intended purpose. Examples thereof include human and mouse.

The individual from which the somatic cells are harvested is not particularly limited and may be appropriately selected depending on the intended purpose. In the case where the resultant pancreatic endocrine cells are used for regenerative therapies, the individual is preferably the individual oneself or other individuals having the same or substantially the same MHC type as that of the individual, in terms of a rejection reaction. The phrase "substantially the same MHC type" means, as used herein, that the MHC type is compatible to the extent that, when pancreatic endocrine cells derived from the somatic cells are transplanted into an individual, transplanted cells are capable of being engrafted with the use of, for example, an immunosuppressive agent.

A time when the somatic cells are harvested from the individual is not particularly limited and may be appropriately selected depending on the intended purpose.

A condition under which the somatic cells are cultured is not particularly limited and may be appropriately selected depending on the intended purpose. Examples thereof include a culturing temperature of about 37° C. and a $CO_2$ concentration of from about 2% to about 5%.

A medium in which the somatic cells are cultured is not particularly limited and may be appropriately selected depending on the intended purpose. Examples thereof include minimum essential media (hereinafter may be referred to as "MEM"), Dulbecco's modified Eagle media (hereinafter may be referred to as "DMEM"), RPMI1640 media, 199 media, and F12 media, all of which contain from 5% by mass to 20% by mass of serum.

Introduction Method

A method for introducing each of the genes or one or more gene products thereof into the somatic cells is not particularly limited and may be appropriately selected depending on the intended purpose. For example, vectors, synthetic mRNA (messenger RNA), or recombinant proteins may be used.

——Vector——

The vector is not particularly limited and may be appropriately selected depending on the intended purpose. Examples thereof include viral vectors and non-viral vectors.

Specific examples of the viral vectors include retroviral vectors, lentiviral vectors, and Sendai virus vectors.

Specific examples of the non-viral vectors include plasmid vectors and episomal vectors.

A method for introducing the vector into the somatic cells is not particularly limited and may be appropriately selected from known methods in the art depending on the intended purpose.

In the case where the retroviral vectors are used, the methods described in, for example, WO 2007/69666; Cell, 126, 663-676 (2006); or Cell, 131, 861-872 (2007) may be used. In the case where the lentiviral vectors are used, the methods described in, for example, Science, 318, 1917-1920 (2007) may be used. In the case where the Sendai virus vectors are used, the methods described in, for example, International Publication No. WO2016/114405 and JP-A No. 2021-006032 may be used.

In the case where the plasmid vectors are used, the methods described in, for example, Science, 322, 949-953 (2008) may be used. In the case where the episomal vectors are used, the methods described in, for example, Science, 324: 797-801 (2009) or Biochemical and Biophysical Research Communications, 426: 141-147 (2012) may be used.

In the case where the viral vectors are used, viral particles obtained using packaging cells may be used.

The packaging cells are cells into which viral structural protein-coding genes have been introduced. When a recombinant viral vector into which a target gene has been incorporated is introduced into the packaging cells, recombinant viral particles into which the target gene has been incorporated are produced.

The packaging cells are not particularly limited and may be appropriately selected depending on the intended purpose. Examples thereof include packaging cells based on human kidney-derived HEK293 cells or mouse fibroblast-derived NIH3T3 cells; packaging cells Platinum-E (hereinafter may be referred to as "Plat-E cells") which are capable of producing high titer viruses for a long period of time and in which viral structural proteins gag-pol and env are expressed under the control of MoMuLV (Moloney Murine Leukemia Virus) LTR (long terminal repeats); PLAT-A cells that are designed to express Amphotropic virus-derived envelope glycoproteins; and PLAT-GP cells that are designed to express vesicular stomatitis virus-derived envelope glycoproteins.

A method for introducing the viral vector into the packaging cells is not particularly limited and may be appropriately selected depending on the intended purpose. Examples thereof include lipofection methods, electroporation methods, and calcium phosphate methods.

A method for infecting the somatic cells with the resultant viral particles is not particularly limited and may be appropriately selected depending on the intended purpose. Examples thereof include polybrene methods.

The vector may include a marker gene for verifying whether each of the genes has been successfully introduced.

The marker gene refers to a gene that allows for cell sorting or cell selection by introducing the marker gene into a cell. Specific examples of the marker gene include drug resistant genes, fluorescent protein genes, luminescent enzyme genes, and coloring enzyme genes. These may be used alone or in combination.

Specific examples of the drug resistant genes include neomycin resistant genes, tetracycline resistant genes, kanamycin resistant genes, zeocin resistant genes, and hygromycin resistant genes.

Specific examples of the fluorescent protein genes include green fluorescent protein (GFP) genes, yellow fluorescent protein (YFP) genes, and red fluorescent protein (RFP) genes.

Specific examples of the luminescent enzyme gene include luciferase genes.

Specific examples of the coloring enzyme genes include β galactosidase genes, β glucuronidase genes, and alkaline phosphatase genes.

In methods for introducing each of the genes into the somatic cells using the vector, one gene may be incorporated into one vector, or two or more genes may be incorporated into one vector. By incorporating two or more genes into one vector, the two or more genes may be expressed at the same time (hereinafter may be referred to as "co-expression").

A method for incorporating two or more genes into one vector is not particularly limited and may be appropriately selected depending on the intended purpose. However, the two or more genes are preferably incorporated via a linkage sequence.

The linkage sequence is not particularly limited and may be appropriately selected depending on the intended purpose. Examples thereof include gene sequences coding for a foot and mouth disease virus (Picornaviridae Aphthovirus)-derived 2A peptide and IRESs (internal ribosome entry sites).

A method for introducing the mRNA into the somatic cells is not particularly limited and may be appropriately selected from known methods in the art.

A method for introducing the recombinant protein into the somatic cells is not particularly limited and may be appropriately selected from known methods in the art.

The number of times of introduction of each of the genes or one or more gene products thereof into the somatic cells is not particularly limited and may be appropriately selected depending on the intended purpose. For example, each of the genes or one or more gene products thereof may be introduced once or two or more times.

A time when each of the genes or one or more gene products thereof are introduced into the somatic cells is not particularly limited and may be appropriately selected depending on the intended purpose. All the genes or one or more gene products thereof may be introduced at the same time or at different times.

An amount of each of the genes or one or more gene products thereof to be introduced into the somatic cells is not particularly limited and may be appropriately selected depending on the intended purpose. All the genes or one or more gene products thereof may be introduced in an equal amount or different amounts.

For the genes or one or more gene products thereof, genes only, gene products only, or both of genes and gene products in the same gene or one or more gene products thereof may be used.

Moreover, when used in combination with different genes or one or more gene products thereof, the gene or one or more gene products thereof may be a combination of genes only in all the genes or one or more gene products thereof, a combination of gene products only in all the genes or one or more gene products thereof, or a combination of genes in some genes or one or more gene products thereof and gene products in other genes or one or more gene products thereof.

In the introduction step of the genes or one or more gene products thereof, other materials than the genes or one or more gene products thereof may be introduced, so long as they do not impair effects of the present invention.

Other Steps

The other steps are not particularly limited and may be appropriately selected depending on the intended purpose, so long as they do not impair effects of the present invention. Examples thereof include a genes or genes products thereof-introduced cells culturing step in which somatic cells, into which each of the genes or one or more gene products thereof has been introduced, are cultured.

—Genes or Genes Products Thereof—Introduced Cells Culturing Step—

The genes or genes products thereof-introduced cells culturing step is a step of culturing somatic cells into which each of the genes or one or more gene products thereof has been introduced.

A condition under which the genes or genes products thereof-introduced cells are cultured is not particularly limited and may be appropriately selected depending on the intended purpose. Examples thereof include a culturing temperature of about 37° C. and a $CO_2$ concentration of from about 2% to about 5%.

A medium used for culturing the genes or genes products thereof-introduced cells is not particularly limited and may be appropriately selected depending on the intended purpose. Examples thereof include MEM, DMEM, RPMI1640 media, 199 media, and F12 media, all of which contain from 5% by mass to 20% by mass of serum.

A period of time for which the genes or genes products thereof-introduced cells are cultured is not particularly limited and may be appropriately selected depending on the intended purpose.

An exchange frequency of the medium is not particularly limited and may be appropriately selected depending on the intended purpose. Examples thereof include every 2 days to 3 days.

<Pancreatic Endocrine Cells>

A method for verifying whether pancreatic endocrine cells are successfully produced by the method for producing pancreatic endocrine cells is not particularly limited and may be appropriately selected depending on the intended purpose. Examples thereof include a method by which expression of proteins to be expressed in the pancreatic endocrine cells is verified and a method by which expression of genes to be expressed in the pancreatic endocrine cells is verified.

For example, whether α cells of the pancreatic endocrine cells are produced is capable of being verified by the presence or absence of glucagon expression, whether β cells of the pancreatic endocrine cells are produced is capable of being verified by the presence or absence of insulin expression, and whether S cells of the pancreatic endocrine cells are produced is capable of being verified by the presence or absence of somatostatin expression.

The method by which expression of proteins is verified is not particularly limited and may be appropriately selected from known methods in the art. Examples thereof include immunostaining analyses.

The method by which expression of genes is verified is not particularly limited and may be appropriately selected from known methods in the art. Examples thereof include quantitative PCR analyses.

According to the method for producing pancreatic endocrine cells of the present invention, the pancreatic endocrine cells are capable of being produced from somatic cells through transdifferentiation. Therefore, the method is advantageous in that the pancreatic endocrine cells are capable of being produced without undergoing the iPS cell stage that have a risk of forming tumors.

Note that, the transdifferentiation refers to direct transformation from a cell type to another cell type without undergoing the stem cell stage.

The method for producing pancreatic endocrine cells of the present invention is simple and easily reproduced because a gene or one or more gene products thereof only have to be introduced into somatic cells, and at the same time the pancreatic endocrine cells are capable of being produced efficiently in a short period of time. Moreover, the method for producing pancreatic endocrine cells of the present invention is also advantageous in that the pancreatic endocrine cells are capable of being produced without using a special medium for which culturing environments are needed to be properly adjusted, for example, by adding a development inhibitor to the medium.

The pancreatic endocrine cells may be a cells, β cells, S cells, or mixtures thereof. Among them, β cells are preferable in terms of regenerative therapies for diabetes patients.

The pancreatic endocrine cells of the present invention are suitably available as pancreatic endocrine cells used for, for example, regenerative therapies or screening of diabetes drugs.

(Transdifferentiation Agent)

A transdifferentiation agent of the present invention is a transdifferentiation agent for transdifferentiating somatic cells into pancreatic endocrine cells. The transdifferentiation agent includes at least the gene or one or more gene products thereof (A), the gene or one or more gene products thereof (B), the gene or one or more gene products thereof (C), or the gene or one or more gene products thereof (D); and, if necessary further includes other components.

<Somatic Cells>

Somatic cells to be targeted by the transdifferentiation agent and preferable aspects thereof are the same as those described under the section entitled "Production method of pancreatic endocrine cells."

<Pancreatic Endocrine Cells>

Pancreatic endocrine cells obtained using the transdifferentiation agent and preferable aspects thereof are the same as those described under the section entitled "Production method of pancreatic endocrine cells."
<Gene or one or more gene products thereof>
—Aspect—

An aspect of the gene or one or more gene products thereof in the transdifferentiation agent is not particularly limited and may be appropriately selected depending on the intended purpose, so long as the gene or one or more gene products thereof (A), the gene or one or more gene products thereof (B), the gene or one or more gene products thereof (C), or the gene or one or more gene products thereof (D) is included. However, from the viewpoint of excellent production efficiency of the pancreatic endocrine cells, the gene or one or more gene products thereof (A), the gene or one or more gene products thereof (B), or the gene or one or more gene products thereof (D) is preferably included, and the gene or one or more gene products thereof (A) or the gene or one or more gene products thereof (D) is more preferably included.

The gene or one or more gene products thereof in the transdifferentiation agent may consist of the gene or one or more gene products thereof (A), the gene or one or more gene products thereof (B), the gene or one or more gene products thereof (C), or the gene or one or more gene products thereof (D), or may include other genes or one or more gene products thereof.
—GLIS1 Gene or One or More Gene Products Thereof—

The GLIS1 gene is the same as those described under the section entitled "Production method of pancreatic endocrine cells." The sequence of the GLIS1 gene is also the same as those described under the section entitled "Production method of pancreatic endocrine cells." The GLIS1 gene or one or more gene products thereof may have a mutation which is the same as those described under the section entitled "Production method of pancreatic endocrine cells."
—Mutated GLIS1 Gene or One or More Gene Products Thereof—

The mutated GLIS1 gene is the same as those described under the section entitled "Production method of pancreatic endocrine cells." The sequence of the mutated GLIS1 gene is also the same as those described under the section entitled "Production method of pancreatic endocrine cells."
—Neurogenin3 Gene or One or More Gene Products Thereof—

The Neurogenin3 gene is the same as those described under the section entitled "Production method of pancreatic endocrine cells." The sequence of the Neurogenin3 gene is also the same as those described under the section entitled "Production method of pancreatic endocrine cells." The Neurogenin3 gene or one or more gene products thereof may have a mutation which is the same as those described under the section entitled "Production method of pancreatic endocrine cells."
—Pdx1 Gene or One or More Gene Products Thereof—

The Pdx1 gene is the same as those described under the section entitled "Production method of pancreatic endocrine cells." The sequence of the Pdx1 gene is also the same as those described under the section entitled "Production method of pancreatic endocrine cells." The Pdx1 gene or one or more gene products thereof may have a mutation which is the same as those described under the section entitled "Production method of pancreatic endocrine cells."
—MafA Gene or One or More Gene Products Thereof—

The MafA gene is the same as those described under the section entitled "Production method of pancreatic endocrine cells." The sequence of the MafA gene is also the same as those described under the section entitled "Production method of pancreatic endocrine cells." The MafA gene or one or more gene products thereof may have a mutation which is the same as those described under the section entitled "Production method of pancreatic endocrine cells."
—Other Genes or One or More Gene Products Thereof—

The other genes are the same as those described under the section entitled "Production method of pancreatic endocrine cells." The sequences of the other genes are also the same as those described under the section entitled "Production method of pancreatic endocrine cells." The other genes or one or more gene products thereof may have a mutation which is the same as those described under the section entitled "Production method of pancreatic endocrine cells."

Each of the genes or one or more gene products thereof in the transdifferentiation agent may be incorporated into a vector, or may be a synthetic mRNA or a recombinant protein.

The vector may be the same as those described under the section entitled "Production method of pancreatic endocrine cells."

The synthetic mRNA and the recombinant protein may be produced by any of known methods in the art.

Other Components

The other components are not particularly limited and may be appropriately selected depending on the intended purpose, so long as they do not impair effects of the present invention.

The genes or one or more gene products thereof in the transdifferentiation agent may be divided into separate containers or may be placed in a single container. Alternatively, any number of the genes or one or more gene products thereof may be placed in each container.

An amount of each of the genes or one or more gene products thereof in the transdifferentiation agent is not particularly limited. All the genes or one or more gene products thereof may be included in an equal amount or different amounts.

The transdifferentiation agent may be suitably used as a component of a kit for producing pancreatic endocrine cells.

The kit for producing pancreatic endocrine cells includes at least the transdifferentiation agent; and, if necessary, further includes other components.

The other components in the kit for producing pancreatic endocrine cells are not particularly limited and may be appropriately selected depending on the intended purpose, so long as they do not impair effects of the present invention. Examples thereof include packaging cells and media.

The packaging cells and the media may be the same as those described under the section entitled "Production method of pancreatic endocrine cells."

EXAMPLES

The present invention will now be described with reference to Test Examples described below, but the present invention is not limited thereto in any way.

Test Example 1-1: Production of Pancreatic Endocrine Cells-1-1

<Preparation of Cells>
Dual-labeled-mouse embryonic fibroblasts (hereinafter may be referred to as "dMEF"), which were a kind of somatic cells, were prepared in the following manner.

—Production of Genetically Modified Mice in which Pancreatic Endocrine Precursor Cells are Fluorescently Labeled with GFP—

Genetically modified mice in which pancreatic endocrine precursor cells are fluorescently labeled with GFP (mice expressing EGFP under the control of an Ngn3 gene promoter (Ngn3-eGFP)) were produced in the following manner.

A construct, in which a fusion protein gene of GFP and a nuclear localization signal (hereinafter may be referred to as "nls") was ligated downstream of the Ngn3 gene promoter (5 kb) isolated from a BAC clone, was microinjected into about 400 fertilized eggs to thereby produce genetically modified mice in which pancreatic endocrine precursor cells are fluorescently labeled with GFP.

—Production of Genetically Modified Mice in which Pancreatic β Cells are Fluorescently Labeled with DsRed2—

Genetically modified mice in which pancreatic β cells are fluorescently labeled with DsRed2 (mice expressing DsRed2 under the control of a rat insulin promoter (Ins-DsR)) were produced in the following manner.

A construct, in which a DsRed2 gene was ligated downstream of the rat insulin promoter (800 bp), was microinjected into about 400 fertilized eggs to thereby produce genetically modified mice in which pancreatic β cells are fluorescently labeled with DsRed2.

—Production of Dual—Labeled-Mouse Embryonic Fibroblasts—

The genetically modified mice in which pancreatic endocrine precursor cells are fluorescently labeled with GFP were crossed with the genetically modified mice in which pancreatic β cells are fluorescently labeled with DsRed2, and then male and female offspring mice (heterozygous) were crossed with each other to generate dual-labeled genetically modified mice (Ngn3·eGFP/Ins-DsR) that were confirmed to be homozygous by genomic southern blotting. Two pairs (male and female) of the homozygous dual-labeled genetically modified mice were crossed. At embryonic day 14.5, 16 embryos were removed from the uterus by a pair of forceps, and their blood was washed off with 10 mL of phosphate-buffered saline (containing 10 mg/mL kanamycin) in a 10 cm Petri dish within a clean bench. Then, the embryos were minced with a pair of scissors in 10 mL of DMEM (available from Sigma, #D5796; containing penicillin, streptomycin, and 10% FBS) in a 10 cm cell culture dish (available from TPP, #93150). The thus-minced embryonic tissue was transferred into a 15 mL tube and centrifuged at 1.4 krpm at room temperature for 4 min. The supernatant was discarded. The remaining pellet was added with and suspended in 1 mL of a 0.25% trypsin-containing EDTA solution (available from Wako Pure Chemical Industries, Ltd., #201-16945, containing 0.25% DNase I), and then incubated in a water bath at 37° C. The water bath was stirred by hand every 10 min. The minced embryonic tissue corresponding to one animal was well-suspended in 5 mL of DMEM (containing 10% FBS) in a 15 mL tube, transferred into 5 mL of DMEM in a 10 cm cell culture dish, and then incubated within an incubator with 5% $CO_2$ at 37° C. On the following day, the 10 mL DMEM (containing 10% FBS) was replaced with fresh medium and subsequently changed every 2 days. About 4 to about 5 days after, dMEFs in the confluent 10 cm culture dish were washed with 6 mL of phosphate-buffered saline (hereinafter may be referred to as "PBS"). One milliliter of a 0.25% trypsin-containing EDTA solution was added thereto, and incubated within an incubator with 5% $CO_2$ at 37° C. for 2 min. Then, the cells were confirmed to be peeled off. Ten milliliters of DMEM (containing 10% FBS) was added thereto and the cells were well-suspended. The dMEFs for one culture dish were seeded onto new five 10 cm culture dishes and further cultured. After 5 to 6 days of culturing, the dMEFs were confirmed to be grown confluent and washed with 6 mL of PBS. One milliliter of a 0.25% trypsin/EDTA solution was added thereto, and incubated within an incubator with 5% $CO_2$ at 37° C. for 2 min. Then, the cells were confirmed to be peeled off. Six milliliters of DMEM (containing 10% FBS) was added thereto and the cells were well-suspended. The resultant suspension liquid was transferred into a 50 mL tube and centrifuged at 1.4 krpm at room temperature for 4 min. Then, the supernatant was discarded. The remaining cell pellet was added with and suspended in 10 mL of CELLBANKER (available from Takara Bio Inc., #CB011). The resultant suspension liquid was dispensed into vial tubes (0.5 mL per tube) and stored in a deep freezer at −145° C.

<Production of Retrovirus>

Plat-E cells in which viral structural proteins gag-pol and env, which were capable of producing high titer viruses for a long period of time, were expressed under the control of MoMuLV LTR and a plasmid DNA (pMX vector or pMX-puro vector) were used to produce a retrovirus in the following manner (Onishi. M., et. al., Exp. Hematol. 24, 324-329, 1996).

—Preparation of Plasmid DNA—

[pMX-GFP Vector]

A pMX-GFP vector is a vector in which a gene coding for a full-length GFP protein is inserted into a multi-cloning site of a pMX vector and a pMXpuro vector (obtained from The Institute of Medical Science, The University of Tokyo). Note that, the sequence of the gene coding for a full-length GFP protein is deposited in NCBI under Accession number L29345.

[pMX-Mouse GLIS1 Vector]

Figure 15:
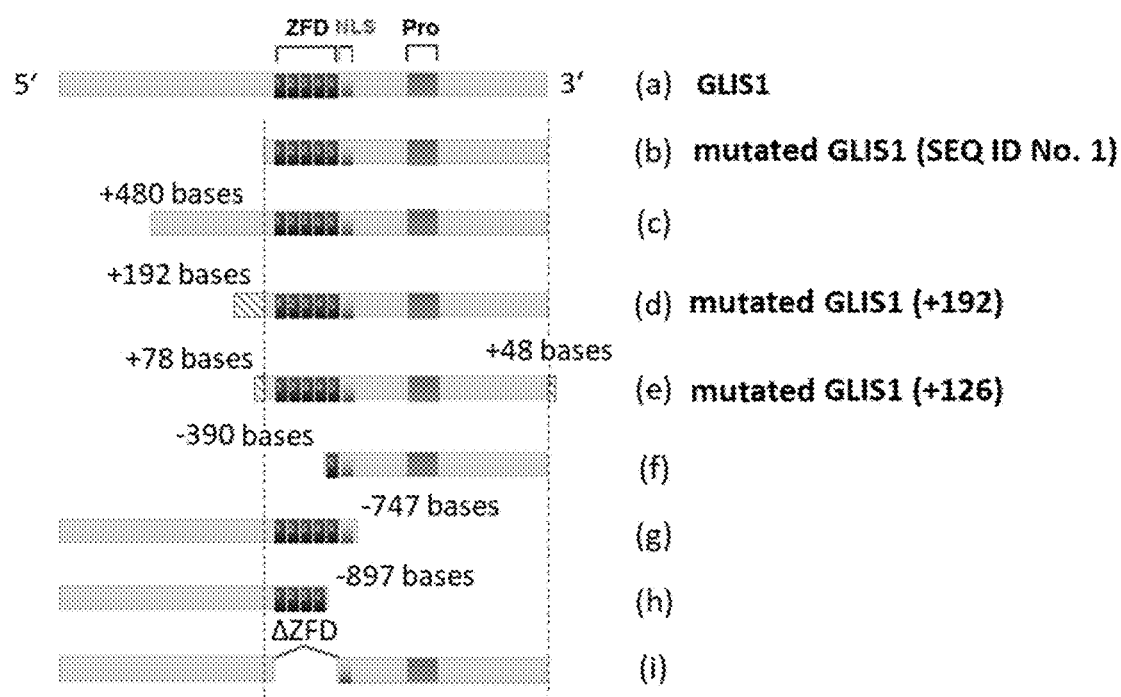
FIG. 15 is a schematic explanatory view of constructs produced in Test Example 1-1, Test Example 2-1, Test Example15-1, and Test Example 15-2. (a) indicates mouse GLIS1 (Accession number NM_147221), (b) indicates mouse mutated GLIS1 as set forth in SEQ ID NO: 1, (c) indicates a base sequence as set forth in SEQ ID NO: 20 (mouse mutated GLIS1 (−600)), (d) indicates a base sequence as set forth in SEQ ID NO: 12 (mouse mutated GLIS1 (+192)), (e) indicates a base sequence as set forth in SEQ ID NO: 17 (mouse mutated GLIS1 (+126)), (f) indicates a base sequence as set forth in SEQ ID NO: 23 (mouse GLIS1 (−1,470)), (g) indicates a base sequence as set forth in SEQ ID NO: 26 (mouse GLIS1 (−747)), (h) indicates a base sequence as set forth in SEQ ID NO: 29 (mouse GLIS1 (−897)), and (i) indicates a base sequence as set forth in SEQ ID NO: 33_(mouse GLIS1ΔZFD).

A pMX-mouse GLIS1 vector is a vector in which a gene coding for a full-length mouse GLIS1 protein is inserted into a multi-cloning site of a pMX vector (available from Addgene). Note that, the sequence of the gene coding for a full-length mouse GLIS1 protein is deposited in NCBI under Accession number NM_147221. A schematic explanatory view of the base sequence of Accession number NM_147221 is presented in (a) of FIG. 15.

[pMX-Mouse Neurogenin3 Vector]

A pMX-mouse Neurogenin3 vector is a vector in which a gene coding for a full-length mouse Neurogenin3 protein is inserted into a multi-cloning site of a pMX vector (obtained from The Institute of Medical Science, The University of Tokyo). Note that, the sequence of the gene coding for a full-length mouse Neurogenin3 protein is deposited in NCBI under Accession number NM_009719.

[pMX-Mouse Pdx1 Vector]

A pMX-mouse Pdx1 vector is a vector in which a gene coding for a full-length mouse Pdx1 protein is inserted into a multi-cloning site of a pMX vector (obtained from The Institute of Medical Science, The University of Tokyo). Note that, the sequence of the gene coding for a full-length mouse Pdx1 protein is deposited in NCBI under Accession number NM_008814.

[pMX-Mouse MafA Vector]

A pMX-mouse MafA vector is a vector in which a gene coding for a full-length mouse MafA protein is inserted into a multi-cloning site of a pMX vector (obtained from The Institute of Medical Science, The University of Tokyo). Note that, the sequence of the gene coding for a full-length mouse MafA protein is deposited in NCBI under Accession number NM_194350.

—Production of Retrovirus—

The Plat-E cells were seeded in a 6-well plate (available from TPP, 92406), which had been coated (for 1 hour at 37° C. and 5% CO) with Poly-L-Lysine (available from Sigma, P8920) diluted 10 fold with PBS, at $8 \times 10^5$ cells per well, and cultured overnight.

On the following day, 4 sg of the plasmid DNA was placed into a 1.5 mL tube containing 250 μL of OPTI-MEM (registered trademark) (available from Life Technologies Corporation, 11058021), mixed by tapping, and left to stand at room temperature for 5 min (hereinafter may be referred to as "plasmid/OPTI-MEM solution"). Meanwhile, 10 μL of LIPOFECTAMINE (registered trademark) 2000 (LP2000) (available from Life Technologies Corporation, 11668500) was placed into another 1.5 mL tube containing 250 μL of OPTI-MEM, mixed together, and left to stand at room temperature for 5 min (hereinafter may be referred to as "LP2000/OPTI-MEM solution"). The plasmid/OPTI-MEM solution and the LP2000/OPTI-MEM solution were well-mixed together and left to stand at room temperature for 20 min (hereinafter may be referred to as "plasmid/LP2000/OPTI-MEM mixed solution").

The plasmid/LP2000/OPTI-MEM mixed solution in which liposome-DNA complexes had been formed was added to one well in the 6-well plate, in which the Plat-E cells seeded the previous day had been cultured, to thereby transfect the cells. After mixing, the cells were cultured within an incubator with 5% $CO_2$ at 37° C. overnight. Twenty-four hours after, the medium was replaced, 1.5 mL of fresh DMEM (containing 10% FBS) was added thereto, and further cultured for 24 hours.

Forty-eight hours after the transfection, the culture supernatant containing viral particles was collected in a 2.5 mL syringe (available from Terumo Corporation, SS-02SZ) and filtered through a 0.45 filter (available from Whatman, PURADISC FP30 (CA-S 0.45 μm), 10462100) to thereby remove the Plat-E cells. The culture supernatant containing viral particles were transferred into a 2.0 mL tube.

Thus, a pMX-GFP vector-derived viral solution, a pMX-mouse GLIS1 vector-derived viral solution, a pMX-mouse Neurogenin3 vector-derived viral solution, a pMX-mouse Pdx1 vector-derived viral solution, and a pMX-mouse MafA vector-derived viral solution were obtained.

INTRODUCTION

The dMEFs were infected with the retrovirus to thereby introduce the gene(s) into the cells. The infection was performed in the following manner.

The dMEFs were seeded in a 24-well plate at $2.5 \times 10^4$ cells per well.

On the following day, an 8 mg/mL polybrene solution (available from Sigma, 107689) was added to the viral solution at a final concentration of 8 μg/mL. The culture supernatant of the dMEFs was removed through aspiration, and then each of the below-described viral solutions was added to a 24-well plate at 200 μL per well. Note that, amounts of the viral solutions were adjusted so as to be uniform for each well with a DMEM (containing 10% FBS) solution containing 8 μg/mL polybrene. After the addition of the viral solutions, the resultant solutions were incubated within an incubator with 5% $CO_2$ at 37° C. During the incubation, the media were changed every 2 or 3 days.

[Viral Solution]
(1) pMX-GFP vector-derived viral solution (control)
(2) pMX-mouse GLIS1 vector-derived viral solution, pMX-mouse Neurogenin3 vector-derived viral solution, and pMX-mouse Pdx1 vector-derived viral solution
(3) pMX-mouse GLIS1 vector-derived viral solution, pMX-mouse Neurogenin3 vector-derived viral solution, and pMX-mouse MafA vector-derived viral solution
(4) pMX-mouse GLIS1 vector-derived viral solution, pMX-mouse Neurogenin3 vector-derived viral solution, pMX-mouse Pdx1 vector-derived viral solution, and pMX-mouse MafA vector-derived viral solution <Determination of Number of dMEF-Derived Insulin Producing Cells>

After the introduction and 22 days of culturing, DsRed2-positive insulin producing cells were photographed by a fluorescence microscope (CARL ZEISS AXIOVERT 200M) unit.

A statistical analysis was performed in the following manner.

HOECHST 33342 (available from Life Technologies Corporation, H1399) was added to wells of a cell culture multi-well plate at a final concentration of 0.1 sg/mL and incubated within an incubator with 5% $CO_2$ at 37° C. for 30 min or longer. Then, images were taken in 100 fields of view for each well using a high-end cell imaging apparatus (available from Thermo Fisher Scientific Inc., ARRAY-SCAN XTI) with a 10× objective lens. The number of the DsRed2-positive insulin producing cells relative to the number of total cells was determined in the 100 fields of view. The results are presented in FIG. 1A.

In FIG. 1A, "CTL" represents the result in the case of using the (1) pMX-GFP vector-derived viral solution (control), "GNP" represents the result in the case of using the (2) pMX-mouse GLIS1 vector-derived viral solution, pMX-mouse Neurogenin3 vector-derived viral solution, and pMX-mouse Pdx1 vector-derived viral solution, "GNM" represents the result in the case of using the (3) pMX-mouse GLIS1 vector-derived viral solution, pMX-mouse Neurogenin3 vector-derived viral solution, and pMX-mouse MafA vector-derived viral solution, and "GNPM" represents the result in the case of using the (4) pMX-mouse GLIS1 vector-derived viral solution, pMX-mouse Neurogenin3 vector-derived viral solution, pMX-mouse Pdx1 vector-derived viral solution, and pMX-mouse MafA vector-derived viral solution.

It was demonstrated from the results of FIG. 1A that production efficiency of the pancreatic endocrine cells was significantly improved in the case where four factors, i.e., the GLIS1, the Neurogenin3, the Pdx1, and the MafA were used, which was one aspect of the method of the present invention.

<Quantitative PCR Analysis>

A quantitative PCR analysis was performed as described below using the cells, which had been subjected to the introduction and cultured for 24 days, to thereby determine a relative expression level of an insulin gene relative to that of a GAPDH gene.

The cells were suspended in a cell lysis solution, and subjected to RNA preparation and cDNA synthesis using SUPERPREP™ Cell Lysis & RT Kit for qPCR (available from TOYOBO CO., LTD., #SCQ-101) or SV 96 Total RNA Isolation System (available from Promega, #Z3505), REVERTRAACE qPCR RT Master Mix with gDNA Remover (available from TOYOBO CO., LTD., #FSQ-301) and then to the quantitative PCR analysis using GENEACE SYBR qPCR Mixα (available from NIPPON GENE CO., LTD.) by means of LIGHT CYCLER 480 (available from Roche). Note that, the following primers were used for the quantitative PCR analysis.

—Mouse GAPDH Gene—
Forward: 5'-tggagaaacctgccaagtatg-3' (SEQ ID NO: 3)
Reverse: 5'-ggagacaacctggtcctcag-3' (SEQ ID NO: 4)
—Mouse Insulin2 Gene—
Forward: 5'-tttgtcaagcagcacctttg-3' (SEQ ID NO: 5)
Reverse: 5'-ggtctgaaggtcacctgetc-3' (SEQ ID NO: 6)

Figure 1B:
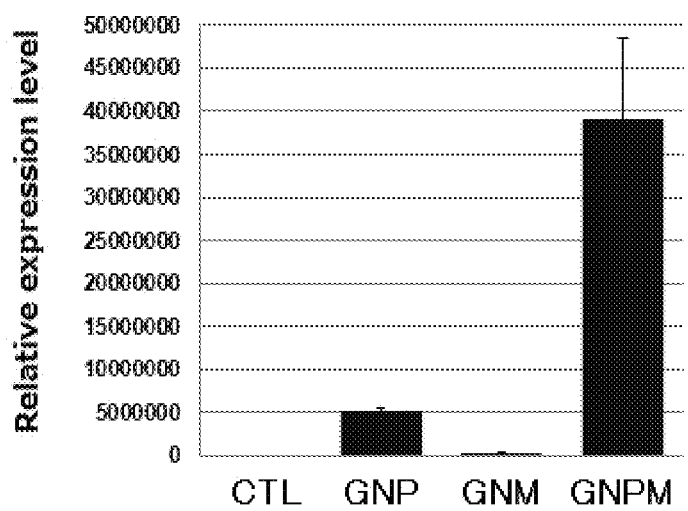
FIG. 1B is a graph illustrating the measurement results of a relative expression level of an insulin gene in Test Example 1-1.

The results of the quantitative PCR analysis are presented in FIG. 1B. In FIG. 1B, "CTL" represents the result in the case of using the (1) pMX-GFP vector-derived viral solution (control), "GNP" represents the result in the case of using the (2) pMX-mouse GLIS1 vector-derived viral solution, pMX-mouse Neurogenin3 vector-derived viral solution, and pMX-mouse Pdx1 vector-derived viral solution, "GNM" represents the result in the case of using the (3) pMX-mouse GLIS1 vector-derived viral solution, pMX-mouse Neurogenin3 vector-derived viral solution, and pMX-mouse MafA vector-derived viral solution, and "GNPM" represents the result in the case of using the (4) pMX-mouse GLIS1 vector-derived viral solution, pMX-mouse Neurogenin3 vector-derived viral solution, pMX-mouse Pdx1 vector-derived viral solution, and pMX-mouse MafA vector-derived viral solution.

It was demonstrated from the results of FIG. 1B that an expression level of the insulin gene was also increased in the case where four factors, i.e., the GLIS1, the Neurogenin3, the Pdx1, and the MafA were used, which was one aspect of the method of the present invention. This also indicates that the production efficiency of the pancreatic endocrine cells was significantly improved.

Test Example 1-2: Production of Pancreatic Endocrine Cells-1-2

<Preparation of Cells>
The dMEFs were prepared in the same manner as in the Test Example 1-1.
<Production of Retrovirus>
Plat-GP cells in which viral structural proteins gag-pol and env, which were capable of producing high titer viruses for a long period of time, were expressed under the control of MoMuLV LTR and a plasmid DNA (pMX vector or pMX-puro vector, VSVG vector) were used to produce a retrovirus in the following manner (Onishi, M., et. al., Exp. Hematol. 24, 324-329, 1996).
—Preparation of Plasmid DNA—
[pMX-GFP Vector]
The pMX-GFP vector was prepared in the same manner as in the Test Example 1-1

[pMX-Human GLIS1 Vector]
A pMX-human GLIS1 vector is a vector in which a gene coding for a full-length pMX-human GLIS1 protein is inserted into a multi-cloning site of a pMX vector (available from Addgene). Note that, the sequence of the gene coding for a full-length pMX-human GLIS1 protein is deposited in NCBI under Accession number NM_147193.
[pMX-Human Neurogenin3 Vector]
A pMX-human Neurogenin3 vector is a vector in which a gene coding for a full-length human Neurogenin3 protein is inserted into a multi-cloning site of a pMX vector (obtained from The Institute of Medical Science, The University of Tokyo). Note that, the sequence of the gene coding for a full-length human Neurogenin3 protein is deposited in NCBI under Accession number NM_020999.
[pMX-Human Pdx1 Vector]
A pMX-human Pdx1 vector is a vector in which a gene coding for a full-length human Pdx1 protein is inserted into a multi-cloning site of a pMX vector (obtained from The Institute of Medical Science, The University of Tokyo). Note that, the sequence of the gene coding for a full-length human Pdx1 protein is deposited in NCBI under Accession number NM_000209.
[pMX-Human MafA Vector]
A pMX-human MafA vector is a vector in which a gene coding for a full-length human MafA protein is inserted into a multi-cloning site of a pMX vector (obtained from The Institute of Medical Science, The University of Tokyo). Note that, the sequence of the gene coding for a full-length human MafA protein is deposited in NCBI under Accession number NM_201589.
—Production of Retrovirus—
The Plat-GP cells were seeded in a 6-well plate (available from TPP, 92406), which had been coated (for 1 hour at 37° C. and 5% $CO_2$) with Poly-L-Lysine (available from Sigma. P8920) diluted 10 fold with PBS, at $8 \times 10^5$ cells per well, and cultured overnight.

On the following day, 4 sg of the plasmid DNA (2 g of the pMX vector and 2 sg of the VSVG vector) was placed into a 1.5 mL tube containing 250 μL of OPTI-MEM (registered trademark) (available from Life Technologies Corporation, 11058021), mixed by tapping, and left to stand at room temperature for 5 min (hereinafter may be referred to as "plasmid/OPTI-MEM solution"). Meanwhile, 10 μL of LIPOFECTAMINE (registered trademark) 2000 (LP2000) (available from Life Technologies Corporation, 11668500) was placed into another 1.5 mL tube containing 250 μL of OPTI-MEM, mixed together, and left to stand at room temperature for 5 min (hereinafter may be referred to as "LP2000/OPTI-MEM solution"). The plasmid/OPTI-MEM solution and the LP2000/OPTI-MEM solution were well-mixed together and left to stand at room temperature for 20 min (hereinafter may be referred to as "plasmid/LP2000/OPTI-MEM mixed solution").

The plasmid/LP2000/OPTI-MEM mixed solution in which liposome-DNA complexes had been formed was added to one well in the 6-well plate, in which the Plat-GP cells seeded the previous day had been cultured, to thereby transfect the cells. After mixing, the cells were cultured within an incubator with 5% $CO_2$ at 37° C. overnight. Twenty-four hours after, the medium was replaced, 1.5 mL of fresh DMEM (containing 10% FBS) was added thereto, and further cultured for 24 hours.

Forty-eight hours after the transfection, the culture supernatant containing viral particles was collected in a 2.5 mL syringe (available from Terumo Corporation, SS-02SZ) and filtered through a 0.45 filter (available from Whatman, PURADISC FP30 (CA-S 0.45 μm), 10462100) to thereby remove the Plat-GP cells. The culture supernatant containing viral particles were transferred into a 2.0 mL tube.

Thus, a pMX-GFP vector-derived viral solution, a pMX-human GLIS1 vector-derived viral solution, a pMX-human Neurogenin3 vector-derived viral solution, a pMX-human Pdx1 vector-derived viral solution, and pMX-human MafA vector-derived viral solution were obtained.

INTRODUCTION

The dMEFs were infected with the retrovirus to thereby introduce the gene(s) into the cells. The infection was performed in the following manner.

The dMEFs were seeded in a 24-well plate at 2.5×10⁴ cells per well.

On the following day, an 8 mg/mL polybrene solution (available from Sigma, 107689) was added to the viral solution at a final concentration of 8 sg/mL. The culture supernatant of the dMEFs was removed through aspiration, and then each of the below-described viral solutions was added to a 24-well plate at 200 μL per well. Note that, amounts of the viral solutions were adjusted so as to be uniform for each well with a DMEM (containing 10% FBS) solution containing 8 sg/mL polybrene. After the addition of the viral solutions, the resultant solutions were incubated within an incubator with 5% $CO_2$ at 37° C. During the incubation, the media were changed every 2 or 3 days.
[Viral Solution]
(1) pMX-GFP vector-derived viral solution (control)
(2) pMX-human GLIS1 vector-derived viral solution, pMX-human Neurogenin3 vector-derived viral solution, and pMX-human Pdx1 vector-derived viral solution
(3) pMX-human GLIS1 vector-derived viral solution, pMX-human Neurogenin3 vector-derived viral solution, and pMX-human MafA vector-derived viral solution
(4) pMX-human GLIS1 vector-derived viral solution, pMX-human Neurogenin3 vector-derived viral solution, pMX-human Pdx1 vector-derived viral solution, and pMX-human MafA vector-derived viral solution
<Quantitative PCR Analysis>

The quantitative PCR analysis was performed in the same manner as in the Test Example 1-1.

Figure 1C:
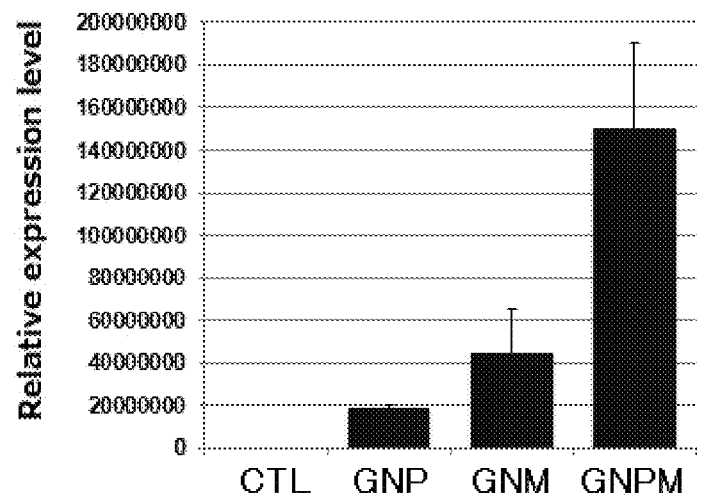
FIG. 1C is a graph illustrating the measurement results of a relative expression level of an insulin gene in Test Example 1-2.

The results of the quantitative PCR analysis are presented in FIG. 1C. In FIG. 1C, "CTL" represents the result in the case of using the (1) pMX-GFP vector-derived viral solution (control), "GNP" represents the result in the case of using the (2) pMX-human GLIS1 vector-derived viral solution, pMX-human Neurogenin3 vector-derived viral solution, and pMX-human Pdx1 vector-derived viral solution, "GNM" represents the result in the case of using the (3) pMX-human GLIS1 vector-derived viral solution, pMX-human Neurogenin3 vector-derived viral solution, and pMX-human MafA vector-derived viral solution, and "GNPM" represents the result in the case of using the (4) pMX-human GLIS1 vector-derived viral solution, pMX-human Neurogenin3 vector-derived viral solution, pMX-human Pdx1 vector-derived viral solution, and pMX-human MafA vector-derived viral solution.

It was demonstrated from the results of FIG. 1C that, when human genes were used, the expression level of the insulin gene was similarly increased and thus the production efficiency of the pancreatic endocrine cells was significantly improved in the case where four factors, i.e., the GLIS1, the Neurogenin3, the Pdx1, and the MafA were used, which was one aspect of the method of the present invention.

Test Example 2-1: Production of Pancreatic Endocrine Cells-2-1

<Preparation of Cells>
The dMEFs were prepared in the same manner as in the Test Example 1-1.
<Production of Retrovirus>
The Plat-E cells in which viral structural proteins gag-pol and env, which were capable of producing high titer viruses for a long period of time, were expressed under the control of MoMuLV LTR and a plasmid DNA (pMX vector or pMX-puro vector) were used to produce a retrovirus in the following manner (Onishi, M., et. al., Exp. Hematol. 24, 324-329, 1996).

—Preparation of Plasmid DNA—
[pMX-GFP Vector]
The pMX-GFP vector was prepared in the same manner as in the Test Example 1-1.
[pMX-Mouse GLIS1 Vector]
The pMX-mouse GLIS1 vector was prepared in the same manner as in the Test Example 1-1.
[pMX-Mouse Mutated GLIS1 Vector]
A pMX-mouse mutated GLIS1 vector is a vector in which a gene coding for a protein in which 360 amino acid residues at N-terminus of a mouse GLIS1 protein are deleted is inserted into a multi-cloning site of a pMX vector (available from Addgene).

A sequence of the gene coding for a protein in which 360 amino acid residues at N-terminus of a mouse GLIS1 protein are deleted is as set forth in SEQ ID NO: 1 and was prepared in the following manner. A schematic explanatory view of the base sequence as set forth in SEQ ID NO: 1 is presented in (b) of FIG. 15.

A DNA fragment coding for the protein in which 360 amino acid residues at N-terminus of a mouse GLIS1 protein are deleted was amplified by a PCR method using the pMX-mouse GLIS1 vector as a template DNA and PRIMESTAR (registered trademark) MAX DNA polymerase (available from Takara Bio Inc.). Then, the thus-amplified DNA fragments were purified through an agarose electrophoresis to thereby insert between a BamHI site and an XhoI site of the pMX vector. Abase sequence of the thus-inserted fragments was confirmed by a sequencing reaction.
[pMX-Mouse Neurogenin3 Vector]
The pMX-mouse Neurogenin3 vector was prepared in the same manner as in the Test Example 1-1.
[pMX-Mouse Pdx1 Vector]
The pMX-mouse Pdx1 vector was prepared in the same manner as in the Test Example 1-1.
—Production of Retrovirus—
A pMX-GFP vector-derived viral solution, a pMX-mouse GLIS1 vector-derived viral solution, a pMX-mouse mutated GLIS1 vector-derived viral solution, a pMX-mouse Neurogenin3 vector-derived viral solution, and a pMX-mouse Pdx1 vector-derived viral solution were obtained in the same manner as in the Test Example 1-1, except that the plasmid DNAs used in the Test Example 1-1 were changed to plasmid DNAs for this Test Example.

INTRODUCTION

The gene was introduced into the cells in the same manner as in the Test Example 1-1, except that the viral solutions used in the Test Example 1-1 were changed to the following viral solutions.
[Viral Solution]
(1) pMX-GFP vector-derived viral solution (control)
(2) pMX-mouse GLIS1 vector-derived viral solution, pMX-mouse Neurogenin3 vector-derived viral solution, and pMX-mouse Pdx1 vector-derived viral solution
(3) pMX-mouse mutated GLIS1 vector-derived viral solution, pMX-mouse Neurogenin3 vector-derived viral solution, and pMX-mouse Pdx1 vector-derived viral solution
<Determination of Number of dMEF-Derived Insulin Producing Cells>

The number of the DsRed2-positive insulin producing cells was counted in the same manner as in the Test Example 1-1, except that, after the introduction and 17 days of culturing, the DsRed2-positive insulin producing cells were photographed by a fluorescence microscope unit. The results are presented in FIG. 2A.

Figure 2A:
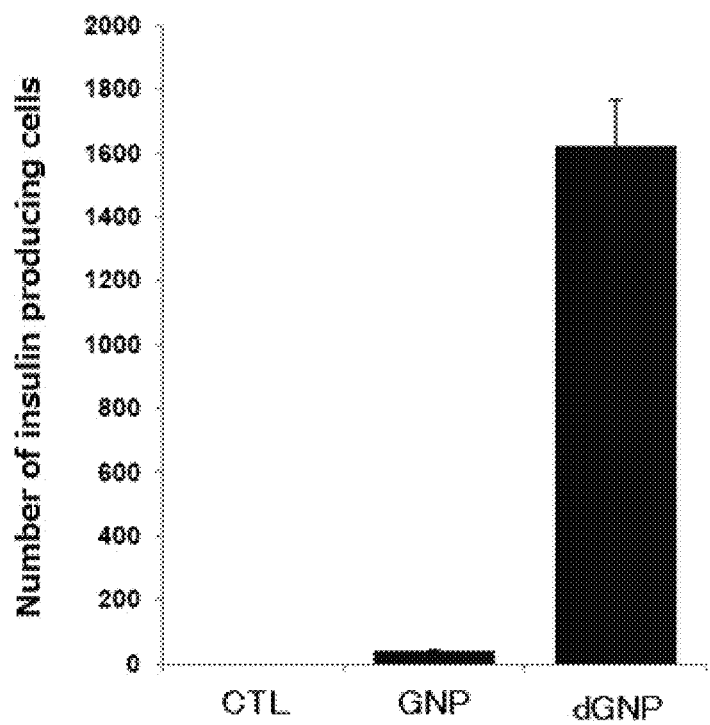
FIG. 2A is a graph illustrating the measurement results of the number of DsRed2-positive insulin producing cells in Test Example 2-1.

In FIG. 2A, "CTL" represents the result in the case of using the (1) pMX-GFP vector-derived viral solution (control), "GNP" represents the result in the case of using the (2) pMX-mouse GLIS1 vector-derived viral solution, pMX-mouse Neurogenin3 vector-derived viral solution, and pMX-mouse Pdx1 vector-derived viral solution, and "dGNP" represents the result in the case of using the (3) pMX-mouse mutated GLIS1 vector-derived viral solution, pMX-mouse Neurogenin3 vector-derived viral solution, and pMX-mouse Pdx1 vector-derived viral solution.

It was demonstrated from the results of FIG. 2A that the production efficiency of the pancreatic endocrine cells was more significantly improved in the case where three factors, i.e., the mutated GLIS1, the Neurogenin3, and the Pdx1 were used, which was one aspect of the method of the present invention, than in the case where three factors, i.e., the GLIS1, the Neurogenin3, and the Pdx1 were used.

<Quantitative PCR Analysis>

The quantitative PCR analysis was performed in the same manner as in the Test Example 1-1.

Figure 2B:
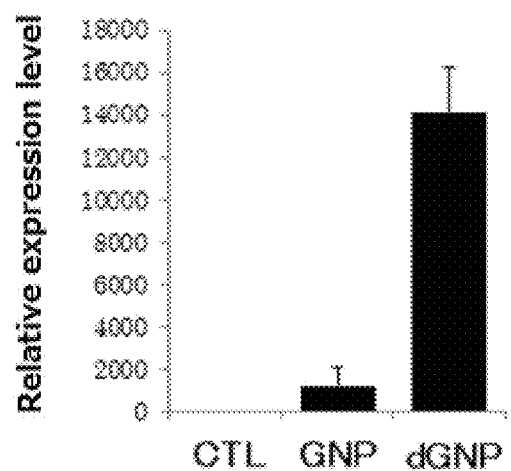
FIG. 2B is a graph illustrating the measurement results of a relative expression level of an insulin gene in Test Example 2-1.

The results are presented in FIG. 2B. In FIG. 2B, "CTL" represents the result in the case of using the (1) pMX-GFP vector-derived viral solution (control), "GNP" represents the result in the case of using the (2) pMX-mouse GLIS1 vector-derived viral solution, pMX-mouse Neurogenin3 vector-derived viral solution, and pMX-mouse Pdx1 vector-derived viral solution, and "dGNP" represents the result in the case of using the (3) pMX-mouse mutated GLIS1 vector-derived viral solution, pMX-mouse Neurogenin3 vector-derived viral solution, and pMX-mouse Pdx1 vector-derived viral solution.

It was demonstrated from the results of FIG. 2B that the expression level of the insulin gene was also increased in the case where three factors, i.e., the mutated GLIS1, the Neurogenin3, and the Pdx1 were used, which was one aspect of the method of the present invention, than in the case where three factors, i.e., the GLIS1, the Neurogenin3, and the Pdx1 were used. This also indicates that the production efficiency of the pancreatic endocrine cells was significantly improved.

Test Example 2-2: Production of Pancreatic Endocrine Cells-2-2

<Preparation of Cells>

The dMEFs were prepared in the same manner as in the Test Example 1-1.

<Production of Retrovirus>

The Plat-GP cells in which viral structural proteins gag-pol and env, which were capable of producing high titer viruses for a long period of time, were expressed under the control of MoMuLV LTR and a plasmid DNA (pMX vector or pMX-puro vector, VSVG vector) were used to produce a retrovirus in the following manner (Onishi, M., et. al., Exp. Hematol. 24, 324-329, 1996).

—Preparation of Plasmid DNA—

[pMX-GFP Vector]

The pMX-GFP vector was prepared in the same manner as in the Test Example 1-1.

[pMX-Human GLIS1 Vector]

The pMX-human GLIS1 vector was prepared in the same manner as in the Test Example 1-2.

[pMX-Human Mutated GLIS1 Vector]

A pMX-human mutated GLIS1 vector is a vector in which a gene coding for a protein in which 190 amino acid residues at N-terminus of a human GLIS1 protein are deleted is inserted into a multi-cloning site of a pMX vector (available from Addgene).

A sequence of the gene coding for a protein in which 190 amino acid residues at N-terminus of a human GLIS1 protein are deleted is as set forth in SEQ ID NO: 2 and was prepared in the following manner.

A DNA fragment coding for the protein in which 190 amino acid residues at N-terminus of a human GLIS1 protein are deleted was amplified by a PCR method using the pMX-human GLIS1 vector as a template DNA and PRIME-STAR (registered trademark) MAX DNA polymerase (available from Takara Bio Inc.). Then, the thus-amplified DNA fragments were purified through an agarose electrophoresis to thereby insert between a BamHI site and an XhoI site of the pMX vector. A base sequence of the thus-inserted fragments was confirmed by a sequencing reaction.

[pMX-Human Neurogenin3 Vector]

The pMX-human Neurogenin3 vector was prepared in the same manner as in the Test Example 1-2.

[pMX-Human Pdx1 Vector]

The pMX-human Pdx1 vector was prepared in the same manner as in the Test Example 1-2.

—Production of Retrovirus—

A pMX-GFP vector-derived viral solution, a pMX-human GLIS1 vector-derived viral solution, a pMX-human mutated GLIS1 vector-derived viral solution, a pMX-human Neurogenin3 vector-derived viral solution, and a pMX-human Pdx1 vector-derived viral solution were obtained in the same manner as in the Test Example 1-2, except that the plasmid DNAs used in the Test Example 1-2 were changed to plasmid DNAs for this Test Example.

INTRODUCTION

The gene was introduced into the cells in the same manner as in the Test Example 1-2, except that the viral solutions used in the Test Example 1-2 were changed to the following viral solutions.

[Viral Solution]

(1) pMX-GFP vector-derived viral solution (control)
(2) pMX-human GLIS1 vector-derived viral solution, pMX-human Neurogenin3 vector-derived viral solution, and pMX-human Pdx1 vector-derived viral solution
(3) pMX-human mutated GLIS1 vector-derived viral solution, pMX-human Neurogenin3 vector-derived viral solution, and pMX-human Pdx1 vector-derived viral solution <Quantitative PCR Analysis>

The quantitative PCR analysis was performed in the same manner as in the Test Example 1-1.

Figure 2C:
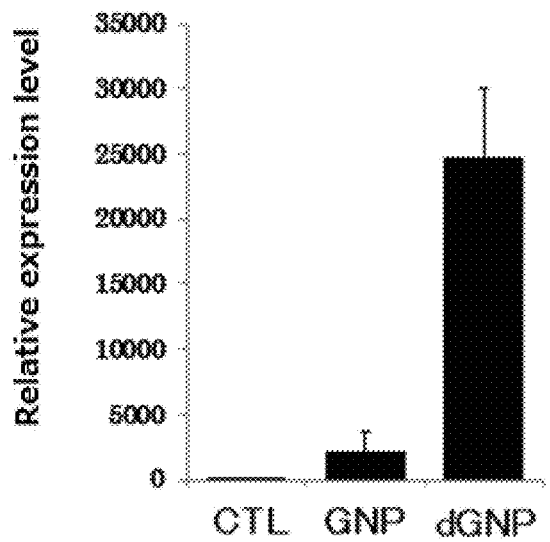
FIG. 2C is a graph illustrating the measurement results of a relative expression level of an insulin gene in Test Example 2-2.

The results are presented in FIG. 2C. In FIG. 2C, "CTL" represents the result in the case of using the (1) pMX-GFP vector-derived viral solution (control), "GNP" represents the result in the case of using the (2) pMX-human GLIS1 vector-derived viral solution, pMX-human Neurogenin3 vector-derived viral solution, and pMX-human Pdx1 vector-derived viral solution, and "dGNP" represents the result in the case of using the (3) pMX-human mutated GLIS1 vector-derived viral solution, pMX-human Neurogenin3 vector-derived viral solution, and pMX-human Pdx1 vector-derived viral solution.

It was demonstrated from the results of FIG. 2C that, when human genes were used, the expression level of the insulin gene was similarly more increased and thus the production efficiency of the pancreatic endocrine cells was more significantly improved in the case where three factors, i.e., the mutated GLIS1, the Neurogenin3, and the Pdx1 were used, which was one aspect of the method of the present invention, than in the case where three factors, i.e., the GLIS1, the Neurogenin3, and the Pdx1 were used.

Test Example 3-1: Production of Pancreatic Endocrine Cells-3-1

<Preparation of Cells>

The dMEFs were prepared in the same manner as in the Test Example 1-1.

<Production of Retrovirus>

The Plat-E cells in which viral structural proteins gag-pol and env, which were capable of producing high titer viruses for a long period of time, were expressed under the control of MoMuLV LTR and a plasmid DNA (pMX vector or pMX-puro vector) were used to produce a retrovirus in the following manner (Onishi, M., et. al., Exp. Hematol. 24, 324-329, 1996).

—Preparation of Plasmid DNA—

[pMX-GFP Vector]

The pMX-GFP vector was prepared in the same manner as in the Test Example 1-1.

[pMX-Mouse GLIS1 Vector]

The pMX-mouse GLIS1 vector was prepared in the same manner as in the Test Example 1-1.

[pMX-Mouse Mutated GLIS1 Vector]

The pMX-mouse mutated GLIS1 vector was prepared in the same manner as in the Test Example 2-1.

[pMX-Mouse Neurogenin3 Vector]

The pMX-mouse Neurogenin3 vector was prepared in the same manner as in the Test Example 1-1.

[pMX-Mouse Pdx1 Vector]

The pMX-mouse Pdx1 vector was prepared in the same manner as in the Test Example 1-1.

[pMX-Mouse MafA Vector]

The pMX-mouse MafA vector was prepared in the same manner as in the Test Example 1-1.

—Production of Retrovirus—

A pMX-GFP vector-derived viral solution, a pMX-mouse GLIS1 vector-derived viral solution, a pMX-mouse mutated GLIS1 vector-derived viral solution, a pMX-mouse Neurogenin3 vector-derived viral solution, a pMX-mouse Pdx1 vector-derived viral solution, and a pMX-mouse MafA vector-derived viral solution were obtained in the same manner as in the Test Example 1-1, except that the plasmid DNAs used in the Test Example 1-1 were changed to plasmid DNAs for this Test Example.

INTRODUCTION

The gene was introduced into the cells in the same manner as in the Test Example 1-1, except that the viral solutions used in the Test Example 1-1 were changed to the following viral solutions.

[Viral Solution]

(1) pMX-GFP vector-derived viral solution (control)

(2) pMX-mouse GLIS1 vector-derived viral solution, pMX-mouse Neurogenin3 vector-derived viral solution, pMX-mouse Pdx1 vector-derived viral solution, and pMX-mouse MafA vector-derived viral solution (3) pMX-mouse mutated GLIS1 vector-derived viral solution, pMX-mouse Neurogenin3 vector-derived viral solution, pMX-mouse Pdx1 vector-derived viral solution, and pMX-mouse MafA vector-derived viral solution <Determination of Number of dMEF-Derived Insulin Producing Cells>

The number of the DsRed2-positive insulin producing cells was counted in the same manner as in the Test Example 1-1, except that, after the introduction and 21 days of culturing, the DsRed2-positive insulin producing cells were photographed by a fluorescence microscope unit. The results are presented in FIG. 3A.

Figure 3A:
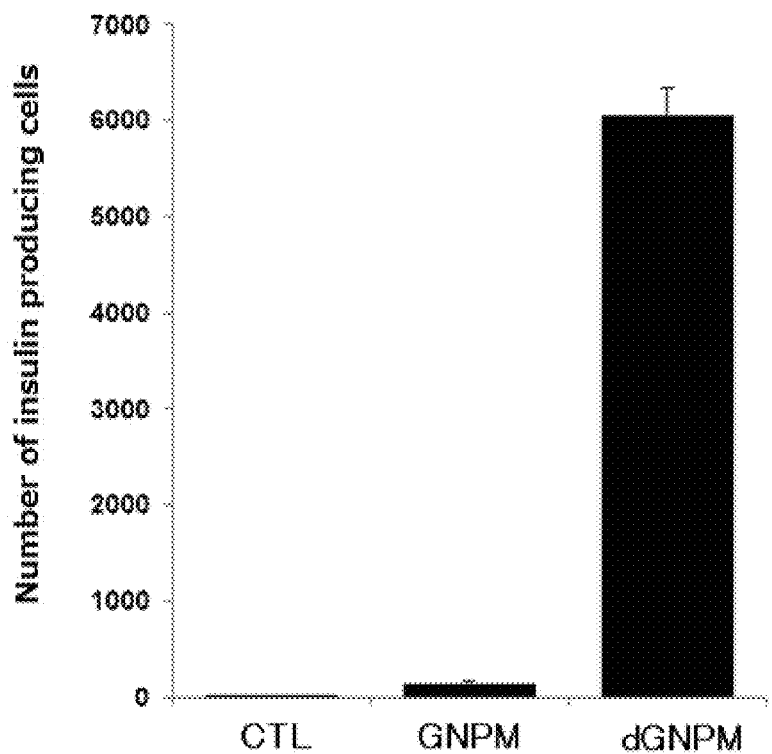
FIG. 3A is a graph illustrating the measurement results of the number of DsRed2-positive insulin producing cells in Test Example 3-1.

In FIG. 3A, "CTL" represents the result in the case of using the (1) pMX-GFP vector-derived viral solution (control), "GNPM" represents the result in the case of using the (2) pMX-mouse GLIS1 vector-derived viral solution, pMX-mouse Neurogenin3 vector-derived viral solution, pMX-mouse Pdx1 vector-derived viral solution, and pMX-mouse MafA vector-derived viral solution, and "dGNPM" represents the result in the case of using the (3) pMX-mouse mutated GLIS1 vector-derived viral solution, pMX-mouse Neurogenin3 vector-derived viral solution, pMX-mouse Pdx1 vector-derived viral solution, and pMX-mouse MafA vector-derived viral solution.

It was demonstrated from the results of FIG. 3A that the production efficiency of the pancreatic endocrine cells was more significantly improved in the case where four factors, i.e., the mutated GLIS1, the Neurogenin3, the Pdx1, and the MafA were used, which was one aspect of the method of the present invention, than in the case where four factors, i.e., the GLIS1, the Neurogenin3, the Pdx1, and the MafA were used, which was one aspect of the method of the present invention.

<Quantitative PCR Analysis>

The quantitative PCR analysis was performed in the same manner as in the Test Example 1-1.

Figure 3B:
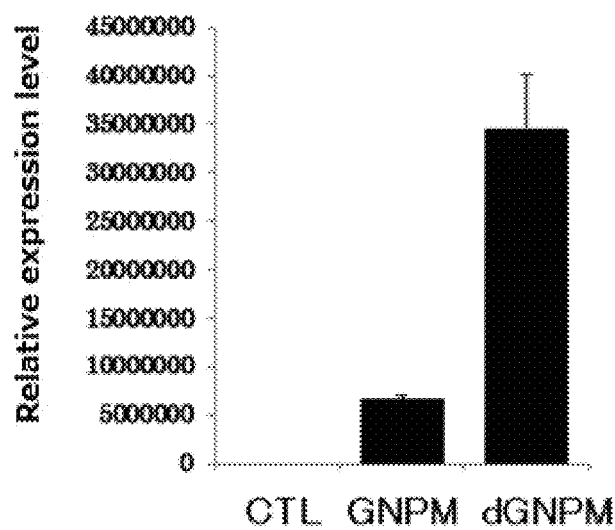
FIG. 3B is a graph illustrating the measurement results of a relative expression level of an insulin gene in Test Example 3-1.

The results are presented in FIG. 3B. In FIG. 3B, "CTL" represents the result in the case of using the (1) pMX-GFP vector-derived viral solution (control), "GNPM" represents the result in the case of using the (2) pMX-mouse GLIS1 vector-derived viral solution, pMX-mouse Neurogenin3 vector-derived viral solution, pMX-mouse Pdx1 vector-derived viral solution, and pMX-mouse MafA vector-derived viral solution, and "dGNPM" represents the result in the case of using the (3) pMX-mouse mutated GLIS1 vector-derived viral solution, pMX-mouse Neurogenin3 vector-derived viral solution, pMX-mouse Pdx1 vector-derived viral solution, and pMX-mouse MafA vector-derived viral solution.

It was demonstrated from the results of FIG. 3B that the expression level of the insulin gene was also increased in the case where four factors, i.e., the mutated GLIS1, the Neurogenin3, the Pdx1, and the MafA were used, which was one aspect of the method of the present invention, than in the case where four factors, i.e., the GLIS1, the Neurogenin3, the Pdx1, and the MafA were used, which was one aspect of the method of the present invention. This also indicates that production efficiency of the pancreatic endocrine cells was more significantly improved.

Test Example 3-2: Production of Pancreatic Endocrine Cells-3-2

<Preparation of Cells>

The dMEFs were prepared in the same manner as in the Test Example 1-1.

<Production of Retrovirus>

The Plat-GP cells in which viral structural proteins gag-pol and env, which were capable of producing high titer viruses for a long period of time, were expressed under the control of MoMuLV LTR and a plasmid DNA (pMX vector or pMX-puro vector, VSVG vector) were used to produce a retrovirus in the following manner (Onishi, M., et. al., Exp. Hematol. 24, 324-329, 1996).

—Preparation of Plasmid DNA—

[pMX-GFP Vector]

The pMX-GFP vector was prepared in the same manner as in the Test Example 1-1.

[pMX-Human GLIS1 Vector]

The pMX-human GLIS1 vector was prepared in the same manner as in the Test Example 1-2.

[pMX-Human Mutated GLIS1 Vector]

The pMX-human mutated GLIS1 vector was prepared in the same manner as in the Test Example 2-2.

[pMX-Human Neurogenin3 Vector]

The pMX-human Neurogenin3 vector was prepared in the same manner as in the Test Example 1-2.

[pMX-Human Pdx1 Vector]

The pMX-human Pdx1 vector was prepared in the same manner as in the Test Example 1-2.

[pMX-Human MafA Vector]

The pMX-human MafA vector was prepared in the same manner as in the Test Example 1-2.

—Production of Retrovirus—

A pMX-GFP vector-derived viral solution, a pMX-human GLIS1 vector-derived viral solution, a pMX-human mutated GLIS1 vector-derived viral solution, a pMX-human Neurogenin3 vector-derived viral solution, a pMX-human Pdx1 vector-derived viral solution, and a pMX-human MafA vector-derived viral solution were obtained in the same manner as in the Test Example 1-2, except that the plasmid DNAs used in the Test Example 1-2 were changed to plasmid DNAs for this Test Example.

INTRODUCTION

The gene was introduced into the cells in the same manner as in the Test Example 1-2, except that the viral solutions used in the Test Example 1-2 were changed to the following viral solutions.

[Viral Solution]

(1) pMX-GFP vector-derived viral solution (control)

(2) pMX-human GLIS1 vector-derived viral solution, pMX-human Neurogenin3 vector-derived viral solution, pMX-human Pdx1 vector-derived viral solution, and pMX-human MafA vector-derived viral solution (3) pMX-human mutated GLIS1 vector-derived viral solution, pMX-human Neurogenin3 vector-derived viral solution, pMX-human Pdx1 vector-derived viral solution, and pMX-human MafA vector-derived viral solution <Quantitative PCR Analysis>

The quantitative PCR analysis was performed in the same manner as in the Test Example 1-1.

Figure 3C:
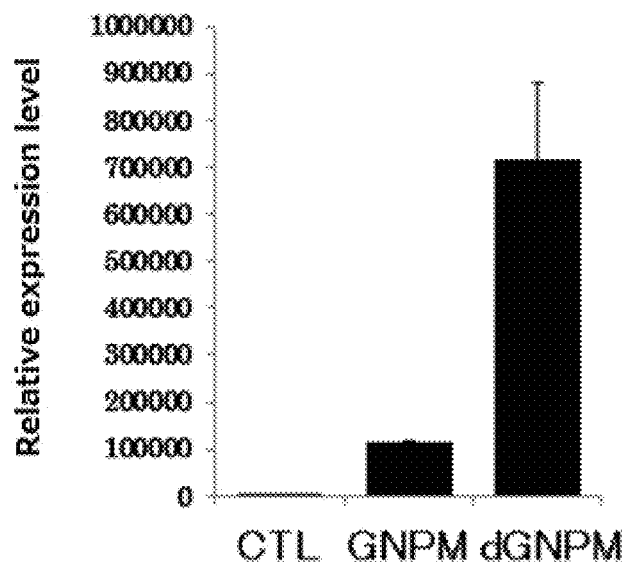
FIG. 3C is a graph illustrating the measurement results of a relative expression level of an insulin gene in Test Example 3-2.

The results are presented in FIG. 3C. In FIG. 3C, "CTL" represents the result in the case of using the (1) pMX-GFP vector-derived viral solution (control), "GNPM" represents the result in the case of using the (2) pMX-human GLIS1 vector-derived viral solution, pMX-human Neurogenin3 vector-derived viral solution, pMX-human Pdx1 vector-derived viral solution, and pMX-human MafA vector-derived viral solution, and "dGNPM" represents the result in the case of using the (3) pMX-human mutated GLIS1 vector-derived viral solution, pMX-human Neurogenin3 vector-derived viral solution, pMX-human Pdx1 vector-derived viral solution, and pMX-human MafA vector-derived viral solution.

It was demonstrated from the results of FIG. 3C that, when human genes were used, the expression level of the insulin gene was similarly more increased and thus the production efficiency of the pancreatic endocrine cells was more significantly improved in the case where four factors, i.e., the mutated GLIS1, the Neurogenin3, the Pdx1, and the MafA were used, which was one aspect of the method of the present invention, than in the case where four factors, i.e., the GLIS1, the Neurogenin3, the Pdx1, and the MafA were used, which was one aspect of the method of the present invention.

Test Example 4: Glucose-Responsive Insulin Secretion Test-1

<Preparation of Cells>

The dMEFs were prepared in the same manner as in the Test Example 1-1.

<Production of Retrovirus>

The Plat-E cells in which viral structural proteins gag-pol and env, which were capable of producing high titer viruses for a long period of time, were expressed under the control of MoMuLV LTR and a plasmid DNA (pMX vector or pMX-puro vector) were used to produce a retrovirus in the following manner (Onishi, M., et. al., Exp. Hematol. 24, 324-329, 1996).

—Preparation of Plasmid DNA—

[pMX-Mouse GLIS1 Vector]

The pMX-mouse GLIS1 vector was prepared in the same manner as in the Test Example 1-1.

[pMX-Mouse Neurogenin3 Vector]

The pMX-mouse Neurogenin3 vector was prepared in the same manner as in the Test Example 1-1.

[pMX-Mouse Pdx1 Vector]

The pMX-mouse Pdx1 vector was prepared in the same manner as in the Test Example 1-1.

[pMX-Mouse MafA Vector]

The pMX-mouse MafA vector was prepared in the same manner as in the Test Example 1-1.

—Production of Retrovirus—

A pMX-mouse GLIS1 vector-derived viral solution, a pMX-mouse Neurogenin3 vector-derived viral solution, a pMX-mouse Pdx1 vector-derived viral solution, and a pMX-mouse MafA vector-derived viral solution were obtained in the same manner as in the Test Example 1-1, except that the plasmid DNAs used in the Test Example 1-1 were changed to plasmid DNAs for this Test Example.

INTRODUCTION

The gene was introduced into the cells in the same manner as in the Test Example 1-1, except that the viral solutions used in the Test Example 1-1 were changed to the following viral solution.

[Viral Solution]

(1) pMX-mouse GLIS1 vector-derived viral solution, pMX-mouse Neurogenin3 vector-derived viral solution, pMX-mouse Pdx1 vector-derived viral solution, and pMX-mouse MafA vector-derived viral solution <Glucose-Responsive Insulin Secretion Test>

Thirty-four days after the introduction, all of pancreatic islet-like masses were picked up by a pipette and transferred into a 24-well plate (low adhesive plate (EZ-BINDSHUT II, available from AGC TECHNO GLASS CO., LTD.)). Then, a glucose-responsive insulin secretion test was performed in the following manner.

The pancreatic islet-like masses were cultured in a 1.4 mM glucose-containing Ringer's solution for 3 hours. Then, the medium was replaced and the masses were cultured in a 2.8 mM glucose-containing Ringer's solution for another 1 hour, of which culture supernatant was used as a reference (hereinafter may be referred to as "reference culture supernatant").

Then, the pancreatic islet-like masses were cultured in a 16.8 mM glucose-containing Ringer's solution for 1 hour. A culture supernatant thereof was transferred into a 1.5 mL tube (hereinafter may be referred to as "high-glucose culture supernatant").

An insulin concentration in each of the culture supernatants was measured by ELISA assay (human insulin ELISA kit, available from Mercodia). The results are presented in FIG. 4.

Figure 4:
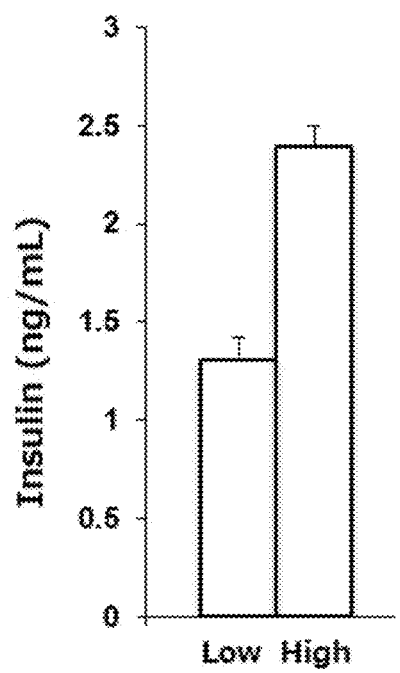
FIG. 4 is a graph illustrating the results of a glucose-responsive insulin secretion test in Test Example 4.

In FIG. 4, a left bar ("low") represents the result of the reference culture supernatant and a right bar ("high") represents the result of the high-glucose culture supernatant.

For the results of FIG. 4, an amount of insulin was small at a low glucose concentration and the amount of insulin was increased at a higher glucose concentration. Therefore, the pancreatic islet-like masses produced by the method of the present invention were confirmed to have functions required for pancreatic endocrine cells.

Test Example 5: Glucose-Responsive Insulin Secretion Test-2

<Preparation of Cells>
The dMEFs were prepared in the same manner as in the Test Example 1-1.
<Production of Retrovirus>
The pMX-mouse GLIS1 vector-derived viral solution, the pMX-mouse Neurogenin3 vector-derived viral solution, the pMX-mouse Pdx1 vector-derived viral solution, and the pMX-mouse MafA vector-derived viral solution were obtained in the same manner as in the Test Example 4.

INTRODUCTION

The gene was introduced into the cells in the same manner as in the Test Example 4 using the following viral solution.
[Viral Solution]
(1) pMX-mouse GLIS1 vector-derived viral solution, pMX-mouse Neurogenin3 vector-derived viral solution, pMX-mouse Pdx1 vector-derived viral solution, and pMX-mouse MafA vector-derived viral solution
<Glucose-Responsive Insulin Secretion Test>
Twenty-seven days after the introduction, 30 uniform pancreatic islet-like masses having a diameter of 100 μm to 300 μm were picked up by a pipette under a stereoscopic microscope and transferred into a 24-well plate (low adhesive plate (EZ-BINDSHUT II, available from AGC TECHNO GLASS CO., LTD.). Then, a glucose-responsive insulin secretion test was performed in the same manner.

The pancreatic islet-like masses were cultured in a 2.8 mM glucose-containing Ringer's solution for 3 hours. Then, the medium was replaced and the masses were cultured for another 1 hour, of which culture supernatant was used as a reference (hereinafter may be referred to as "reference culture supernatant").

Then, the pancreatic islet-like masses were cultured in a 16.8 mM glucose-containing Ringer's solution for 1 hour. A culture supernatant thereof was transferred into a 1.5 mL tube (hereinafter may be referred to as "high-glucose culture supernatant").

Then, a 2.8 mM glucose-containing Ringer's solution was added to wells, where the pancreatic islet-like masses were cultured for 1 hour. A culture supernatant thereof was transferred into a 1.5 mL tube (hereinafter may be referred to as "low-glucose culture supernatant").

An insulin concentration in each of the culture supernatants was measured by ELISA assay (available from Shibayagi Co., Ltd., TYPE T). The results are presented in FIG. 5.

Figure 5:
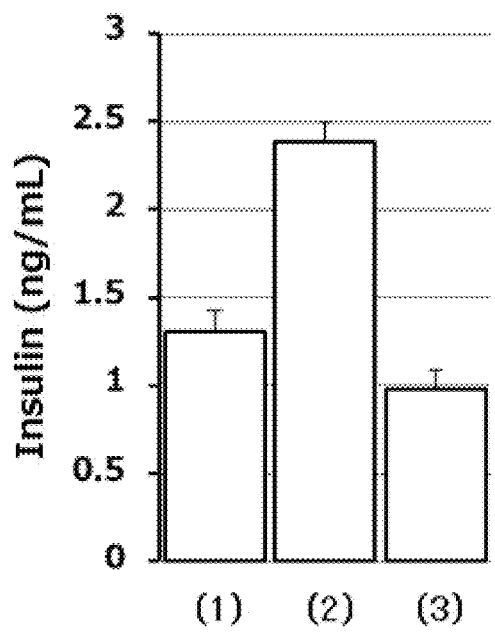
FIG. 5 is a graph illustrating the results of a glucose-responsive insulin secretion test in Test Example 5.

In FIG. 5, a left bar ((1)) represents the result of the reference culture supernatant, a middle bar ((2)) represents the result of the high-glucose culture supernatant, and a right bar ((3)) represents the result of the low-glucose culture supernatant.

It was confirmed from the results of FIG. 5 that an amount of insulin was small at a low glucose concentration ((1)), the amount of insulin was increased at a higher glucose concentration ((2)), and a concentration of insulin was decreased at a lower glucose concentration ((3)). Therefore, also in this Test Example, the pancreatic endocrine cells obtained by the method of the present invention were confirmed to have functions required for pancreatic endocrine cells.

Test Example 6: Production of Pancreatic Endocrine Cells from Mouse Mesenchymal Stem Cells <Preparation of Cells>
Mouse mesenchymal stem cells (Cyagen catalog No. MUBMX-01001) (hereinafter may be referred to as "mouse MSC") were prepared as cells. The mouse MSCs were subcultured in an ADSC-BM medium (supplemented with 10% FBS, penicillin-streptomycin).
<Production of Retrovirus>
The pMX-GFP vector-derived viral solution, the pMX-mouse GLIS1 vector-derived viral solution, the pMX-mouse Neurogenin3 vector-derived viral solution, the pMX-mouse Pdx1 vector-derived viral solution, and the pMX-mouse MafA vector-derived viral solution were obtained in the same manner as in the Test Example 1-1.

INTRODUCTION

The mouse MSCs were infected with the retrovirus to thereby introduce the gene(s) into the cells. The infection was performed in the following manner.

The mouse MSCs were seeded in a 24-well plate at $2.5 \cdot 10^4$ cells per well.

On the following day, an 8 mg/mL polybrene solution (available from Sigma, 107689) was added to the viral solution at a final concentration of 8 μg/mL. The culture supernatant of the mouse MSCs was removed through aspiration, and then each of the below-described viral solutions was added to a 24-well plate at 200 μL per well. Note that, amounts of the viral solutions were adjusted so as to be uniform for each well with a DMEM (containing 10% FBS) solution containing 8 sg/mL polybrene. After the addition of the viral solutions, the resultant solutions were incubated within an incubator with 5% $CO_2$ at 37° C. During the incubation, the media were changed every 2 or 3 days.
[Viral Solution]
(1) pMX-GFP vector-derived viral solution (control)
(2) pMX-mouse GLIS1 vector-derived viral solution, pMX-mouse Neurogenin3 vector-derived viral solution, pMX-mouse Pdx1 vector-derived viral solution, and pMX-mouse MafA vector-derived viral solution
<Quantitative PCR Analysis>
The quantitative PCR analysis was performed in the same manner as in the Test Example 1-1.

Figure 6:
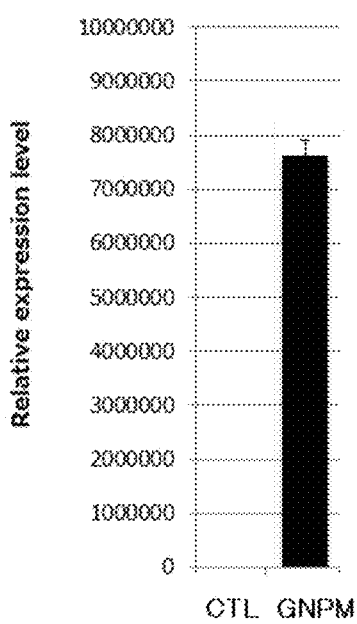
FIG. 6 is a graph illustrating the measurement results of a relative expression level of an insulin gene in Test Example 6.

The results are presented in FIG. 6. In FIG. 6, "CTL" represents the result in the case of using the (1) pMX-GFP vector-derived viral solution (control) and "GNPM" represents the result in the case of using the (2) pMX-mouse GLIS1 vector-derived viral solution, pMX-mouse Neurogenin3 vector-derived viral solution, pMX-mouse Pdx1 vector-derived viral solution, and pMX-mouse MafA vector-derived viral solution.

It was demonstrated from the results of FIG. 6 that, when the mesenchymal stem cells were used as cells, the pancreatic endocrine cells were similarly able to be produced efficiently by using four factors, i.e., the GLIS1, the Neurogenin3, the Pdx1, and the MafA, which was one aspect of the method of the present invention.

Test Example 7: Production of Pancreatic Endocrine Cells from Human Neonatal Fibroblasts <Preparation of Cells>
Human neonatal fibroblasts (NHDF) (D10051, available from TAKARA SHUZO CO., LTD.) were prepared as human cells.
<Production of Retrovirus>
The pMX-GFP vector-derived viral solution, the pMX-human mutated GLIS1 vector-derived viral solution, the pMX-human Neurogenin3 vector-derived viral solution, and the pMX-human MafA vector-derived viral solution were obtained in the same manner as in the Test Example 1-2 or 2-2.

INTRODUCTION

Figure 7:
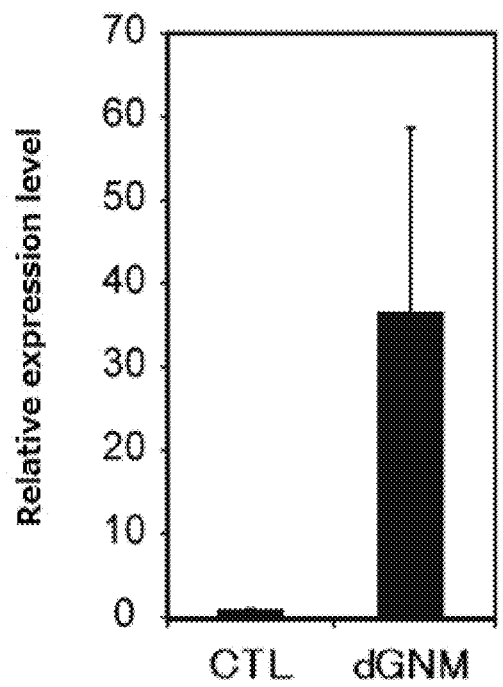
FIG. 7 is a graph illustrating the measurement results of a relative expression level of an insulin gene in Test Example 7.

The genes were introduced into cells in the same manner as in the Test Example 1-2, except that the cells used in the Test Example 1-2 (dMEFs) were changed to the human neonatal fibroblasts. Note that, the following viral solutions were used.
[Viral Solution]
(1) pMX-GFP vector-derived viral solution (control)
(2) pMX-human mutated GLIS1 vector-derived viral solution, pMX-human Neurogenin3 vector-derived viral solution, and pMX-human MafA vector-derived viral solution
<Quantitative PCR Analysis>
The quantitative PCR analysis was performed in the same manner as in the Test Example 1-1, except that the primers used in the Test Example 1-1 were changed to the following primers.
—Human GAPDH Gene—
  Forward: 5'-atgttcgtcatgggtgtgaa-3' (SEQ ID NO: 7)
  Reverse: 5'-tgtggtcatgagtccttcca-3' (SEQ ID NO: 8)
—Human Insulin Gene—
  Forward: 5'-gccatcaagcagatcactgt-3' (SEQ ID NO: 9)
  Reverse: 5'-caggtgttggttcacaaagg-3' (SEQ ID NO: 10)
The results are presented in FIG. 7. In FIG. 7, "CTL" represents the result in the case of using the (1) pMX-GFP vector-derived viral solution (control) and "dGNM" represents the result in the case of using the (2) pMX-human mutated GLIS1 vector-derived viral solution, pMX-human Neurogenin3 vector-derived viral solution, and pMX-human MafA vector-derived viral solution.

It was demonstrated from the results of FIG. 7 that, when human genes were used, the pancreatic endocrine cells were similarly able to be produced efficiently in the case where three factors, i.e., the mutated GLIS1, the Neurogenin3, and the MafA were used, which was one aspect of the method of the present invention.

Test Example 8: Production of Pancreatic Endocrine Cells from Human Brain Cells

<Preparation of Cells>
Human glioma T98G cell line (RCB1954, RIKEN) were prepared as human brain cells.
<Production of Retrovirus>
The pMX-GFP vector-derived viral solution, the pMX-human GLIS1 vector-derived viral solution, the pMX-human mutated GLIS1 vector-derived viral solution, the pMX-human Neurogenin3 vector-derived viral solution, the pMX-human Pdx1 vector-derived viral solution, and the pMX-human MafA vector-derived viral solution were obtained in the same manner as in the Test Example 1-2 or 2-2.

INTRODUCTION

The genes were introduced into cells in the same manner as in the Test Example 1-2, except that the cells used in the Test Example 1-2 (dMEFs) were changed to the human glioma T98G cell line. Note that, the following viral solutions were used.
[Viral Solution]
(1) pMX-GFP vector-derived viral solution (control)
(2) pMX-human GLIS1 vector-derived viral solution, pMX-human Neurogenin3 vector-derived viral solution, pMX-human Pdx1 vector-derived viral solution, and pMX-human MafA vector-derived viral solution
(3) pMX-human mutated GLIS1 vector-derived viral solution, pMX-human Neurogenin3 vector-derived viral solution, pMX-human Pdx1 vector-derived viral solution, and pMX-human MafA vector-derived viral solution
(4) pMX-human mutated GLIS1 vector-derived viral solution, pMX-human Neurogenin3 vector-derived viral solution, and pMX-human MafA vector-derived viral solution
(5) pMX-human mutated GLIS1 vector-derived viral solution, pMX-human Neurogenin3 vector-derived viral solution, and pMX-human Pdx1 vector-derived viral solution
<Quantitative PCR Analysis>
The quantitative PCR analysis was performed in the same manner as in the Test Example 7.

Figure 8:
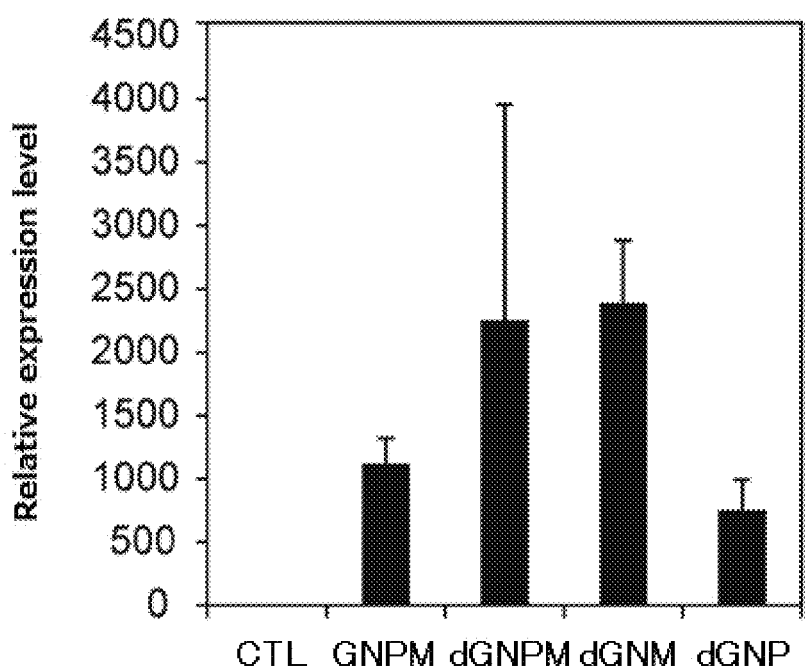
FIG. 8 is a graph illustrating the measurement results of a relative expression level of an insulin gene in Test Example 8.

The results are presented in FIG. 8. In FIG. 8, "CTL" represents the result in the case of using the (1) pMX-GFP vector-derived viral solution (control), "GNPM" represents the result in the case of using the (2) pMX-human GLIS1 vector-derived viral solution, pMX-human Neurogenin3 vector-derived viral solution, pMX-human Pdx1 vector-derived viral solution, and pMX-human MafA vector-derived viral solution, "dGNPM" represents the result in the case of using the (3) pMX-human mutated GLIS1 vector-derived viral solution, pMX-human Neurogenin3 vector-derived viral solution, pMX-human Pdx1 vector-derived viral solution, and pMX-human MafA vector-derived viral solution, "dGNM" represents the result in the case of using the (4) pMX-human mutated GLIS1 vector-derived viral solution, pMX-human Neurogenin3 vector-derived viral solution, and pMX-human MafA vector-derived viral solution, and "dGNP" represents the result in the case of using the (5) pMX-human mutated GLIS1 vector-derived viral solution, pMX-human Neurogenin3 vector-derived viral solution, and pMX-human Pdx1 vector-derived viral solution.

It was demonstrated from the results of FIG. 8 that the pancreatic endocrine cells were able to be produced efficiently using human cells in any case where factors according to any of aspects of the method of the present invention were used.

Test Example 9: Production of Pancreatic Endocrine Cells from Human Kidney Cells <Preparation of Cells>
HEK293 cells (RCB1637, available from Riken BioResource Research Center) were prepared as human kidney cells.
<Production of Retrovirus>
The pMX-GFP vector-derived viral solution, the pMX-mouse mutated GLIS1 vector-derived viral solution, the pMX-mouse Neurogenin3 vector-derived viral solution, the pMX-mouse Pdx1 vector-derived viral solution, and the pMX-mouse MafA vector-derived viral solution were obtained in the same manner as in the Test Example 1-1 or 2-1.

INTRODUCTION

Figure 9:
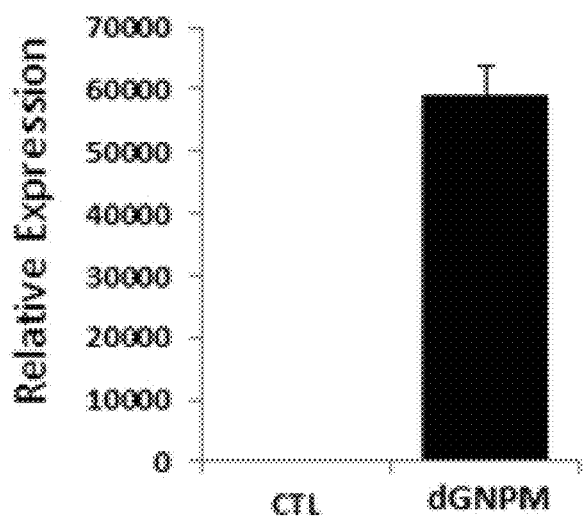
FIG. 9 is a graph illustrating the measurement results of a relative expression level of an insulin gene in Test Example 9.

The genes were introduced into cells in the same manner as in the Test Example 1-1, except that the cells used in the Test Example 1-1 (dMEFs) were changed to the HEK293 cells. Note that, the following viral solutions were used.
[Viral Solution]
(1) pMX-GFP vector-derived viral solution (control)
(2) pMX-mouse mutated GLIS1 vector-derived viral solution, pMX-mouse Neurogenin3 vector-derived viral solution, pMX-mouse Pdx1 vector-derived viral solution, and pMX-mouse MafA vector-derived viral solution
<Quantitative PCR Analysis>
Using the cells after the introduction and 4 days of culturing, the quantitative PCR analysis was performed in the same manner as in the Test Example 1-1.
The results are presented in FIG. 9. In FIG. 9, "CTL" represents the result in the case of using the (1) pMX-GFP vector-derived viral solution (control) and "dGNPM" represents the result in the case of using the (2) pMX-mouse mutated GLIS1 vector-derived viral solution, pMX-mouse Neurogenin3 vector-derived viral solution, pMX-mouse Pdx1 vector-derived viral solution, and pMX-mouse MafA vector-derived viral solution.
It was demonstrated from the results of FIG. 9 that the pancreatic endocrine cells were able to be produced efficiently even using human kidney cells by using four factors of the mutated GLIS1, Neurogenin3, Pdx1, and MafA, which is one aspect of the method of the present invention.

Test Example 10: Production of Pancreatic Endocrine Cells from Mouse Enterocytes <Preparation of Cells>
GLUTag cells (provided by Dr. Daniel J. Drucker of Mount Sinai Hospital) were prepared as mouse enterocytes.
<Production of Retrovirus>
The pMX-GFP vector-derived viral solution, the pMX-mouse mutated GLIS1 vector-derived viral solution, the pMX-mouse Neurogenin3 vector-derived viral solution, the pMX-mouse Pdx1 vector-derived viral solution, and the pMX-mouse MafA vector-derived viral solution were obtained in the same manner as in the Test Example 1-1 or 2-1.

INTRODUCTION

Figure 10:
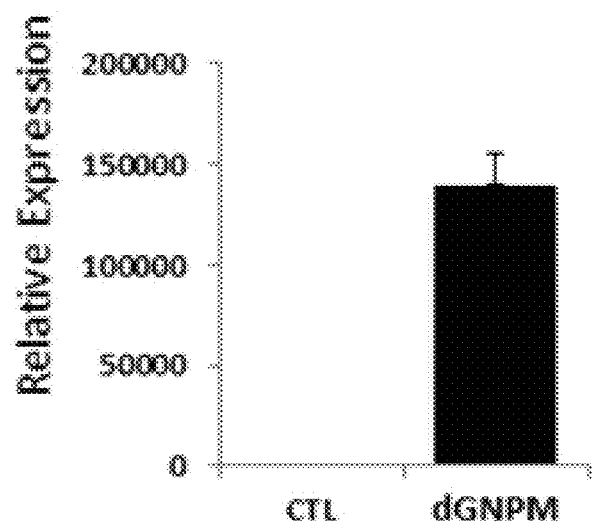
FIG. 10 is a graph illustrating the measurement results of a relative expression level of an insulin gene in Test Example 10.

The genes were introduced into cells in the same manner as in the Test Example 1-1, except that the cells used in the Test Example 1-1 (dMEFs) were changed to the GLUTag cells. Note that, the following viral solutions were used.
[Viral Solution]
(1) pMX-GFP vector-derived viral solution (control)
(2) pMX-mouse mutated GLIS1 vector-derived viral solution, pMX-mouse Neurogenin3 vector-derived viral solution, pMX-mouse Pdx1 vector-derived viral solution, and pMX-mouse MafA vector-derived viral solution
<Quantitative PCR Analysis>
Using the cells after the introduction and 14 days of culturing, the quantitative PCR analysis was performed in the same manner as in the Test Example 1-1.
The results are presented in FIG. 10. In FIG. 10, "CTL" represents the result in the case of using the (1) pMX-GFP vector-derived viral solution (control) and "dGNPM" represents the result in the case of using the (2) pMX-mouse mutated GLIS1 vector-derived viral solution, pMX-mouse Neurogenin3 vector-derived viral solution, pMX-mouse Pdx1 vector-derived viral solution, and pMX-mouse MafA vector-derived viral solution.
It was demonstrated from the results of FIG. 10 that the pancreatic endocrine cells were able to be produced efficiently even using mouse enterocytes by using four factors of the mutated GLIS1, Neurogenin3, Pdx1, and MafA, which is one aspect of the method of the present invention.

Test Example 11: Production of Pancreatic Endocrine Cells from Human Liver Cells <Preparation of Cells>
HuH7 cells (RCB1366, available from Riken BioResource Research Center) were prepared as human liver cells.
<Production of Retrovirus>
The pMX-GFP vector-derived viral solution, the pMX-mouse mutated GLIS1 vector-derived viral solution, the pMX-mouse Neurogenin3 vector-derived viral solution, the pMX-mouse Pdx1 vector-derived viral solution, and the pMX-mouse MafA vector-derived viral solution were obtained in the same manner as in the Test Example 1-1 or 2-1.

INTRODUCTION

Figure 11:
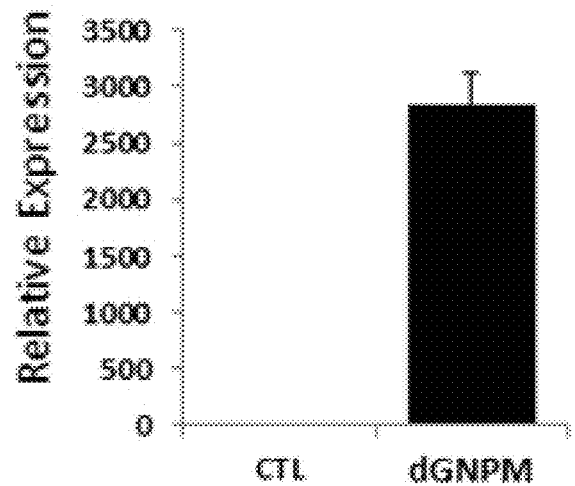
FIG. 11 is a graph illustrating the measurement results of a relative expression level of an insulin gene in Test Example 11.

The genes were introduced into cells in the same manner as in the Test Example 1-1, except that the cells used in the Test Example 1-1 (dMEFs) were changed to the HuH7 cells. Note that, the following viral solutions were used.
[Viral Solution]
(1) pMX-GFP vector-derived viral solution (control)
(2) pMX-mouse mutated GLIS1 vector-derived viral solution, pMX-mouse Neurogenin3 vector-derived viral solution, pMX-mouse Pdx1 vector-derived viral solution, and pMX-mouse MafA vector-derived viral solution
<Quantitative PCR Analysis>
Using the cells after the introduction and 2 days of culturing, the quantitative PCR analysis was performed in the same manner as in the Test Example 1-1.
The results are presented in FIG. 11. In FIG. 11, "CTL" represents the result in the case of using the (1) pMX-GFP vector-derived viral solution (control) and "dGNPM" represents the result in the case of using the (2) pMX-mouse mutated GLIS1 vector-derived viral solution, pMX-mouse Neurogenin3 vector-derived viral solution, pMX-mouse Pdx1 vector-derived viral solution, and pMX-mouse MafA vector-derived viral solution.
It was demonstrated from the results of FIG. 11 that the pancreatic endocrine cells were able to be produced efficiently even using human liver cells by using four factors of the mutated GLIS1, Neurogenin3, Pdx1, and MafA, which is one aspect of the method of the present invention.

Test Example 12: Production of Pancreatic Endocrine Cells from Human Liver Cells <Preparation of Cells>

HepG2 cells (RCB1886, available from Riken BioResource Research Center) were prepared as human liver cells.
<Production of Retrovirus>

The pMX-GFP vector-derived viral solution, the pMX-human GLIS1 vector-derived viral solution, the pMX-human mutated GLIS1 vector-derived viral solution, the pMX-human Neurogenin3 vector-derived viral solution, the pMX-human Pdx1 vector-derived viral solution, and the pMX-human MafA vector-derived viral solution were obtained in the same manner as in the Test Example 1-2 or 2-2.

INTRODUCTION

The genes were introduced into cells in the same manner as in the Test Example 1-2, except that the cells used in the Test Example 1-1 (dMEFs) were changed to the HepG2 cells. Note that, the following viral solutions were used.
[Viral solution]
(1) pMX-GFP vector-derived viral solution (control)
(2) pMX-human GLIS1 vector-derived viral solution, pMX-human Neurogenin3 vector-derived viral solution, pMX-human Pdx1 vector-derived viral solution, and pMX-human MafA vector-derived viral solution
(3) pMX-human mutated GLIS1 vector-derived viral solution, pMX-human Neurogenin3 vector-derived viral solution, pMX-human Pdx1 vector-derived viral solution, and pMX-human MafA vector-derived viral solution
(4) pMX-human mutated GLIS1 vector-derived viral solution, pMX-human Neurogenin3 vector-derived viral solution, and pMX-human MafA vector-derived viral solution
(5) pMX-human mutated GLIS1 vector-derived viral solution, pMX-human Neurogenin3 vector-derived viral solution, and pMX-human Pdx1 vector-derived viral solution
<Quantitative PCR Analysis>

Using the cells after the introduction and 4 days of culturing, the quantitative PCR analysis was performed in the same manner as in the Test Example 7.

Figure 12:
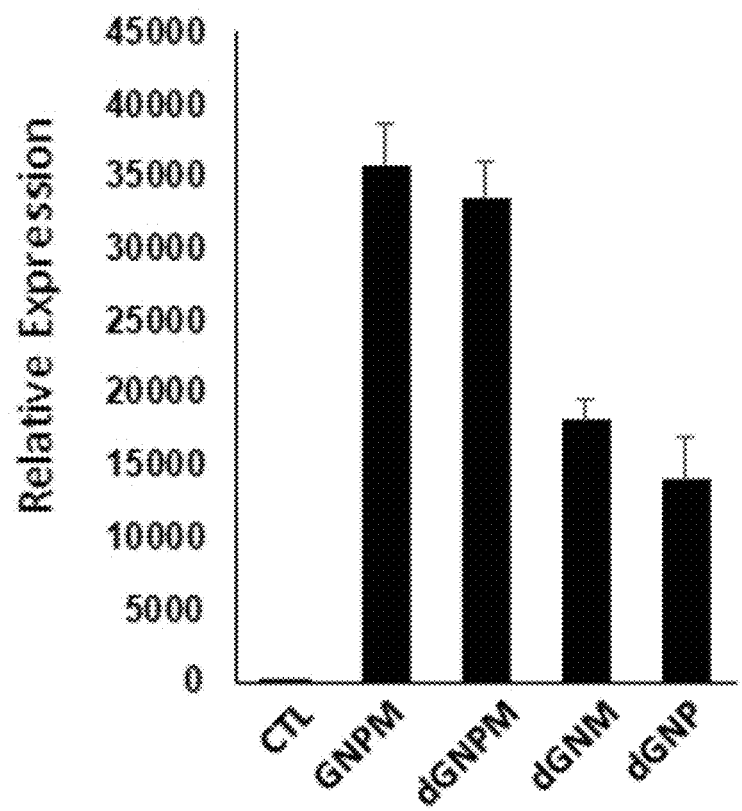
FIG. 12 is a graph illustrating the measurement results of a relative expression level of an insulin gene in Test Example 12.

The results are presented in FIG. 12. In FIG. 12, "CTL" represents the result in the case of using the (1) pMX-GFP vector-derived viral solution (control), is "GNPM" represents the result in the case of using the (2) pMX-human GLIS1 vector-derived viral solution, pMX-human Neurogenin3 vector-derived viral solution, pMX-human Pdx1 vector-derived viral solution, and pMX-human MafA vector-derived viral solution, "dGNPM" represents the result in the case of using the (3) pMX-human mutated GLIS1 vector-derived viral solution, pMX-human Neurogenin3 vector-derived viral solution, pMX-human Pdx1 vector-derived viral solution, and pMX-human MafA vector-derived viral solution, "dGNM" represents the result in the case of using the (4) pMX-human mutated GLIS1 vector-derived viral solution, pMX-human Neurogenin3 vector-derived viral solution, and pMX-human MafA vector-derived viral solution, and "dGNP" represents the result in the case of using the (5) pMX-human mutated GLIS1 vector-derived viral solution, pMX-human Neurogenin3 vector-derived viral solution, and pMX-human Pdx1 vector-derived viral solution.

It was demonstrated from the results of FIG. 12 that the pancreatic endocrine cells were able to be produced efficiently using liver human cells in any case where factors according to any of aspects of the method of the present invention were used.

Test Example 13: Production of Pancreatic Endocrine Cells from Mouse Blood Cells <Preparation of Cells>

RAW264 cell line (RCB0535, available from Riken BioResource Research Center) were prepared as mouse blood cells.
<Production of Retrovirus>

The pMX-GFP vector-derived viral solution, the pMX-mouse GLIS1 vector-derived viral solution, the pMX-mouse mutated GLIS1 vector-derived viral solution, the pMX-mouse Neurogenin3 vector-derived viral solution, the pMX-mouse Pdx1 vector-derived viral solution, and the pMX-mouse MafA vector-derived viral solution were obtained in the same manner as in the Test Example 1-1 or 2-1.

INTRODUCTION

The gene was introduced into the cells in the same manner as in the Test Example 1-1, except that the viral solutions used in the Test Example 1-1 were changed to the following viral solutions.
[Viral Solution]
(1) pMX-GFP vector-derived viral solution (control)
(2) pMX-mouse GLIS1 vector-derived viral solution, pMX-mouse Neurogenin3 vector-derived viral solution, pMX-mouse Pdx1 vector-derived viral solution, and pMX-mouse MafA vector-derived viral solution
(3) pMX-mouse mutated GLIS1 vector-derived viral solution, pMX-mouse Neurogenin3 vector-derived viral solution, pMX-mouse Pdx1 vector-derived viral solution, and pMX-mouse MafA vector-derived viral solution
<Quantitative PCR Analysis>

Using the cells after the introduction and 3 days of culturing, the quantitative PCR analysis was performed in the same manner as in the Test Example 1-1.

Figure 13:
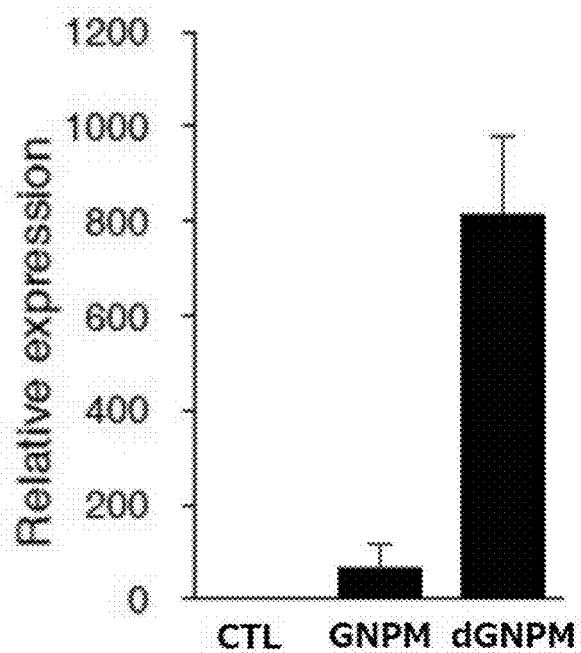
FIG. 13 is a graph illustrating the measurement results of a relative expression level of an insulin gene in Test Example 13.

The results are presented in FIG. 13. In FIG. 13, "CTL" represents the result in the case of using the (1) pMX-GFP vector-derived viral solution (control), "GNPM" represents the result in the case of using the (2) pMX-mouse GLIS1 vector-derived viral solution, pMX-mouse Neurogenin3 vector-derived viral solution, pMX-mouse Pdx1 vector-derived viral solution, and pMX-mouse MafA vector-derived viral solution, and "dGNPM" represents the result in the case of using the (3) pMX-mouse mutated GLIS1 vector-derived viral solution, pMX-mouse Neurogenin3 vector-derived viral solution, pMX-mouse Pdx1 vector-derived viral solution, and pMX-mouse MafA vector-derived viral solution.

It was demonstrated from the results of FIG. 13 that the pancreatic endocrine cells were able to be produced efficiently even using mouse blood cells by using four factors of GLIS1, Neurogenin3, Pdx1, and MafA or the mutated GLIS1, Neurogenin3, Pdx1, and MafA, which is one aspect of the method of the present invention.

Test Example 14: Production-4 of Pancreatic Endocrine Cells

<Preparation of Cells> dMEFs were prepared in the same manner as in the Test Example 1-1.

<Production of Retrovirus>

The pMX-GFP vector-derived viral solution, the pMX-mouse GLIS1 vector-derived viral solution, the pMX-mouse mutated GLIS1 vector-derived viral solution, the pMX-mouse Neurogenin3 vector-derived viral solution, the pMX-mouse Pdx1 vector-derived viral solution, and the pMX-mouse MafA vector-derived viral solution were obtained in the same manner as in the Test Example 1-1 or 2-1.

INTRODUCTION

The gene was introduced into the cells in the same manner as in the Test Example 1-1, except that the viral solutions used in the Test Example 1-1 were changed to the following viral solutions.

[Viral Solution]
(1) pMX-GFP vector-derived viral solution (control)
(2) pMX-mouse GLIS1 vector-derived viral solution, pMX-mouse Neurogenin3 vector-derived viral solution, pMX-mouse Pdx1 vector-derived viral solution, and pMX-mouse MafA vector-derived viral solution
(3) pMX-mouse mutated GLIS1 vector-derived viral solution, pMX-mouse Neurogenin3 vector-derived viral solution, pMX-mouse Pdx1 vector-derived viral solution, and pMX-mouse MafA vector-derived viral solution
(4) pMX-mouse Neurogenin3 vector-derived viral solution, pMX-mouse Pdx1 vector-derived viral solution, and pMX-mouse MafA vector-derived viral solution (5) pMX-mouse GLIS1 vector-derived viral solution
(6) pMX-mouse mutated GLIS1 vector-derived viral solution
(7) pMX-mouse Neurogenin3 vector-derived viral solution
(8) pMX-mouse Pdx1 vector-derived viral solution
(9) pMX-mouse MafA vector-derived viral solution <Determination of Number of dMEF-Derived Insulin Producing Cells>

The number of the DsRed2-positive insulin producing cells was counted in the same manner as in the Test Example 1-1, except that, after the introduction and 26 days of culturing, the DsRed2-positive insulin producing cells were photographed by a fluorescence microscope unit. The results are presented in FIG. 14.

Figure 14:
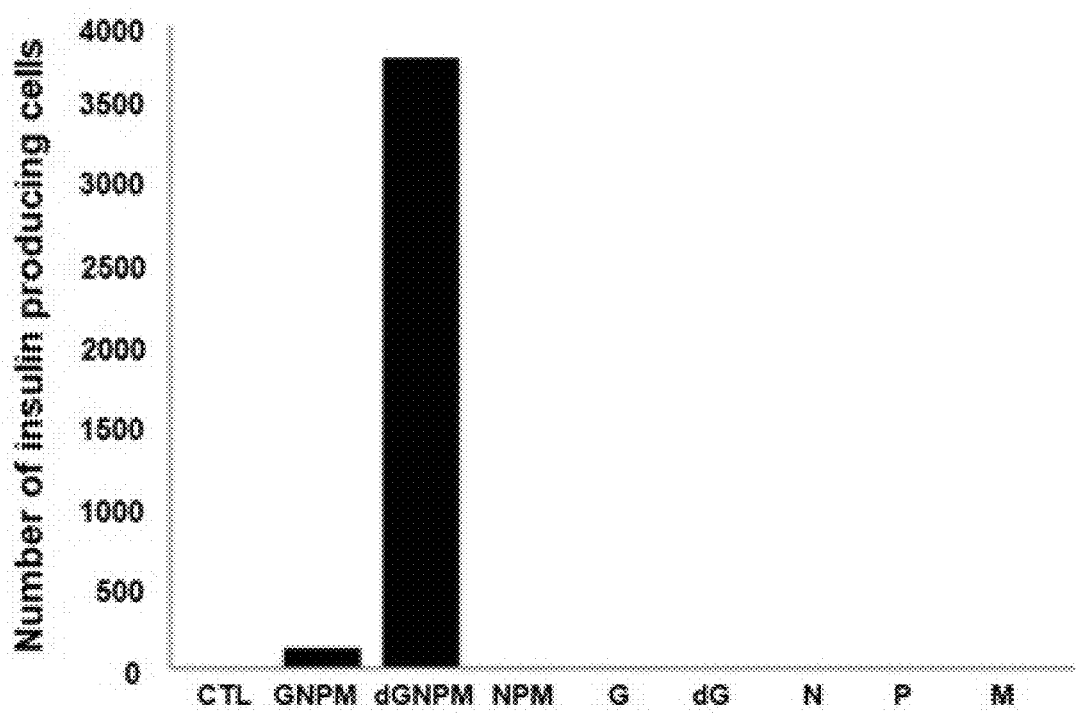
FIG. 14 is a graph illustrating the measurement results of the number of DsRed2-positive insulin producing cells in Test Example 14.

The results are presented in FIG. 14. In FIG. 14, "CTL" represents the result in the case of using the (1) pMX-GFP vector-derived viral solution (control), "GNPM" represents the result in the case of using the (2) pMX-mouse GLIS1 vector-derived viral solution, pMX-mouse Neurogenin3 vector-derived viral solution, pMX-mouse Pdx1 vector-derived viral solution, and pMX-mouse MafA vector-derived viral solution, "dGNPM" represents the result in the case of using the (3) pMX-mouse mutated GLIS1 vector-derived viral solution, pMX-mouse Neurogenin3 vector-derived viral solution, pMX-mouse Pdx1 vector-derived viral solution, and pMX-mouse MafA vector-derived viral solution, "NPM" represents the result in the case of using the (4) pMX-mouse Neurogenin3 vector-derived viral solution, pMX-mouse Pdx1 vector-derived viral solution, and pMX-mouse MafA vector-derived viral solution, "G" represents the result in the case of using the (5) pMX-mouse GLIS1 vector-derived viral solution, "dG" represents the result in the case of using the (6) pMX-mouse mutated GLIS1 vector-derived viral solution, "N" represents the result in the case of using the (7) pMX-mouse Neurogenin3 vector-derived viral solution, "P" represents the result in the case of using the (8) pMX-mouse Pdx1 vector-derived viral solution, and "M" represents the result in the case of using the (9) pMX-mouse MafA vector-derived viral solution.

From the results of FIG. 14, when using only one factor of GLIS1, mutated GLIS1, Neurogenin3, Pdx1, and MafA, pancreatic endocrine cells were not produced at all. Also when using only three factors of Neurogenin3, Pdx1, and MafA, pancreatic endocrine cells were not produced at all. Meanwhile, when using four factors of GLIS1 or mutated GLIS1 in addition to the three factors that were not able to produce pancreatic endocrine cells at all, excellent effects were demonstrated that pancreatic endocrine cells were able to be efficiently produced.

Test Example 15-1: Production-5-1 of Pancreatic Endocrine Cells

<Preparation of Cells>

The following five kinds of somatic cells were prepared.
(1) dMEFs were prepared in the same manner as in the Test Example 1-1.
(2) HEK293 cells (RCB1637, available from Riken BioResource Research Center) were prepared as human kidney cells.
(3) GLUTag cells (provided by Dr. Daniel J. Drucker of Mount Sinai Hospital) were prepared as mouse enterocytes.
(4) Human glioma T98G cell line (RCB1954, RIKEN) were prepared as human brain cells.
(5) HuH7 cells (RCB1366, available from Riken BioResource Research Center) were prepared as human liver cells.

<Production of Retrovirus>

Plat-GP cells in which viral structural proteins gag-pol and env, which were capable of producing high titer viruses for a long period of time, were expressed under the control of MoMuLV LTR and a plasmid DNA (pMX vector or pMX-puro vector, VSVG vector) were used to produce a retrovirus in the following manner (Onishi, M., et. al., Exp. Hematol. 24, 324-329, 1996).

—Preparation of Plasmid DNA—

[pMX-GFP Vector]

A pMX-GFP vector was prepared in the same manner as in the Test Example 1-1.

[pMX-Mouse Mutated GLIS1 Vector]

A pMX-mouse GLIS1 vector was prepared in the same manner as in the Test Example 2-1.

[pMX-Mouse Mutated GLIS1 (+192) Vector]

A pMX-mouse mutated GLIS1 (+192) is a vector in which the base sequence as set forth in SEQ ID NO: 1 including a base sequence as set forth in SEQ ID NO: 11 (sequence length: 192 bases) added to the 5'-terminus thereof is incorporated into the multi-cloning site of a pMX vector (available from Addgene).

The base sequence as set forth in SEQ ID NO: 1 including the base sequence as set forth in SEQ ID NO: 11 (sequence length: 192 bases) added to the 5'-terminus thereof is as set forth in SEQ ID NO: 12 and was prepared in the following manner. A schematic explanatory view of the base sequence as set forth in SEQ ID NO: 12 is presented in (d) of FIG. 15.

A DNA fragment as set forth in SEQ ID NO: 12, which is the base sequence as set forth in SEQ ID NO: 1 including the base sequence as set forth in SEQ ID NO: 11 (sequence length: 192 bases) added to the 5'-terminus thereof, was amplified by a PCR method using the pMX-mouse GLIS1 vector prepared in the Test Example 1-1 as a template DNA and using a forward primer as set forth in SEQ ID NO: 13 and a reverse primer as set forth in SEQ ID NO: 14, and PRIMESTAR (registered trademark) MAX DNA polymerase (available from Takara Bio Inc.). Then, the thus-amplified DNA fragments were purified through an agarose electrophoresis to thereby insert between a BamHI site and an XhoI site of the pMX vector. Abase sequence of the thus-inserted fragments was confirmed by a sequencing reaction.

[pMX-Mouse Mutated GLIS1 (+126) Vector]

A pMX-mouse mutated GLIS1 (+126) is a vector in which the base sequence as set forth in SEQ ID NO: 1 including a base sequence as set forth in SEQ ID NO: 15 (sequence length: 78 bases) added to the 5'-terminus thereof and a base sequence as set forth in SEQ ID NO: 16 (sequence length: 48 bases) added to the 3-terminus thereof is incorporated into the multi-cloning site of a pMX vector (available from Addgene).

The base sequence as set forth in SEQ ID NO: 1 including the base sequence as set forth in SEQ ID NO: 15 (sequence length: 78 bases) added to the 5'-terminus thereof and the base sequence as set forth in SEQ ID NO: 16 (sequence length: 48 bases) added to the 3'-terminus thereof is as set forth in SEQ ID NO: 17 and was prepared in the following manner. A schematic explanatory view of the base sequence as set forth in SEQ ID NO: 17 is presented in (e) of FIG. 15.

A DNA fragment as set forth in SEQ ID NO: 17, which is the base sequence as set forth in SEQ ID NO: 1 including the base sequence as set forth in SEQ ID NO: 15 (sequence length: 78 bases) added to the 5'-terminus thereof and the base sequence as set forth in SEQ ID NO: 16 (sequence length: 48 bases) added to the 3'-terminus thereof, was amplified by a PCR method using the pMX-mouse GLIS1 vector prepared in the Test Example 1-1 as a template DNA and using a forward primer as set forth in SEQ ID NO: 18 and a reverse primer as set forth in SEQ ID NO: 19, and PRIMESTAR (registered trademark) MAX DNA polymerase (available from Takara Bio Inc.). Then, the thus-amplified DNA fragments were purified through an agarose electrophoresis to thereby insert between a BamHI site and an XhoI site of the pMX vector. Abase sequence of the thus-inserted fragments was confirmed by a sequencing reaction.

[pMX-Mouse Neurogenin3 Vector]

The pMX-mouse Neurogenin3 vector was prepared in the same manner as in the Test Example 1-1.

[pMX-Mouse Pdx1 Vector]

The pMX-mouse Pdx1 vector was prepared in the same manner as in the Test Example 1-1.

[pMX-Mouse MafA Vector]

The pMX-mouse MafA vector was prepared in the same manner as in the Test Example 1-1.

—Production of Retrovirus—

A pMX-GFP vector-derived viral solution, a pMX-mouse mutated GLIS1 vector-derived viral solution, a pMX-mouse mutated GLIS1 (+192) vector-derived viral solution, a pMX-mouse mutated GLIS1 (+126) vector-derived viral solution, a pMX-mouse Neurogenin3 vector-derived viral solution, a pMX-mouse Pdx1 vector-derived viral solution, and a pMX-mouse MafA vector-derived viral solution were obtained in the same manner as in the Test Example 1-1, except that the plasmid DNAs used in the Test Example 1-1 were changed to plasmid DNAs for this Test Example.

INTRODUCTION

The gene was introduced into the cells in the same manner as in the Test Example 1-1, except that the viral solutions used in the Test Example 1-1 were changed to the following viral solutions.

[Viral Solution]

(1) pMX-GFP vector-derived viral solution (control)

(2) pMX-mouse GLIS1 vector-derived viral solution, pMX-mouse Neurogenin3 vector-derived viral solution, pMX-mouse Pdx1 vector-derived viral solution, and pMX-mouse MafA vector-derived viral solution (3) pMX-mouse GLIS1 (+192) vector-derived viral solution, pMX-mouse Neurogenin3 vector-derived viral solution, pMX-mouse Pdx1 vector-derived viral solution, and pMX-mouse MafA vector-derived viral solution (4) pMX-mouse GLIS1 (+126) vector-derived viral solution, pMX-mouse Neurogenin3 vector-derived viral solution, pMX-mouse Pdx1 vector-derived viral solution, and pMX-mouse MafA vector-derived viral solution <Quantitative PCR Analysis>

After the introduction and after 14 days of culturing for the dMEF, 4 days of culturing for the HEK293 cells, human glioma T98G cell line, and the HuH7 cells, or 7 days of culturing for the GLUTag cells, the respective cells were subjected to quantitative PCR analysis in the same manner as in the Test Example 1-1.

Figure 16A:
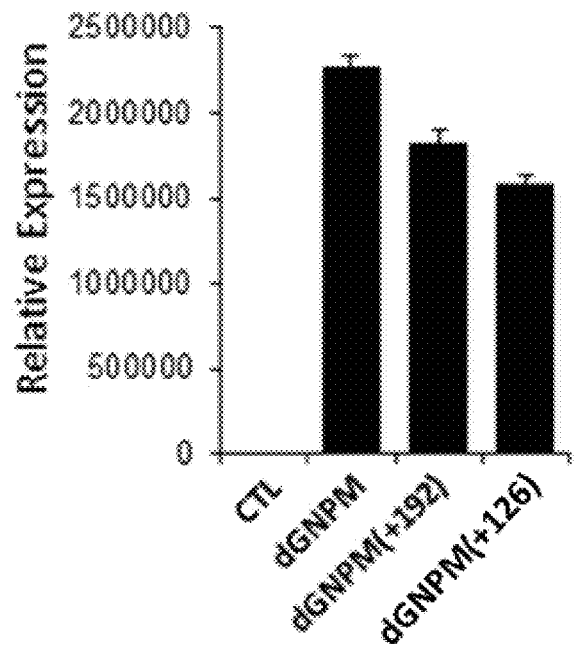
FIG. 16A is a graph illustrating the measurement results of a relative expression level of an insulin gene when using dMEF in Test Example 15-1.
Figure 16B:
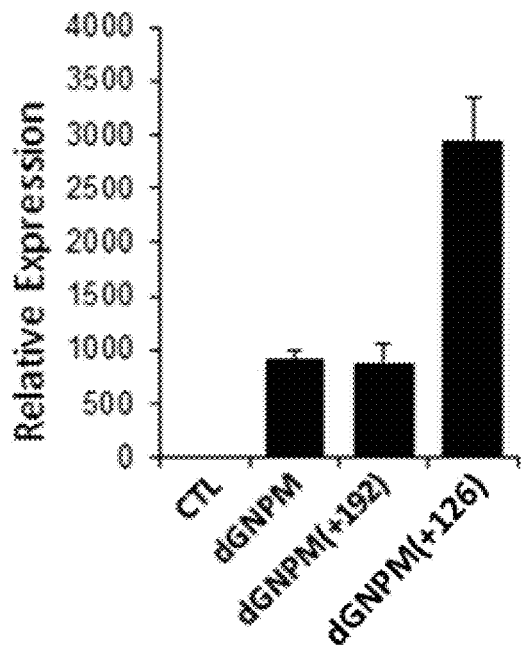
FIG. 16B is a graph illustrating the measurement results of a relative expression level of an insulin gene when using HEK293 cells in Test Example 15-1.
Figure 16C:
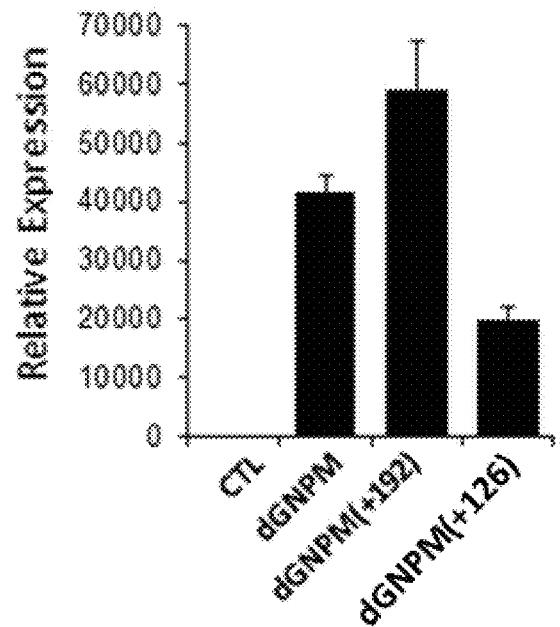
FIG. 16C is a graph illustrating the measurement results of a relative expression level of an insulin gene when using GLUTag cells in Test Example 15-1.
Figure 16D:
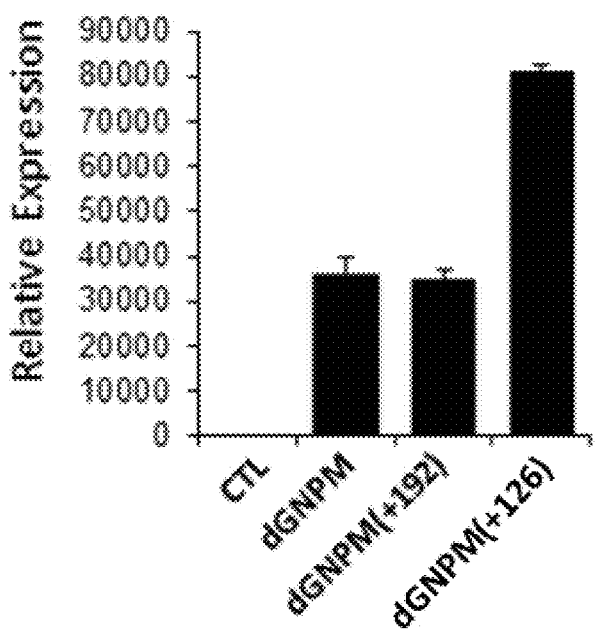
FIG. 16D is a graph illustrating the measurement results of a relative expression level of an insulin gene when using human glioma T98G cell line in Test Example 15-1.
Figure 16E:
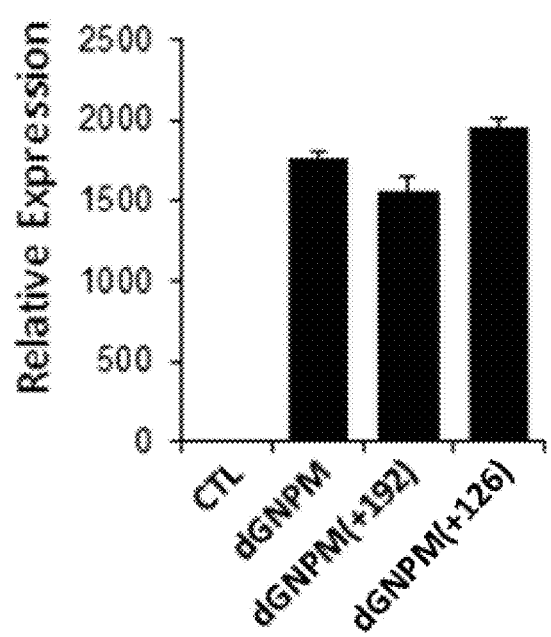
FIG. 16E is a graph illustrating the measurement results of a relative expression level of an insulin gene when using HuH7 cell line in Test Example 15-1.

The result in the case of using the dMEF is presented in FIG. 16A, the result in the case of using the HEK293 cells is presented in FIG. 16B, the result in the case of using the GLUTag cells is presented in FIG. 16C, the result in the case of using the human glioma T98G cell line is presented in FIG. 16D, and the result in the case of using the HuH7 cells is presented in FIG. 16E.

In FIG. 16A to FIG. 16E, "CTL" represents the result in the case of using the (1) pMX-GFP vector-derived viral solution (control), "dGNPM" represents the result in the case of using the (2) pMX-mouse GLIS1 vector-derived viral solution, pMX-mouse Neurogenin3 vector-derived viral solution, pMX-mouse Pdx1 vector-derived viral solution, and pMX-mouse MafA vector-derived viral solution, "dGNPM(+192)" represents the result in the case of using the (3) pMX-mouse GLIS1 (+192) vector-derived viral solution, pMX-mouse Neurogenin3 vector-derived viral solution, pMX-mouse Pdx1 vector-derived viral solution, and pMX-mouse MafA vector-derived viral solution, and "dGNPM(+126)" represents the result in the case of using the (4) pMX-mouse GLIS1 (+126) vector-derived viral solution, pMX-mouse Neurogenin3 vector-derived viral solution, pMX-mouse Pdx1 vector-derived viral solution, and pMX-mouse MafA vector-derived viral solution.

It was demonstrated from the results of FIG. 16A to FIG. 16E that pancreatic endocrine cells were able to be efficiently produced even when a mutated GLIS1 gene or one or more gene products thereof having a sequence identity of about 85% to the base sequence of SEQ ID NO: 1 (i.e., pMX-mouse mutated GLIS1 (+192) vector-derived viral solution) or a mutated GLIS1 gene or one or more gene products thereof having a sequence identity of about 90% to the base sequence of SEQ ID NO: 1 (i.e., pMX-mouse mutated GLIS1 (+126) vector-derived viral solution) was used as the mutated GLIS1 gene or one or more gene products thereof.

Test Example 15-2: Production-5-2 of Pancreatic Endocrine Cells

<Preparation of Cells> dMEFs were prepared in the same manner as in the Test Example 1-1.

<Preparation of Retrovirus>

Plat-GP cells in which viral structural proteins gag-pol and env, which were capable of producing high titer viruses for a long period of time, were expressed under the control of MoMuLV LTR and a plasmid DNA (pMX vector or pMX-puro vector, VSVG vector) were used to produce a retrovirus in the following manner (Onishi, M., et. al., Exp. Hematol. 24, 324-329, 1996).

—Preparation of Plasmid DNA—

[pMX-GFP Vector]

The pMX-GFP vector was prepared in the same manner as in the Test Example 1-1.

[pMX-Mouse GLIS1 Vector]

The pMX-mouse GLIS1 vector was prepared in the same manner as in the Test Example 1-1.

[pMX-Mouse Neurogenin3 Vector]

The pMX-mouse Neurogenin3 vector was prepared in the same manner as in the Test Example 1-1.

[pMX-Mouse Pdx1 Vector]

The pMX-mouse Pdx1 vector was prepared in the same manner as in the Test Example 1-1.

[pMX-Mouse Mutated GLIS1 Vector]

The pMX-mouse mutated GLIS1 vector was prepared in the same manner as in the Test Example 2-1.

[pMX-Mouse GLIS1 (−600) Vector]

The pMX-mouse GLIS1 (−600) vector is a vector in which a gene coding for a protein in which 200 amino acid residues at N-terminus of a mouse GLIS1 protein are deleted is incorporated into the multi-cloning site of a pMX vector (available from Addgene). The sequence of the gene coding for the protein in which 200 amino acid residues at N-terminus of the mouse GLIS1 protein are deleted is a base sequence generated by deletion of 600 bases from the 5'-terminus of the base sequence deposited under Accession Number NM_147221 (NCBI). This base sequence corresponds to the base sequence of mouse mutated GLIS1 as set forth in SEQ ID NO: 1 including 480 bases added to the 5'-terminus thereof (i.e., a base sequence having a sequence identity of less than 85% to the base sequence as set forth in SEQ ID NO: 1).

The sequence of the gene coding for the protein in which 200 amino acid residues at N-terminus of the mouse GLIS1 protein are deleted is as set forth in SEQ ID NO: 20 and was prepared in the following manner. A schematic explanatory view of the base sequence as set forth in SEQ ID NO: 20 is presented in (c) of FIG. 15.

A DNA fragment coding for the protein in which 200 amino acid residues at N-terminus of the mouse GLIS1 protein are deleted was amplified by a PCR method using the pMX-mouse GLIS1 vector prepared in the Test Example 1-1 as a template DNA and using a forward primer as set forth in SEQ ID NO: 21 and a reverse primer as set forth in SEQ ID NO: 22, and PRIMESTAR (registered trademark) MAX DNA polymerase (available from Takara Bio Inc.). Then, the thus-amplified DNA fragments were purified through an agarose electrophoresis to thereby insert between a BamHI site and an XhoI site of the pMX vector. A base sequence of the thus-inserted fragments was confirmed by a sequencing reaction.

[pMX-Mouse GLIS1 (−1,470) Vector]

The pMX-mouse GLIS1 (−1,470) vector is a vector in which a gene coding for a protein in which 490 amino acid residues at N-terminus of a mouse GLIS1 protein are deleted is incorporated into the multi-cloning site of the pMX vector (available from Addgene). The sequence of the gene coding for the protein in which 490 amino acid residues at N-terminus of the mouse GLIS1 protein are deleted is a base sequence generated by deletion of 1,470 bases from the 5-terminus of the base sequence deposited under Accession Number NM_147221 (NCBI). This base sequence corresponds to the base sequence of mouse mutated GLIS1 as set forth in SEQ ID NO: 1 from which 390 bases are deleted from the 5'-terminus thereof (i.e., a base sequence having a sequence identity of less than 85% to the base sequence as set forth in SEQ ID NO: 1).

The sequence of the gene coding for the protein in which 490 amino acid residues at N-terminus of the mouse GLIS1 protein are deleted is as set forth in SEQ ID NO: 23 and was prepared in the following manner. A schematic explanatory view of the base sequence as set forth in SEQ ID NO: 23 is presented in (f) of FIG. 15.

A DNA fragment coding for the protein in which 490 amino acid residues at N-terminus of the mouse GLIS1 protein are deleted was amplified by a PCR method using the pMX-mouse GLIS1 vector prepared in the Test Example 1-1 as a template DNA and using a forward primer as set forth in SEQ ID NO: 24 and a reverse primer as set forth in SEQ ID NO: 25, and PRIMESTAR (registered trademark) MAX DNA polymerase (available from Takara Bio Inc.). Then, the thus-amplified DNA fragments were purified through an agarose electrophoresis to thereby insert between a BamHI site and an XhoI site of the pMX vector. A base sequence of the thus-inserted fragments was confirmed by a sequencing reaction.

[pMX-Mouse GLIS1 (−747) Vector]

The pMX-mouse GLIS1 (−747) vector is a vector in which a gene coding for a protein in which 249 amino acid residues at C-terminus of a mouse GLIS1 protein are deleted is incorporated into the multi-cloning site of a pMX vector (available from Addgene). The sequence of the gene coding for the protein in which 249 amino acid residues at C-terminus of the mouse GLIS1 protein are deleted is a base sequence in which 747 bases are deleted from the 3'-terminus of the base sequence deposited under Accession Number NM_147221 (NCBI).

The sequence of the gene coding for the protein in which 249 amino acid residues at C-terminus of the mouse GLIS1 protein are deleted is as set forth in SEQ ID NO: 26 and was prepared in the following manner. A schematic explanatory view of the base sequence as set forth in SEQ ID NO: 26 is presented in (g) of FIG. 15.

A DNA fragment coding for the protein in which 249 amino acid residues at C-terminus of the mouse GLIS1 protein are deleted was amplified by a PCR method using the pMX-mouse GLIS1 vector prepared in the Test Example 1-1 as a template DNA and using a forward primer as set forth in SEQ ID NO: 27 and a reverse primer as set forth in SEQ ID NO: 28, and PRIMESTAR (registered trademark) MAX DNA polymerase (available from Takara Bio Inc.). Then, the thus-amplified DNA fragments were purified through an agarose electrophoresis to thereby insert between a BamHI site and an XhoI site of the pMX vector. A base sequence of the thus-inserted fragments was confirmed by a sequencing reaction.

[pMX-Mouse GLIS1 (−897) Vector]

The pMX-mouse GLIS1 (−897) vector is a vector in which a gene coding for a protein in which 299 amino acid residues at C-terminus of a mouse GLIS1 protein are deleted is incorporated into the multi-cloning site of a pMX vector (available from Addgene). The sequence of the gene coding for the protein in which 299 amino acid residues at C-terminus of the mouse GLIS1 protein are deleted is a base sequence generated by deletion of 897 bases from 3'-terminus of the base sequence deposited under Accession Number NM_147221 (NCBI).

The sequence coding for the protein in which 299 amino acid residues at C-terminus of the mouse GLIS1 protein are deleted is as set forth in SEQ ID NO: 29 and was prepared in the following manner. A schematic explanatory view of the base sequence as set forth in SEQ ID NO: 29 is presented in (h) of FIG. 15.

A DNA fragment coding for the protein in which 299 amino acid residues at C-terminus of the mouse GLIS1 protein are deleted was amplified by a PCR method using the pMX-mouse GLIS1 vector prepared in the Test Example 1-1 as a template DNA and using a forward primer as set forth in SEQ ID NO: 30 and a reverse primer as set forth in SEQ ID NO: 31, and PRIMESTAR (registered trademark) MAX DNA polymerase (available from Takara Bio Inc.). Then, the thus-amplified DNA fragments were purified through an agarose electrophoresis to thereby insert between a BamHI site and an XhoI site of the pMX vector. A base sequence of the thus-inserted fragments was confirmed by a sequencing reaction.

[pMX-Mouse GLIS1 Δ ZFD Vector]

The pMX-mouse GLIS1 Δ ZFD vector is a vector in which a gene coding for a protein in which 145 amino acids of the zinc finger domain (ZFD) of a mouse GLIS1 protein are deleted is incorporated into the multi-cloning site of a pMX vector (obtained from Toshio Kitamura at THE INSTITUTE OF MEDICAL SCIENCE, THE UNIVERSITY OF TOKYO). In other words, this is a vector in which the base sequence of mouse GLIS1 deposited under Accession Number NM_147221 from which a base sequence as set forth in SEQ ID NO: 32 (sequence length: 435 bases) present in a range of from 1.096 bases to 1,530 bases from the 5'-terminus of the base sequence of the mouse GLIS1 is deleted is incorporated into the multi-cloning site of the pMX vector.

The sequence of the gene coding for the protein in which 145 amino acids of the zinc finger domain (ZFD) of the mouse GLIS1 protein are deleted is as set forth in SEQ ID NO: 33 and was prepared in the following manner. A schematic explanatory view of the base sequence as set forth in SEQ ID NO: 33 is presented in (i) of FIG. 15.

A DNA fragment coding for the protein in which the ZFD of the mouse GLIS1 protein is deleted was amplified by a PCR method using the pMX-mouse GLIS1 vector prepared in the Test Example 1-1 as a template DNA and using a forward primer as set forth in SEQ ID NO: 34 and a reverse primer as set forth in SEQ ID NO: 35 and a forward primer as set forth in SEQ ID NO: 36 and a reverse primer as set forth in SEQ ID NO: 37, and PRIMESTAR (registered trademark) MAX DNA polymerase (available from Takara Bio Inc.). Then, the thus-amplified DNA fragments were purified through an agarose electrophoresis to thereby insert between a BamHI site and an XhoI site of the pMX vector. A base sequence of the thus-inserted fragments was confirmed by a sequencing reaction.

—Production of Retrovirus—

A pMX-GFP vector-derived viral solution, a pMX-mouse GLIS1 vector-derived viral solution, a pMX-mouse Neurogenin3 vector-derived viral solution, a pMX-mouse Pdx1 vector-derived viral solution, a pMX-mouse mutated GLIS1 vector-derived viral solution, a pMX-mouse GLIS1 (−600) vector-derived viral solution, a pMX-mouse GLIS1 (−1,470) vector-derived viral solution, a pMX-mouse GLIS1 (−747) vector-derived viral solution, a pMX-mouse GLIS1 (−897) vector-derived viral solution, and a pMX-mouse GLIS1ΔZFD vector-derived viral solution were obtained in the same manner as in the Test Example 1-1, except that the plasmid DNAs used in the Test Example 1-1 were changed to plasmid DNAs for this Test Example.

INTRODUCTION

The gene was introduced into the cells in the same manner as in the Test Example 1-1, except that the viral solutions used in the Test Example 1-1 were changed to the following viral solutions.

[Viral Solution]
(1) pMX-GFP vector-derived viral solution (control)
(2) pMX-mouse GLIS1 vector-derived viral solution, pMX-mouse Neurogenin3 vector-derived viral solution, and pMX-mouse Pdx1 vector-derived viral solution
(3) pMX-mouse mutated GLIS1 vector-derived viral solution, pMX-mouse Neurogenin3 vector-derived viral solution, and pMX-mouse Pdx1 vector-derived viral solution
(4) pMX-mouse GLIS1 (−600) vector-derived viral solution, pMX-mouse Neurogenin3 vector-derived viral solution, and pMX-mouse Pdx1 vector-derived viral solution
(5) pMX-mouse GLIS1 (−1,470) vector-derived viral solution, pMX-mouse Neurogenin3 vector-derived viral solution, and pMX-mouse Pdx1 vector-derived viral solution
(6) pMX-mouse GLIS1 (−747) vector-derived viral solution, pMX-mouse Neurogenin3 vector-derived viral solution, and pMX-mouse Pdx1 vector-derived viral solution
(7) pMX-mouse GLIS1 (−897) vector-derived viral solution, pMX-mouse Neurogenin3 vector-derived viral solution, and pMX-mouse Pdx1 vector-derived viral solution
(8) pMX-mouse GLIS1 Δ ZFD vector-derived viral solution, pMX-mouse Neurogenin3 vector-derived viral solution, and pMX-mouse Pdx1 vector-derived viral solution <Determination of Number of dMEF-Derived Insulin Producing Cells>

The number of the DsRed2-positive insulin producing cells was counted in the same manner as in the Test Example 1-1, except that, after the introduction and 18 days of culturing, the DsRed2-positive insulin producing cells were photographed by a fluorescence microscope unit. The results are presented in FIG. 17.

Figure 17:
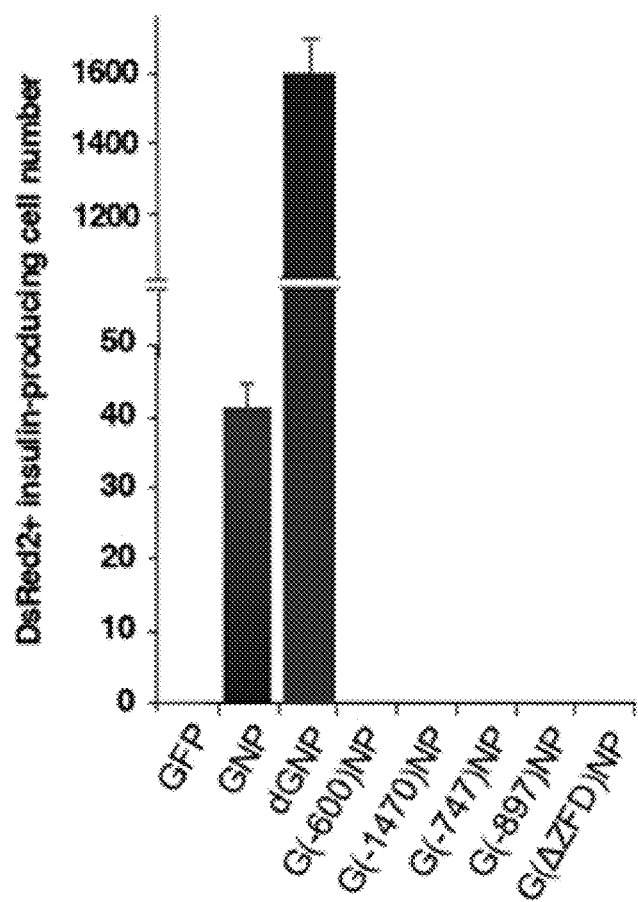
FIG. 17 is a graph illustrating the measurement results of the number of DsRed2-positive insulin producing cells in Test Example 15-2.

The results are presented in FIG. 17. In FIG. 17, "CTL" represents the result in the case of using the (1) pMX-GFP vector-derived viral solution (control), "GNP" represents the result in the case of using the (2) pMX-mouse GLIS1 vector-derived viral solution, pMX-mouse Neurogenin3 vector-derived viral solution, and pMX-mouse Pdx1 vector-derived viral solution, "dGNP" represents the result in the case of using the (3) pMX-mouse mutated GLIS1 vector-derived viral solution, pMX-mouse Neurogenin3 vector-derived viral solution, and pMX-mouse Pdx1 vector-derived viral solution, "G(−600)NP" represents the result in the case of using the (4) pMX-mouse GLIS1 (−600) vector-derived viral solution, pMX-mouse Neurogenin3 vector-derived viral solution, and pMX-mouse Pdx1 vector-derived viral solution, "G(−1,470)NP" represents the result in the case of using the (5) pMX-mouse GLIS1 (−1,470) vector-derived viral solution, pMX-mouse Neurogenin3 vector-derived viral solution, and pMX-mouse Pdx1 vector-derived viral solution, "G(−747)NP" represents the result in the case of using the (6) pMX-mouse GLIS1 (−747) vector-derived viral solution, pMX-mouse Neurogenin3 vector-derived viral solution, and pMX-mouse Pdx1 vector-derived viral solution, "G(−897)NP" represents the result in the case of using the (7) pMX-mouse GLIS1 (−897) vector-derived viral solution, pMX-mouse Neurogenin3 vector-derived viral solution, and pMX-mouse Pdx1 vector-derived viral solution, and "G(A ZFD)NP" represents the result in the case of using the (8) pMX-mouse GLIS1 AZFD vector-derived viral solution, pMX-mouse Neurogenin3 vector-derived viral solution, and pMX-mouse Pdx1 vector-derived viral solution.

From the results of FIG. 17, pancreatic endocrine cells were not able to be produced when the mutated GLIS1 as set forth in SEQ ID NO: 1 was mutated so as to have a sequence identity of less than 85%.

Meanwhile, from the results of FIG. 17 and FIG. 16A to FIG. 16E, it was suggested that pancreatic endocrine cells were able to be efficiently produced when the mutated GLIS1 as set forth in SEQ ID NO: 1 was mutated so as to have a sequence identity of 85% or more.

Test Example 16-1: Production-1 of Pancreatic Endocrine Cells In Vivo

The pMX-mouse GLIS1 vector, pMX-mouse Neurogenin3 vector, pMX-mouse Pdx1 vector, and pMX-mouse MafA vector produced in the same manner as in Test Example 1-1 were intravenously administered at 20 µg/dose to the tail of the genetically modified mice produced in Test Example 1-1 in which pancreatic β cells were fluorescently labeled with DsRed2 (Ins-DsR, 12 weeks old). After 14 days, the liver and the spleen of the mouse were removed.

The liver and the spleen of the mouse, which had been removed, were fixed with 4% by volume paraformaldehyde (PFA) 4° C. overnight. After that, immunofluorescence staining was performed using an anti-insulin antibody (A0564; Polyclonal Guinea Pig Anti-Insulin, available from DAKO Co.) and a nucleus staining agent (Dapi, D9542, available from SIGMA Co.).

The DsRed2-positive insulin producing cells in the liver and the spleen of the mouse, which had been removed, were photographed by a fluorescence microscope (CARL ZEISS AXIOVERT 200M) unit. The result of phase-contrast imaging is presented in FIG. 18A, the result of the DsRed2-positive insulin producing cells by fluorescence imaging is presented in FIG. 18B, and the result of immunofluorescence staining is presented in and FIG. 18C.

Figure 18A:
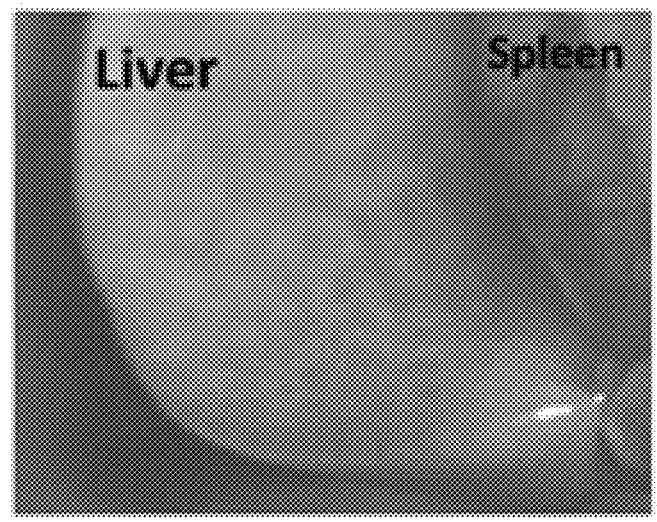
FIG. 18A is an image obtained by phase-contrast imaging of the liver and the spleen removed from a mouse in Test Example 16-1.
Figure 18B:
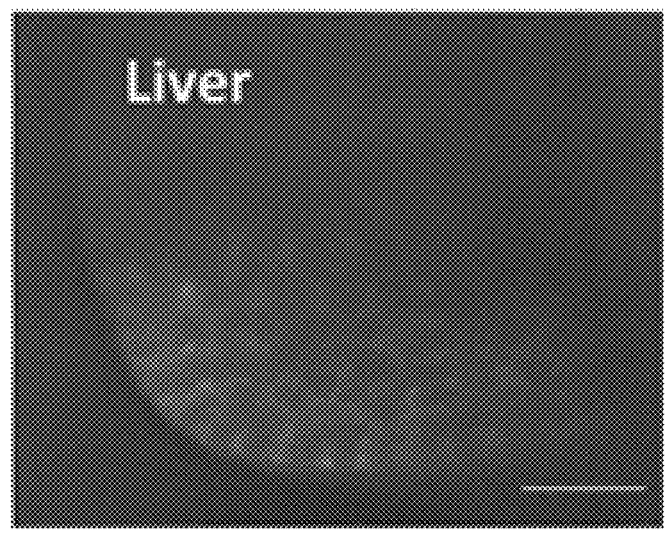
FIG. 18B is an image of DsRed2-positive insulin producing cells obtained by fluorescence imaging of the liver and the spleen removed from a mouse in Test Example 16-1.
Figure 18C:
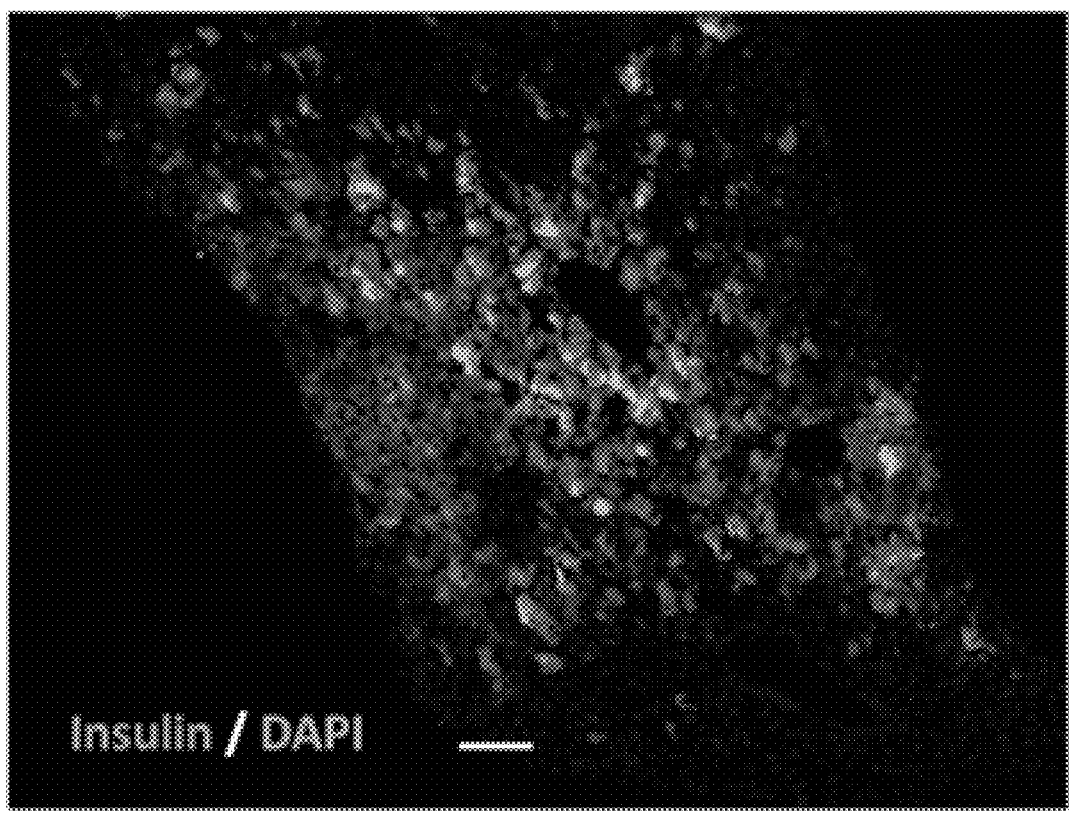
FIG. 18C is an image illustrating the results of immunofluorescence staining of the liver and the spleen removed from a mouse in Test Example 16-1.

It was demonstrated from the results of FIG. 18A to FIG. 18C that the production efficiency of pancreatic endocrine cells remarkably increased also in vivo similar to in vitro.

Test Example 16-2: Production-2 of Pancreatic Endocrine Cells In Vivo

<Preparation of mRNA>
[Mouse Mutated GLIS1 mRNA]

The pMX-mouse mutated GLIS1 vector was prepared in the same manner as in the Test Example 2-1.

The mouse mutated GLIS1 mRNA was prepared from the above-prepared pMX-mouse mutated GLIS1 vector using mMEDSSAGE mMACHINE T7 ULTRA Transcription Kit (available from Invitrogen Co.).
[Mouse Neurogenin3 mRNA]

The pMX-mouse Neurogenin3 vector was prepared in the same manner as in the Test Example 1-1.

The mouse Neurogenin3 mRNA was prepared from the above-prepared pMX-mouse Neurogenin3 vector using mMEDSSAGE mMACHINE T7 ULTRA Transcription Kit (available from Invitrogen Co.).
[Mouse Pdx1 mRNA]

The pMX-mouse Pdx1 vector was prepared in the same manner as in the Test Example 1-1.

The mouse Pdx1 mRNA was prepared from the above-prepared pMX-mouse Pdx1 vector using mMEDSSAGE mMACHINE T7 ULTRA Transcription Kit (available from Invitrogen Co.).
[Mouse MafA mRNA]

The pMX-mouse MafA vector was prepared in the same manner as in the Test Example 1-1.

The mouse MafA mRNA was prepared from the above-prepared pMX-mouse MafA vector using mMEDSSAGE mMACHINE T7 ULTRA Transcription Kit (available from Invitrogen Co.).

INTRODUCTION

The mouse mutated GLIS1 mRNA, the mouse Neurogenin3 mRNA, the mouse Pdx1 mRNA, and the mouse MafA mRNA were intravenously administered at 10 µg/dose to the tail of the genetically modified mice produced in Test Example 1-1 in which pancreatic β cells were fluorescently labeled with DsRed2 (Ins-DsR, 14 weeks old). After 18 days, the liver of the mouse was removed.

The DsRed2-positive insulin producing cells in the liver of the mouse, which had been removed, were photographed by a fluorescence microscope (CARL ZEISS AXIOVERT 200M) unit. The result of phase-contrast imaging is presented in FIG. 19A, and the result of the DsRed2-positive insulin producing cells by fluorescence imaging is presented in FIG. 19B.

Figure 19A:
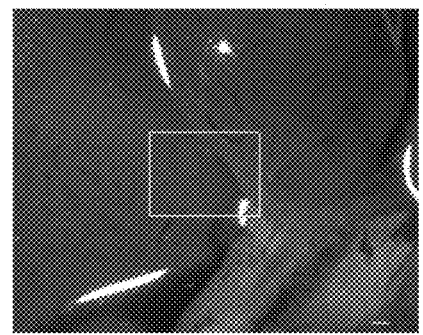
FIG. 19A is an image obtained by phase-contrast imaging of the liver removed from a mouse in Test Example 16-2.
Figure 19B:
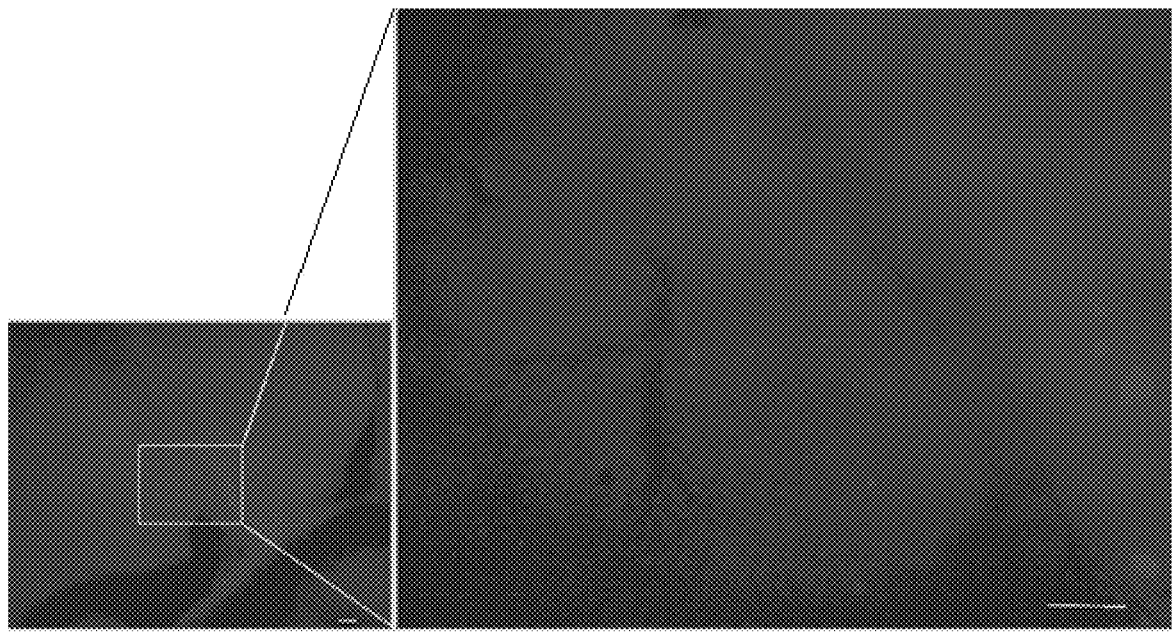
FIG. 19B is an image of DsRed2-positive insulin producing cells obtained by fluorescence imaging of the liver removed from a mouse in Test Example 16-2.

It was demonstrated from the results of FIG. 19A and FIG. 19B that the production efficiency of pancreatic endocrine cells remarkably increased also in vivo similar to in vitro.

Test Example 17: Production-6 of Pancreatic Endocrine Cells

<Preparation of Cells>
dMEFs were prepared in the same manner as in the Test Example 1-1.
<Preparation of Retrovirus>

A pMX-mouse mutated GLIS1 vector-derived viral solution, a pMX-mouse Neurogenin3 vector-derived viral solution, a pMX-mouse Pdx1 vector-derived viral solution, and a pMX-mouse MafA vector-derived viral solution were obtained in the same manner as in Test Example 1-1 or 2-1.

INTRODUCTION

The gene was introduced into the cells in the same manner as in the Test Example 1-1, except that the viral solutions used in the Test Example 1-1 were changed to the following viral solutions.
[Viral Solution]
(1) pMX-mouse mutated GLIS1 vector-derived viral solution, pMX-mouse Neurogenin3 vector-derived viral solution, pMX-mouse Pdx1 vector-derived viral solution, and pMX-mouse MafA vector-derived viral solution After the introduction and 21 days of culturing, the cells were fixed with 4% by volume paraformaldehyde (PFA) 4° C. overnight. After that, immunofluorescence staining was performed using an anti-insulin antibody (A0564; Polyclonal Guinea Pig Anti-Insulin, available from DAKO Co.), an anti-glucagon antibody (A0565; Polyclonal Rabbit Anti-Human Glucagon, available from DAKO Co.), and a nucleus staining agent (Dapi, D9542, available from SIGMA Co.).

Figure 20:
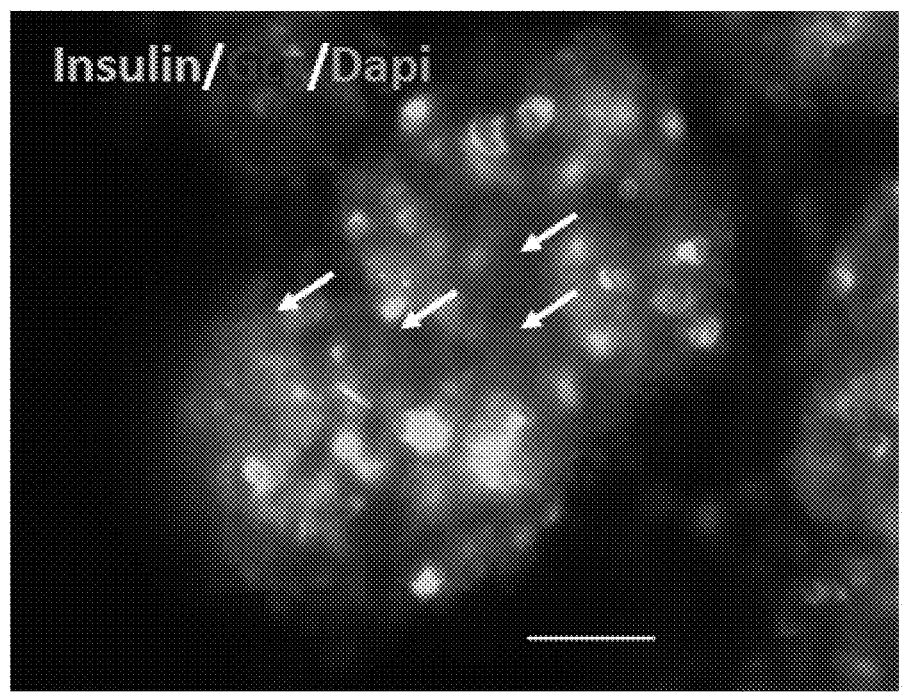
FIG. 20 is an image illustrating the results of immunofluorescence staining in Test Example 17.

The cells that had undergone immunofluorescence staining were photographed by a fluorescence microscope (CARL ZEISS AXIOVERT 200M) unit. The results of the insulin-producing cells and glucagon-producing cells by fluorescence imaging are presented in FIG. 20. In FIG. 20, the arrows each indicate a glucagon producing cell.

Test Example 18: Sequence Identity Analysis

The sequence identity between the base sequence (1,290 bases) of the mouse mutated GLIS1 gene as set forth in SEQ ID NO: 1 and the base sequence (1,299 bases) of the human mutated GLIS1 gene as set forth in SEQ ID NO: 2 was analyzed using gene analysis software (GENETYX-MAC (version 18.0.6)). The results are presented in FIG. 21A and FIG. 21B.

In the gene analysis results presented in FIG. 21A and FIG. 21B, "Query" indicates the base sequence as set forth in SEQ ID NO: 1, "Sbjct" indicates the base sequence as set forth in SEQ ID NO: 2, "*" indicates that the base of Query and the is base of Sbjct are identical.

As presented in FIG. 21A and FIG. 21B, the identical bases between the base sequence of the mouse mutated GLIS1 gene as set forth in SEQ ID NO: 1 and the base sequence of the human mutated GLIS1 gene as set forth in SEQ ID NO: 2 are 1,095 bases. The base sequence of the human mutated GLIS1 gene as set forth in SEQ ID NO: 2 was found to have a sequence identity of 84.88% to the base sequence of the mouse mutated GLIS1 gene as set forth in SEQ ID NO: 1. The base sequence of the mouse mutated GLIS1 gene as set forth in SEQ ID NO: 1 was found to have a sequence identity of 84.30% to the base sequence of the human mutated GLIS1 gene as set forth in SEQ ID NO: 2.

A method for producing pancreatic endocrine cells according to the present invention is simple and is easily reproduced compared to previous methods in which pancreatic endocrine cells are produced using ES cells or iPS cells under a culturing environment properly adjusted, for example, by adding a development inhibitor to a medium. According to the method of the present invention, the pancreatic endocrine cells are capable of being very efficiently produced. Moreover, the pancreatic endocrine cells are capable of being produced in a much shorter period of time.

The method of the present invention is also advantageous in that the pancreatic endocrine cells are capable of being produced without undergoing the iPS cell stage that has a risk of forming tumors.

Therefore, the method for producing pancreatic endocrine cells according to the present invention is suitably available for, for example, producing pancreatic endocrine cells to be used in regenerative therapies for diabetes.

Aspects of the present invention are, for example, as follows.
<1> A method for producing pancreatic endocrine cells, the method including
introducing (A), (B), (C), or (D) below into somatic cells:
(A) a mutated GLIS1 gene having a sequence identity of 85% or more to a base sequence as set forth in SEQ ID NO: 1 or 2 or one or more gene products thereof, a Neurogenin3 gene or one or more gene products thereof, a Pdx1 gene or one or more gene products thereof, and a MafA gene or one or more gene products thereof;
(B) a mutated GLIS1 gene having a sequence identity of 85% or more to a base sequence as set forth in SEQ ID NO: 1 or 2 or one or more gene products thereof, a Neurogenin3 gene or one or more gene products thereof, and a Pdx1 gene or one or more gene products thereof:
(C) a GLIS1 gene or one or more gene products thereof, a Neurogenin3 gene or one or more gene products thereof, a Pdx1 gene or one or more gene products thereof, and a MafA gene or one or more gene products thereof; and
(D) a mutated GLIS1 gene having a sequence identity of 85% or more to a base sequence as set forth in SEQ ID NO: 1 or 2 or one or more gene products thereof, a Neurogenin3 gene or one or more gene products thereof, and a MafA gene or one or more gene products thereof.
<2> The method for producing pancreatic endocrine cells according to <1>, wherein (A), (B), (C), or (D) to be introduced into the somatic cells is (A) a mutated GLIS1 gene having a sequence identity of 85% or more to a base sequence as set forth in SEQ ID NO: 1 or 2 or one or more gene products thereof, a Neurogenin3 gene or one or more gene products thereof, a Pdx1 gene or one or more gene products thereof, and a MafA gene or one or more gene products thereof.
<3> The method for producing pancreatic endocrine cells according to <1>, wherein (A), (B), (C), or (D) to be introduced into the somatic cells is (B) a mutated GLIS1 gene having a sequence identity of 85% or more to a base sequence as set forth in SEQ ID NO: 1 or 2 or one or more gene products thereof, a Neurogenin3 gene or one or more gene products thereof, and a Pdx1 gene or one or more gene products thereof.
<4> The method for producing pancreatic endocrine cells according to <1>, wherein (A), (B), (C), or (D) to be introduced into the somatic cells is (C) a GLIS1 gene or one or more gene products thereof, a Neurogenin3 gene or one or more gene products thereof, a Pdx1 gene or one or more gene products thereof, and a MafA gene or one or more gene products thereof.
<5> The method for producing pancreatic endocrine cells according to <1>, wherein (A), (B), (C), or (D) to be introduced into the somatic cells is (D) a mutated GLIS1 gene having a sequence identity of 85% or more to a base sequence as set forth in SEQ ID NO: 1 or 2 or one or more gene products thereof, a Neurogenin3 gene or one or more gene products thereof, and a MafA gene or one or more gene products thereof.
<6> The method for producing pancreatic endocrine cells according to any one of <1> to <5>, wherein the somatic cells are fibroblasts or mesenchymal stem cells.
<7> The method for producing pancreatic endocrine cells according to any one of <1> to <6>, wherein the pancreatic endocrine cells are β cells.
<8> A transdifferentiation agent including (A), (B), (C), or (D) below:
(A) a mutated GLIS1 gene having a sequence identity of 85% or more to a base sequence as set forth in SEQ ID NO: 1 or 2 or one or more gene products thereof, a Neurogenin3 gene or one or more gene products thereof, a Pdx1 gene or one or more gene products thereof, and a MafA gene or one or more gene products thereof;
(B) a mutated GLIS1 gene having a sequence identity of 85% or more to a base sequence as set forth in SEQ ID NO: 1 or 2 or one or more gene products thereof, a Neurogenin3 gene or one or more gene products thereof, and a Pdx1 gene or one or more gene products thereof:

(C) a GLIS1 gene or one or more gene products thereof, a Neurogenin3 gene or one or more gene products thereof, a Pdx1 gene or one or more gene products thereof, and a MafA gene or one or more gene products thereof; and (D) a mutated GLIS1 gene having a sequence identity of 85% or more to a base sequence as set forth in SEQ ID NO: 1 or 2 or one or more gene products thereof, a Neurogenin3 gene or one or more gene products thereof, and a MafA gene or one or more gene products thereof:

wherein the transdifferentiation agent is configured to transdifferentiate somatic cells into pancreatic endocrine cells.

<9> The transdifferentiation agent according to <8>, wherein (A), (B), (C), or (D) is (A) a mutated GLIS1 gene having a sequence identity of 85% or more to a base sequence as set forth in SEQ ID NO: 1 or 2 or one or more gene products thereof, a Neurogenin3 gene or one or more gene products thereof, a Pdx1 gene or one or more gene products thereof, and a MafA gene or one or more gene products thereof.

<10> The transdifferentiation agent according to <8>, wherein (A), (B), (C), or (D) is (B) a mutated GLIS1 gene having a sequence identity of 85% or more to a base sequence as set forth in SEQ ID NO: 1 or 2 or one or more gene products thereof, a Neurogenin3 gene or one or more gene products thereof, and a Pdx1 gene or one or more gene products thereof.

<11> The transdifferentiation agent according to <8>, wherein (A), (B), (C), or (D) is (C) a GLIS1 gene or one or more gene products thereof, a Neurogenin3 gene or one or more gene products thereof, a Pdx1 gene or one or more gene products thereof, and a MafA gene or one or more gene products thereof.

<12> The transdifferentiation agent according to <8>, wherein (A), (B), (C), or (D) is (D) a mutated GLIS1 gene having a sequence identity of 85% or more to a base sequence as set forth in SEQ ID NO: 1 or 2 or one or more gene products thereof, a Neurogenin3 gene or one or more gene products thereof, and a MafA gene or one or more gene products thereof.

<13> The transdifferentiation agent according to any one of <8> to <12>, wherein the somatic cells are fibroblasts or mesenchymal stem cells.

<14> The transdifferentiation agent according to any one of <8> to <13>, wherein the pancreatic endocrine cells are β cells.

<15> A method for producing pancreatic endocrine cells, the method including introducing (B) or (D) below into cultured somatic cells to transdifferentiate into a population of pancreatic endocrine cells comprising insulin-producing beta-cells:

(B) a GLIS1 gene or one or more gene products thereof, a Neurogenin3 gene or one or more gene products thereof, and a Pdx1 gene or one or more gene products thereof;

(D) a GLIS1 gene or one or more gene products thereof, a Neurogenin3 gene or one or more gene products thereof, and a MafA gene or one or more gene products thereof, wherein the GLIS1 gene comprises the nucleotide sequence as set forth in SEQ ID NO: 1 or SEQ ID NO: 2, and wherein the population of pancreatic endocrine cells are produced without undergoing an iPS cell stage.

<16> The method for producing pancreatic endocrine cells according to <15>, wherein the somatic cells are fibroblasts or mesenchymal stem cells.

<17> A transdifferentiation agent including (B) or (D) below:

(B) a GLIS1 gene or one or more gene products thereof, a Neurogenin gene or one or more gene products thereof, and a Pdx1 gene or one or more gene products thereof;

and (D) a GLIS1 gene or one or more gene products thereof, a Neurogenin3 gene or one or more gene products thereof, and a MafA gene or one or more gene products thereof, wherein the GLIS1 gene comprises the nucleotide sequence as set forth in SEO ID NO: 1 or SEQ ID NO: 2, wherein the transdifferentiation agent is configured to transdifferentiate cultured somatic cells into a population of pancreatic endocrine cells comprising insulin-producing beta-cells, and wherein the population of pancreatic endocrine cells are produced without undergoing an iPS cell stage <18> The method for producing pancreatic endocrine cells according to <17>, wherein the somatic cells are fibroblasts or mesenchymal stem cells.

The invention claimed is:

1. An in vitro method for producing pancreatic beta-cells, the method comprising:
   introducing a GLIS1 gene, a Neurogenin3 gene and a Pdx1 gene into somatic cells and culturing in a media for a time sufficient to transdifferentiate into a population of insulin-producing beta-cells expressing insulin gene
   wherein the GLIS1 gene consists of the nucleotide sequence as set forth in SEQ ID NO: 1 or SEQ ID NO: 2,
   wherein each of the GLIS 1 gene, the Neurogenin3 gene and the Pdx1 gene is incorporated into one vector,
   wherein the population of insulin-producing beta-cells are produced without undergoing an iPS cell stage, and
   wherein the somatic cells are fibroblasts, renal cells, hepatic cells or mesenchymal stem cells.

2. The method for producing pancreatic beta-cells according to claim 1, wherein the media is at least one selected from the group consisting of: minimum essential media (MEM), Dulbecco's modified Eagle media (DMEM), RPMI1640 media, 199 media, and F12 media.

* * * * *

SEQUENCE LISTING

```
<160> NUMBER OF SEQ ID NOS: 37

<210> SEQ ID NO 1
<211> LENGTH: 1290
<212> TYPE: DNA
<213> ORGANISM: Artificial Sequence
<220> FEATURE:
<223> OTHER INFORMATION: Synthesized sequence

<400> SEQUENCE: 1
atggttgccg gtcggcaggc atgccgctgg gtggactgct gcgcagccta cgagcagcag     60
gaggagctgg tgcggcacat cgagaagagc cacatcgacc agcgcaaggg cgaagacttc    120
acctgcttct gggccgggtg tgtgcggcgc tacaagccct tcaatgcccg ctacaagctg    180
ctcatccaca tgagggtaca ctcaggcgag aagcccaaca agtgcatgtt cgaaggctgc    240
agtaaagcct tttcccgtct ggagaacctg aagatccatc tgcggagcca cacaggcgag    300
```

| | |
|---|---|
| aaaccatacc tgtgccagca cccaggctgc cagaaggcct tcagcaactc cagcgaccgt | 360 |
| gccaagcacc aacgcaccca cctcgacacg aagccatatg cttgtcagat ccctggctgc | 420 |
| tccaagcgct acacggaccc cagctccctc cgcaagcacg tgaaggccca ctcagccaaa | 480 |
| gagcagcagg tgcgtaagaa gctgcacaca ggtgccgacc cagaggctga tgttctgtcc | 540 |
| gagtgtctgt ccctgcagca gctccaagca tccacactgt tgccggccag cagagggaag | 600 |
| ggcagccaaa ccctgagcca ggagctcctc ccaggtgtgt atcctggctc cgtcacccca | 660 |
| caaaacgggc ttgcttcagg catcctgtcc cctcccacg atgtcccttc caggcaccac | 720 |
| ccactggagg tccccactgg ttcccaccac cacctgtccc ctctgccac agctgagagc | 780 |
| accagggatg gcctggggcc cagtctcctt tcacccatgg tcagcccact gaagggcttg | 840 |
| ggtcccccac cgctaccacc agcctcccag agtcagtctc caggggggaca gtcattctct | 900 |
| acagtcccca gcaagcctac ctacccatcc ttccaaagcc caccacctct gcccagcccc | 960 |
| caaggctacc aaggcagttt ccattccatc cagaactgct tccctacgc tgactgctac | 1020 |
| cgggccactg agccagcagc ctccagggat ggactggtgg gtgatgccca cggtttcaac | 1080 |
| cccttgcgac ccagcacata ctccagcctc agcacaccctt tatccgcacc aggctacgag | 1140 |
| accctggcag aaacgccgtg tccccagcg ctgcagccac agccagctga agacctggta | 1200 |
| cctagtggtc ctgaggactg tggcttcttc cccaatgggg cctttgacca ctgtctgagt | 1260 |
| cacatcccgt ccatctacac tgacacctga | 1290 |

<210> SEQ ID NO 2
<211> LENGTH: 1299
<212> TYPE: DNA
<213> ORGANISM: Artificial Sequence
<220> FEATURE:
<223> OTHER INFORMATION: Synthesized sequence

<400> SEQUENCE: 2

| | |
|---|---|
| atggtggtgg ccgggcggca ggcgtgccgc tgggtggact gctgtgcagc ctatgagcag | 60 |
| caggaggagc tggtgcggca catcgagaag agccacatcg accagcgcaa gggcgaggac | 120 |
| ttcacctgct ctgggctgg ctgcgtgcgc cgctacaagc ccttcaacgc ccgctacaag | 180 |
| ctgctcatcc acatgcgagt gcactcgggc gagaagccca caagtgcat gtttgaaggc | 240 |
| tgcagcaagg ccttctcacg gctggagaac ctcaagatcc acctgaggag ccacacgggc | 300 |
| gagaagccgt acctgtgcca gcacccgggt tgccagaagg ccttcagcaa ctccagcgac | 360 |
| cgcgccaagc accagcgcac ccacctagac acgaagccgt acgcctgtca gatccctggc | 420 |
| tgctccaagc gctacacaga ccccagctcc ctccgcaagc acgtcaaggc ccattcagcc | 480 |
| aaagagcagc aggtgcgtaa gaagctgcat gcgggccctg acaccgaggc cgacgtcctg | 540 |
| accgagtgtc tggtcctgca gcagctccac acgtccacac agctggctgc cagcgacggc | 600 |
| aagggtggct gtggcctggg ccaggagctg ctcccaggtg tgtatcctgg ctccatcacc | 660 |
| ccccataacg gacttgcatc gggcctcctg cccccagcgc acgacgtacc ttccaggcac | 720 |
| cacccgctgg atgccaccac cagttcccac caccatctgt cccctctgcc catggctgag | 780 |
| agcacccggg atgggttggg gcccggcctc ctctcaccaa tagtcagccc cctgaagggg | 840 |
| ctggggccac cgccgctgcc ccatcctct cagagccatt ctccggggg ccagcccttc | 900 |
| cccacactcc ccagcaagcc gtcctaccca cccttccaga gccctccacc ccgcctctg | 960 |
| cccagcccac aaggttacca gggcagtttc cactccatcc agagttgctt ccctatggc | 1020 |

-continued

```
gactgctacc ggatggctga accagcagcc ggtggggacg gactggtcgg ggagacccac      1080
ggtttcaacc ccctgcggcc caatggctac cacagcctca gcacgccctt gcctgccaca      1140
ggctatgagg ccctggctga ggcctcatgc cccacagcgc tgccacagca gccatctgaa      1200
gatgtggtgt ccagcggccc cgaggactgt ggcttcttcc ccaatggagc ctttgaccac      1260
tgcctgggcc acatcccctc catctacaca gacacctga                             1299

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
tggagaaacc tgccaagtat g                                                 21

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ggagacaacc tggtcctcag                                                   20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
tttgtcaagc agcacctttg                                                   20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
ggtctgaagg tcacctgctc                                                   20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
atgttcgtca tgggtgtgaa                                                   20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
```

```
tgtggtcatg agtccttcca                                                  20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
gccatcaagc agatcactgt                                                  20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
caggtgttgg ttcacaaagg                                                  20

<210> SEQ ID NO 11
<211> LENGTH: 192
<212> TYPE: DNA
<213> ORGANISM: Artificial Sequence
<220> FEATURE:
<223> OTHER INFORMATION: Synthesized sequence

<400> SEQUENCE: 11
tccagtgacg gccaggaggg cagcttgcag cttgaagcat gccggaagtc aggcttcctg      60
aagcaggagc ccatggacga gttttcagag ctttttgctc cacaccacca gggtttgcca     120
cccccttacc ccttgcctca gttgccaact ggccccggcc tcggaggcct agggctgggc     180
ctggcaggta gg                                                         192

<210> SEQ ID NO 12
<211> LENGTH: 1482
<212> TYPE: DNA
<213> ORGANISM: Artificial Sequence
<220> FEATURE:
<223> OTHER INFORMATION: Synthesized sequence

<400> SEQUENCE: 12
tccagtgacg gccaggaggg cagcttgcag cttgaagcat gccggaagtc aggcttcctg      60
aagcaggagc ccatggacga gttttcagag ctttttgctc cacaccacca gggtttgcca     120
cccccttacc ccttgcctca gttgccaact ggccccggcc tcggaggcct agggctgggc     180
ctggcaggta ggatggttgc cggtcggcag gcatgccgct gggtggactg ctgcgcagcc     240
tacgagcagc aggaggagct ggtgcggcac atcgagaaga gccacatcga ccagcgcaag     300
ggcgaagact tcacctgctt ctgggccggg tgtgtgcggc gctacaagcc cttcaatgcc     360
cgctacaagc tgctcatcca catgagggta cactcaggcg agaagcccaa caagtgcatg     420
ttcgaaggct gcagtaaagc cttttcccgt ctggagaacc tgaagatcca tctgcggagc     480
cacacaggcg agaaaccata cctgtgccag caccccaggct gccagaaggc cttcagcaac     540
tccagcgacc gtgccaagca ccaacgcacc cacctcgaca cgaagccata tgcttgtcag     600
atccctggct gctccaagcg ctacacggac cccagctccc tcgcaagca cgtgaaggcc     660 cactcagcca aagagcagca ggtgcgtaag aagctgcaca caggtgccga cccagaggct     720
```

|  |  |  |
|---|---|---|
| gatgttctgt ccgagtgtct gtccctgcag cagctccaag catccacact gttgccggcc | 780 |
| agcagaggga agggcagcca aaccctgagc caggagctcc tcccaggtgt gtatcctggc | 840 |
| tccgtcaccc cacaaaacgg gcttgcttca ggcatcctgt ccccctccca cgatgtccct | 900 |
| tccaggcacc acccactgga ggtccccact ggttcccacc accacctgtc ccctctgccc | 960 |
| acagctgaga gcaccaggga tggcctgggg cccagtctcc tttcacccat ggtcagccca | 1020 |
| ctgaaggggc ttggtccccc accgctacca ccagcctccc agagtcagtc tccaggggga | 1080 |
| cagtcattct ctacagtccc cagcaagcct acctaccccat ccttccaaag cccaccacct | 1140 |
| ctgcccagcc cccaaggcta ccaaggcagt ttccattcca tccagaactg cttccctac | 1200 |
| gctgactgct accgggccac tgagccagca gcctccaggg atggactggt gggtgatgcc | 1260 |
| cacggtttca accccttgcg acccagcaca tactccagcc tcagcacacc tttatccgca | 1320 |
| ccaggctacg agaccctggc agaaacgccg tgtccccag cgctgcagcc acagccagct | 1380 |
| gaagacctgg tacctagtgg tcctgaggac tgtggcttct tccccaatgg ggcctttgac | 1440 |
| cactgtctga gtcacatccc gtccatctac actgacacct ga | 1482 |

<210> SEQ ID NO 13
<211> LENGTH: 46
<212> TYPE: DNA
<213> ORGANISM: Artificial Sequence
<220> FEATURE:
<223> OTHER INFORMATION: primer

<400> SEQUENCE: 13

|  |  |
|---|---|
| agttaattaa ggatccgcca ccatgtccag tgacggccag gagggc | 46 |

<210> SEQ ID NO 14
<211> LENGTH: 48
<212> TYPE: DNA
<213> ORGANISM: Artificial Sequence
<220> FEATURE:
<223> OTHER INFORMATION: primer

<400> SEQUENCE: 14

|  |  |
|---|---|
| ctggcggccg ctcgagttat ttattcaggt gtcagtgtag atggacgg | 48 |

<210> SEQ ID NO 15
<211> LENGTH: 78
<212> TYPE: DNA
<213> ORGANISM: Artificial Sequence
<220> FEATURE:
<223> OTHER INFORMATION: Synthesized sequence

<400> SEQUENCE: 15

|  |  |
|---|---|
| atggactaca agaccatga cggtgattat aaagatcatg acatcgatta caaggatgac | 60 |
| gatgacaagg gaagcgga | 78 |

<210> SEQ ID NO 16
<211> LENGTH: 48
<212> TYPE: DNA
<213> ORGANISM: Artificial Sequence
<220> FEATURE:
<223> OTHER INFORMATION: Synthesized sequence

<400> SEQUENCE: 16

|  |  |
|---|---|
| ggatccacta gtggcgttgc catgccaggt gccgaagatg atgtggtg | 48 |

<210> SEQ ID NO 17
<211> LENGTH: 1416

```
<212> TYPE: DNA
<213> ORGANISM: Artificial Sequence
<220> FEATURE:
<223> OTHER INFORMATION: Synthesized sequence

<400> SEQUENCE: 17
atggactaca aagaccatga cggtgattat aaagatcatg acatcgatta caaggatgac    60
gatgacaagg gaagcggaat ggttgccggt cggcaggcat gccgctgggt ggactgctgc   120
gcagcctacg agcagcagga ggagctggtg cggcacatcg agaagagcca catcgaccag   180
cgcaagggcg aagacttcac ctgcttctgg gccgggtgtg tgcggcgcta caagcccttc   240
aatgcccgct acaagctgct catccacatg agggtacact caggcgagaa gcccaacaag   300
tgcatgttcg aaggctgcag taaagccttt tcccgtctgg agaacctgaa gatccatctg   360
cggagccaca caggcgagaa accatacctg tgccagcacc caggctgcca gaaggccttc   420
agcaactcca gcgaccgtgc caagcaccaa cgcacccacc tcgacacgaa gccatatgct   480
tgtcagatcc ctggctgctc caagcgctac acggacccca gctccctccg caagcacgtg   540
aaggcccact cagccaaaga gcagcaggtg cgtaagaagc tgcacacagg tgccgaccca   600
gaggctgatt ttctgtccga gtgtctgtcc ctgcagcagc tccaagcatc cacactgttg   660
ccggccagca gagggaaggg cagccaaacc ctgagccagg agctcctccc aggtgtgtat   720
cctggctccg tcaccccaca aaacgggctt gcttcaggca tcctgtcccc ctcccacgat   780
gtcccttcca ggcaccaccc actggaggtc cccactggtt ccaccacca cctgtcccct   840 ctgcccacag ctgagagcac cagggatggc ctggggccca gtctcctttc acccatggtc   900
agcccactga aggggcttgg tcccccaccg ctaccaccag cctcccagag tcagtctcca   960
gggggacagt cattctctac agtccccagc aagcctacct acccatcctt ccaaagccca  1020
ccacctctgc ccagccccca aggctaccaa ggcagtttcc attccatcca gaactgcttc  1080
ccctacgctg actgctaccg ggccactgag ccagcagcct caggatgg actggtgggt  1140 gatgcccacg gtttcaaccc cttgcgaccc agcacatact ccagcctcag cacacctta   1200 tccgcaccag gctacgagac cctggcagaa acgccgtgtc ccccagcgct gcagccacag  1260
ccagctgaag acctggtacc tagtggtcct gaggactgtg gcttcttccc caatggggcc  1320
tttgaccact gtctgagtca catcccgtcc atctacactg acacctgagg atccactagt  1380
ggcgttgcca tgccaggtgc cgaagatgat gtggtg                             1416

<210> SEQ ID NO 18
<211> LENGTH: 123
<212> TYPE: DNA
<213> ORGANISM: Artificial Sequence
<220> FEATURE:
<223> OTHER INFORMATION: primer

<400> SEQUENCE: 18
agttaattaa ggatccgcca ccatggacta caaagaccat gacggtgatt ataaagatca    60
tgacatcgat tacaaggatg acgatgacaa gggaagcgga gttgccggtc ggcaggcatg   120
ccg                                                                 123

<210> SEQ ID NO 19
<211> LENGTH: 89
<212> TYPE: DNA
<213> ORGANISM: Artificial Sequence
<220> FEATURE:
<223> OTHER INFORMATION: primer
```

<400> SEQUENCE: 19

```
ctggcggccg ctcgagttac accacatcat cttcggcacc tggcatggca acgccactag    60
tggatccggt gtcagtgtag atggacggg                                      89
```

<210> SEQ ID NO 20
<211> LENGTH: 1770
<212> TYPE: DNA
<213> ORGANISM: Artificial Sequence
<220> FEATURE:
<223> OTHER INFORMATION: Synthesized sequence

<400> SEQUENCE: 20

```
ggcctcacca accctgcacc ttcctgctac cttctgggca atgaacccat ctcagacctg      60
ggtccccaac ccgaggccca cctccccgag ggcagcctga acgctgctg cctcctgggc     120
ctgcccccca cctcttcagc ctcctcctca ccctgtgcct cctcagatat caatcctgtc    180
atccactcct cccagacagc tctagttagc tgtgtaaatg gactccgaag cccacctctg    240
ccgggagacc tggggggccc tcccaagcgg tcacggcccg ggcctgcatc cagtgacggc    300
caggagggca gcttgcagct tgaagcatgc cggaagtcag gcttcctgaa gcaggagccc    360
atggacgagt tttcagagct ttttgctcca caccaccagg gtttgccacc cccttacccc    420
ttgcctcagt tgccaactgg ccccggcctc ggaggcctag ggctgggcct ggcaggtagg    480
atggttgccg gtcggcaggc atgccgctgg gtggactgct cgcagcctac gagcagcag    540
gaggagctgg tgcggcacat cgagaagagc cacatcgacc agcgcaaggg cgaagacttc    600
acctgcttct gggccgggtg tgtgcggcgc tacaagcct tcaatgcccg ctacaagctg    660
ctcatccaca tgagggtaca ctcaggcgag aagcccaaca gtgcatgtt cgaaggctgc    720
agtaaagcct tttcccgtct ggagaacctg aagatccatc tgcggagcca cacaggcgag    780
aaaccatacc tgtgccagca cccaggctgc cagaaggcct tcagcaactc cagcgaccgt    840
gccaagcacc aacgcaccca cctcgacacg aagccatatg cttgtcagat ccctggctgc    900
tccaagcgct acacggaccc cagctccctc cgcaagcacg tgaaggccca ctcagccaaa    960
gagcagcagg tgcgtaagaa gctgcacaca ggtgccgacc agaggctga tgttctgtcc   1020
gagtgtctgt ccctgcagca gctccaagca tccacactgt tgccggccag cagagggaag   1080
ggcagccaaa ccctgagcca ggagctcctc ccaggtgtgt atcctggctc cgtcacccca   1140
caaaacgggc ttgcttcagg catcctgtcc ccctcccacg atgtcccttc caggcaccac   1200
ccactggagg tccccactgg ttcccaccac cacctgtccc ctctgcccac agctgagagc   1260
accagggatg gcctggggcc cagtctcctt tcacccatgg tcagcccact gaaggggctt   1320
ggtcccccac cgctaccacc agcctccag agtcagtctc caggggaca gtcattctct   1380
acagtcccca gcaagcctac ctacccatcc ttccaaagcc caccacctct gcccagcccc   1440
caaggctacc aaggcagttt ccattccatc cagaactgct tccctacgc tgactgctac   1500
cgggccactg agccagcagc ctccagggat ggactggtgg gtgatgccca cggtttcaac   1560
cccttgcgac ccagcacata ctccagcctc agcacacctt tatccgcacc aggctacgag   1620
accctggcag aaacgccgtg tccccagcg ctgcagccac agccagctga agacctggta   1680
cctagtggtc ctgaggactg tggcttcttc cccaatgggg cctttgacca ctgtctgagt   1740
cacatcccgt ccatctacac tgacacctga                                    1770
```

<210> SEQ ID NO 21
<211> LENGTH: 43

```
<212> TYPE: DNA
<213> ORGANISM: Artificial Sequence
<220> FEATURE:
<223> OTHER INFORMATION: primer

<400> SEQUENCE: 21
agttaattaa ggatccacca tgggcctcac caaccctgca cct                43

<210> SEQ ID NO 22
<211> LENGTH: 48
<212> TYPE: DNA
<213> ORGANISM: Artificial Sequence
<220> FEATURE:
<223> OTHER INFORMATION: primer

<400> SEQUENCE: 22
ctggcggccg ctcgagttat ttattcaggt gtcagtgtag atggacgg           48

<210> SEQ ID NO 23
<211> LENGTH: 900
<212> TYPE: DNA
<213> ORGANISM: Artificial Sequence
<220> FEATURE:
<223> OTHER INFORMATION: Synthesized sequence

<400> SEQUENCE: 23
aagccatatg cttgtcagat ccctggctgc tccaagcgct acacggaccc cagctccctc    60
cgcaagcacg tgaaggccca ctcagccaaa gagcagcagg tgcgtaagaa gctgcacaca   120
ggtgccgacc cagaggctga tgttctgtcc gagtgtctgt ccctgcagca gctccaagca   180
tccacactgt tgccggccag cagagggaag ggcagccaaa ccctgagcca ggagctcctc   240
ccaggtgtgt atcctggctc cgtcaccccca caaaacgggc ttgcttcagg catcctgtcc   300
ccctcccacg atgtcccttc caggcaccac ccactggagg tccccactgg ttcccaccac   360
cacctgtccc ctctgccac agctgagagc accaggatg gcctgggcc cagtctcctt   420 tcacccatgg tcagcccact gaaggggctt ggtcccccac cgctaccacc agcctcccag   480
agtcagtctc caggggggaca gtcattctct acagtcccca gcaagcctac ctacccatcc   540
ttccaaagcc caccacctct gcccagcccc caaggctacc aaggcagttt ccattccatc   600
cagaactgct tccctacgc tgactgctac cgggccactg agccagcagc ctccagggat   660
ggactggtgg gtgatgccca cggttttcaac cccttgcgac ccagcacata ctccagcctc   720
agcacacctt tatccgcacc aggctacgag accctggcag aaacgccgtg tcccccagcg   780
ctgcagccac agccagctga agacctggta cctagtggtc ctgaggactg tggcttcttc   840
cccaatgggg cctttgacca ctgtctgagt cacatcccgt ccatctacac tgacacctga   900

<210> SEQ ID NO 24
<211> LENGTH: 46
<212> TYPE: DNA
<213> ORGANISM: Artificial Sequence
<220> FEATURE:
<223> OTHER INFORMATION: primer

<400> SEQUENCE: 24
agttaattaa ggatccacca tgaagccata tgcttgtcag atccct             46

<210> SEQ ID NO 25
<211> LENGTH: 48
<212> TYPE: DNA
<213> ORGANISM: Artificial Sequence
<220> FEATURE:
```

<223> OTHER INFORMATION: primer

<400> SEQUENCE: 25
ctggcggccg ctcgagttat ttattcaggt gtcagtgtag atggacgg          48

<210> SEQ ID NO 26
<211> LENGTH: 1620
<212> TYPE: DNA
<213> ORGANISM: Artificial Sequence
<220> FEATURE:
<223> OTHER INFORMATION: Synthesized sequence

<400> SEQUENCE: 26
atgcattgcg aggtggccga ggcactttcg acaagaggc caaggaggc cctggtgct      60 cctggccagg gccgcgggcc tgtcagcctg ggagcgcaca tggccttcag gattgctgtg    120
agtggtggcg gctgcgggga cgggaacccc ctagacctgc tgcctcggct accggtgcca    180
ccaccacgtg cccacgatct ccttcggccc cggagccctc gagactatgg tgtgtccaag    240
accggcagcg ggaaggtgaa cgggagctac ggcacagct cagagaagag cctgctggac    300
ctggacctgg ccgagggtcc cagcccctcc tgccaccagg gtctgtttct tcctgcaggg    360
accccaccac cccggggtca ccccctgtc tgtgagaagc tgctgcactt cccccaccca    420
aacaggtcac ccagacctca ggctacgttt gtgaacggca gcctcccagc cgctcagcac    480
atcaagcaag aagccctacc ggactaccag gccatggtca gcgcccacac accctgccc    540 acccactgcc gagccccatc gtccatgggt ctgccctcag acctggactt ccagaccga    600 ggcctcacca ccctgcacc ttcctgctac cttctgggca tgaacccat ctcagacctg    660 ggtccccaac ccgaggccca cctccccgag ggcagcctga acgctgctg cctcctgggc    720 ctgcccccca cctcttcagc ctcctcctca ccctgtgcct cctcagatat caatcctgtc    780
atccactcct cccagacagc tctagttagc tgtgtaaatg gactccgaag cccacctctg    840
ccgggagacc tgggggggccc tcccaagcgg tcacggcccg ggcctgcatc cagtgacggc    900
caggagggca gcttgcagct tgaagcatgc cggaagtcag gcttcctgaa gcaggagccc    960
atggacgagt tttcagagct tttttgctcca caccaccagg gtttgccacc cccttaccc    1020 ttgcctcagt tgccaactgg ccccggcctc ggaggcctag ggctgggcct ggcaggtagg    1080
atggttgccg gtcggcaggc atgccgctgg gtggactgct gcgcagccta cgagcagcag    1140
gaggagctgg tgcggcacat cgagaagagc cacatcgacc agcgcaaggg cgaagacttc    1200
acctgcttct gggccgggtg tgtgcggcgc tacaagcccc tcaatgcccg ctacaagctg    1260
ctcatccaca tgagggtaca ctcaggcgag aagcccaaca gtgcatgtt cgaaggctgc    1320 agtaaagcct tttccccgtct ggagaacctg aagatccatc tgcggagcca cacaggcgag    1380
aaaccatacc tgtgccagca cccaggctgc cagaaggcct tcagcaactc cagcgaccgt    1440
gccaagcacc aacgcaccca cctcgacacg aagccatatg cttgtcagat ccctggctgc    1500
tccaagcgct acacggaccc cagctccctc cgcaagcacg tgaaggccca ctcagccaaa    1560
gagcagcagg tgcgtaagaa gctgcacaca ggtgccgacc cagaggctga tgttctgtcc    1620

<210> SEQ ID NO 27
<211> LENGTH: 33
<212> TYPE: DNA
<213> ORGANISM: Artificial Sequence
<220> FEATURE:
<223> OTHER INFORMATION: primer

<400> SEQUENCE: 27

```
agttaattaa ggatcccagt gtggtggtac ggg                                33
```

<210> SEQ ID NO 28
<211> LENGTH: 48
<212> TYPE: DNA
<213> ORGANISM: Artificial Sequence
<220> FEATURE:
<223> OTHER INFORMATION: primer

<400> SEQUENCE: 28

```
ctggcggccg ctcgagttat ttattcagga cagaacatca gcctctgg              48
```

<210> SEQ ID NO 29
<211> LENGTH: 1494
<212> TYPE: DNA
<213> ORGANISM: Artificial Sequence
<220> FEATURE:
<223> OTHER INFORMATION: Synthesized sequence

<400> SEQUENCE: 29

```
atgcattgcg aggtggccga ggcactttcg acaagaggc caaggaggc cctggtgct      60
cctggccagg gccgcgggcc tgtcagcctg ggagcgcaca tggccttcag gattgctgtg  120
agtggtggcg gctgcgggga cgggaacccc ctagacctgc tgcctcggct accggtgcca  180
ccaccacgtg cccacgatct ccttcggccc cggagccctc gagactatgg tgtgtccaag  240
accggcagcg ggaaggtgaa cgggagctac ggcacagcct cagagaagag cctgctggac  300
ctggacctgg ccgagggtcc cagccccctcc tgccaccagg gtctgttttct tcctgcaggg  360
acccccaccac cccgggggtca ccccccctgtc tgtgagaagc tgctgcactt cccccaccca  420
aacaggtcac ccagacctca ggctacgttt gtgaacggca gcctcccagc cgctcagcac  480
atcaagcaag aagccctacc ggactaccag gccatggtca gcgcccacac acccctgccc  540
acccactgcc gagccccatc gtccatgggt ctgccctcag acctggactt tccagaccga  600
ggcctcacca accctgcacc ttcctgctac cttctgggca tgaacccat ctcagacctg  660
ggtccccaac ccgaggccca cctccccgag ggcagcctga acgctgctg cctcctgggc  720
ctgcccccca cctcttcagc ctcctcctca ccctgtgcct cctcagatat caatcctgtc  780
atccactcct cccagacagc tctagttagc tgtgtaaatg gactccgaag cccacctctg  840
ccgggagacc tggggggccc tcccaagcgg tcacggcccg ggcctgcatc cagtgacggc  900
caggagggca gcttgcagct tgaagcatgc cggaagtcag gcttcctgaa gcaggagccc  960
atggacgagt tttcagagct ttttgctcca caccaccagg gtttgccacc cccttacccc 1020
ttgcctcagt tgccaactgg ccccggcctc ggaggcctag gctgggcct ggcaggtagg 1080
atggttgccg gtcggcaggc atgccgctgg gtggactgct gcgcagccta cgagcagcag 1140
gaggagctgg tgcggcacat cgagaagagc cacatcgacc agcgcaaggg cgaagacttc 1200
acctgcttct gggccgggtg tgtgcggcgc tacaagccct caatgcccg ctacaagctg 1260
ctcatccaca tgagggtaca ctcaggcgag aagcccaaca agtgcatgtt cgaaggctgc 1320
agtaaagcct tttcccgtct ggagaacctg aagatccatc tgcggagcca cacaggcgag 1380
aaaccatacc tgtgccagca cccaggctgc cagaaggcct tcagcaactc cagcgaccgt 1440
gccaagcacc aacgcaccca cctcgacacg aagccatatg cttgtcagat ccct         1494
```

<210> SEQ ID NO 30
<211> LENGTH: 42
<212> TYPE: DNA

<213> ORGANISM: Artificial Sequence
<220> FEATURE:
<223> OTHER INFORMATION: primer

<400> SEQUENCE: 30
agttaattaa ggatccacca tgcattgcga ggtggccgag gc        42

<210> SEQ ID NO 31
<211> LENGTH: 48
<212> TYPE: DNA
<213> ORGANISM: Artificial Sequence
<220> FEATURE:
<223> OTHER INFORMATION: primer

<400> SEQUENCE: 31
ctggcggccg ctcgagttat ttattcaagg gatctgacaa gcatatgg        48

<210> SEQ ID NO 32
<211> LENGTH: 435
<212> TYPE: DNA
<213> ORGANISM: Artificial Sequence
<220> FEATURE:
<223> OTHER INFORMATION: ZFD of Glis1

<400> SEQUENCE: 32
caggcatgcc gctgggtgga ctgctgcgca gcctacgagc agcaggagga gctggtgcgg        60
cacatcgaga gagccacat cgaccagcgc aagggcgaag acttcacctg cttctgggcc        120
gggtgtgtgc ggcgctacaa gcccttcaat gcccgctaca agctgctcat ccacatgagg        180
gtacactcag gcgagaagcc caacaagtgc atgttcgaag gctgcagtaa agccttttcc        240
cgtctggaga acctgaagat ccatctgcgg agccacacag gcgagaaacc atacctgtgc        300
cagcacccag gctgccagaa ggccttcagc aactccagcg accgtgccaa gcaccaacgc        360
acccacctcg acacgaagcc atatgcttgt cagatccctg gctgctccaa gcgctacacg        420
gaccccagct ccctc        435

<210> SEQ ID NO 33
<211> LENGTH: 1935
<212> TYPE: DNA
<213> ORGANISM: Artificial Sequence
<220> FEATURE:
<223> OTHER INFORMATION: Synthesized sequence

<400> SEQUENCE: 33
atgcattgcg aggtggccga ggcactttcg gacaagaggc caaggaggc ccctggtgct        60
cctggccagg gccgcgggcc tgtcagcctg ggagcgcaca tggccttcag gattgctgtg        120
agtggtggcg gctgcgggga cgggaacccg ctagacctgc tgcctcggct accggtgcca        180
ccaccacgtg cccacgatct ccttcggccc cggagccctc gagactatgg tgtgtccaag        240
accggcagcg ggaaggtgaa cgggagctac gggcacagct cagagaagag cctgctggac        300
ctggacctgg ccgagggtcc cagccctcc tgccaccagg gtctgtttct tcctgcaggg        360
accccaccac cccgggggtca cccccctgtc tgtgagaagc tgctgcactt cccccaccca        420
aacaggtcac ccagacctca ggctacgttt gtgaacggca gcctcccagc cgctcagcac        480
atcaagcaag aagccctacc ggactaccag gccatggtca gcgcccacac acccctgccc        540
acccactgcc gagccccatc gtccatgggt ctgccctcag acctggactt tccagaccga        600
ggcctcacca accctgcacc ttcctgctac ctttctggga atgaaccat ctcagacctg        660
ggtccccaac ccgaggccca cctcccccgag ggcagcctga acgctgctg cctcctgggc        720

-continued

```
ctgcccccca cctcttcagc ctcctcctca ccctgtgcct cctcagatat caatcctgtc      780
atccactcct cccagacagc tctagttagc tgtgtaaatg gactccgaag cccacctctg      840
ccgggagacc tgggggccc tcccaagcgg tcacggcccg ggcctgcatc cagtgacggc       900
caggagggca gcttgcagct tgaagcatgc cggaagtcag gcttcctgaa gcaggagccc      960
atggacgagt tttcagagct ttttgctcca caccaccagg gtttgccacc cccttacccc     1020
ttgcctcagt tgccaactgg ccccggcctc ggaggcctag ggctgggcct ggcaggtagg     1080
atggttgccg gtcggcgcaa gcacgtgaag gcccactcag ccaaagagca gcaggtgcgt     1140
aagaagctgc acacaggtgc cgacccgag gctgatgttc tgtccgagtg tctgtccctg      1200
cagcagctcc aagcatccac actgttgccg ccagcagag ggaagggcag ccaaaccctg      1260
agccaggagc tcctcccagg tgtgtatcct ggctccgtca ccccacaaaa cgggcttgct     1320
tcaggcatcc tgtcccctc ccacgatgtc ccttccaggc accccact ggaggtcccc        1380 actggttccc accaccacct gtcccctctg cccacagctg agagcaccag ggatggcctg     1440
gggcccagtc tcctttcacc catggtcagc ccactgaagg ggcttggtcc cccaccgcta     1500
ccaccagcct cccagagtca gtctccaggg ggacagtcat tctctacagt ccccagcaag     1560
cctacctacc catccttcca aagcccacca cctctgccca gccccaagg ctaccaaggc      1620 agtttccatt ccatccagaa ctgcttcccc tacgctgact gctaccgggc cactgagcca     1680
gcagcctcca gggatggact ggtgggtgat gcccacggtt tcaaccccctt gcgacccagc    1740 acatactcca gcctcagcac acctttatcc gcaccaggct acgagaccct ggcagaaacg     1800
ccgtgtcccc cagcgctgca gccacagcca gctgaagacc tggtacctag tggtcctgag    1860
gactgtggct tcttccccaa tggggccttt gaccactgtc tgagtcacat cccgtccatc    1920
tacactgaca cctga                                                      1935
```

```
<210> SEQ ID NO 34
<211> LENGTH: 34
<212> TYPE: DNA
<213> ORGANISM: Artificial Sequence
<220> FEATURE:
<223> OTHER INFORMATION: primer

<400> SEQUENCE: 34
agttaattaa ggatcccagt gtggtggtac ggga                                   34

<210> SEQ ID NO 35
<211> LENGTH: 21
<212> TYPE: DNA
<213> ORGANISM: Artificial Sequence
<220> FEATURE:
<223> OTHER INFORMATION: primer

<400> SEQUENCE: 35
ccgaccggca accatcctac c                                                 21

<210> SEQ ID NO 36
<211> LENGTH: 36
<212> TYPE: DNA
<213> ORGANISM: Artificial Sequence
<220> FEATURE:
<223> OTHER INFORMATION: primer

<400> SEQUENCE: 36
atggttgccg gtcggcgcaa gcacgtgaag gcccac                                 36
```

```
<210> SEQ ID NO 37
<211> LENGTH: 48
<212> TYPE: DNA
<213> ORGANISM: Artificial Sequence
<220> FEATURE:
<223> OTHER INFORMATION: primer

<400> SEQUENCE: 37
ctggcggccg ctcgagttat ttattcaggt gtcagtgtag atggacgg        48
```